(12) United States Patent
Schadt et al.

(10) Patent No.: US 10,095,066 B2
(45) Date of Patent: Oct. 9, 2018

(54) CINNAMIC ACID DERIVATIVE, POLYMER THEREOF, AND LIQUID CRYSTAL ALIGNMENT LAYER COMPRISING CURED PRODUCT THEREOF

(71) Applicant: DIC CORPORATION, Tokyo (JP)

(72) Inventors: Martin Schadt, Seltisberg (CH); Sayaka Nose, Kitaadachi-gun (JP); Yutaka Nagashima, Kitaadachi-gun (JP); Isa Nishiyama, Kitaadachi-gun (JP); Haruyoshi Takatsu, Kitaadachi-gun (JP)

(73) Assignee: DIC CORPORATION, Tokyo (JP)

( * ) Notice: Subject to any disclaimer, the term of this patent is extended or adjusted under 35 U.S.C. 154(b) by 196 days.

(21) Appl. No.: 15/168,849

(22) Filed: May 31, 2016

(65) Prior Publication Data

US 2016/0274418 A1     Sep. 22, 2016

Related U.S. Application Data

(62) Division of application No. 14/129,848, filed as application No. PCT/JP2012/066294 on Jun. 26, 2012, now Pat. No. 9,360,708.

(30) Foreign Application Priority Data

Jun. 30, 2011  (JP) ................. 2011-146043

(51) Int. Cl.
| | |
|---|---|
| *G02F 1/1337* | (2006.01) |
| *C07D 207/452* | (2006.01) |
| *C08F 22/40* | (2006.01) |
| *C07C 69/734* | (2006.01) |
| *C09K 19/56* | (2006.01) |
| *C08F 122/20* | (2006.01) |
| *C08F 122/40* | (2006.01) |
| *C09K 19/04* | (2006.01) |

(52) U.S. Cl.
CPC ...... *G02F 1/133711* (2013.01); *C07C 69/734* (2013.01); *C07D 207/452* (2013.01); *C08F 22/40* (2013.01); *C08F 122/20* (2013.01); *C08F 122/40* (2013.01); *C09K 19/56* (2013.01); *C07C 2601/02* (2017.05); *C07C 2601/08* (2017.05); *C07C 2601/14* (2017.05); *C09K 2019/0448* (2013.01); *G02F 2001/133738* (2013.01); *G02F 2001/133742* (2013.01); *Y10T 428/1005* (2015.01)

(58) Field of Classification Search
CPC ............. G02F 1/1337; G02F 1/133711; G02F 1/133723; G02F 1/13378; C09K 19/56; C09K 2019/0448; Y10T 428/1005; Y10T 428/1018; Y10T 428/1023; C07D 207/452; C07C 69/734; C07C 2101/02; C07C 2101/12; C07C 2101/14; C07C 2101/16
USPC ....... 428/1.2, 1.25, 1.26; 526/262, 313, 321, 526/319, 326, 328; 548/547; 560/61
See application file for complete search history.

(56) References Cited

U.S. PATENT DOCUMENTS

| | | |
|---|---|---|
| 4,830,952 A | 5/1989 | Penner et al. |
| 6,107,427 A | 8/2000 | Herr et al. |
| 2006/0051524 A1 | 3/2006 | Gibbons et al. |

FOREIGN PATENT DOCUMENTS

| | | |
|---|---|---|
| JP | 01-160637 A | 6/1989 |
| JP | 05-232473 A | 9/1993 |
| JP | 06-287457 A | 10/1994 |
| JP | 09-118717 A | 5/1997 |
| JP | 11-507941 A | 7/1999 |
| JP | 2002-517605 A | 6/2002 |
| JP | 2003-148647 | 5/2003 |
| JP | 2003-149647 A | 5/2003 |
| JP | 2005-148118 A | 6/2005 |
| JP | 2010-275244 A | 12/2010 |
| WO | 97/00851 A1 | 1/1997 |

OTHER PUBLICATIONS

International Search Report dated Oct. 2, 2012, application No. PCT/JP2012/066294.
Extended European Search Report dated Jun. 3, 2015, issued in counterpart application No. 12804748.7. (8 pages).
Komatsu, et al. "Effects of Protic Solvents upon Intramolecular Interaction of Polymethylene Bis-p-phenylenediacrylates" Tetrahedron Letter vol. 39 No. 51 (pp. 9451-9454) (1998).
Weissflog, et al. "Mesomorphic Behavior of New Double Swallow-Tailed Compounds" Advanced Materials vol. 8 No. 1 (pp. 76-79) (1996).

*Primary Examiner* — Ruiyun Zhang
(74) *Attorney, Agent, or Firm* — Westerman, Hattori, Daniels & Adrian, LLP

(57) ABSTRACT

Provided is a liquid crystal alignment layer of which a constituent member is a compound represented by the general formula (I).

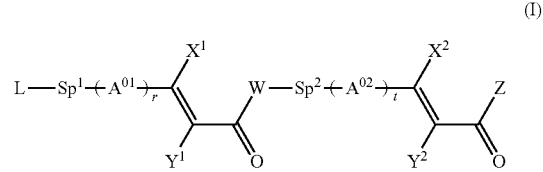

(I)

10 Claims, No Drawings

CINNAMIC ACID DERIVATIVE, POLYMER THEREOF, AND LIQUID CRYSTAL ALIGNMENT LAYER COMPRISING CURED PRODUCT THEREOF

CROSS-REFERENCE TO RELATED APPLICATIONS

This application is a divisional of U.S. application Ser. No. 14/129,848, filed on Dec. 27, 2013, which is a 371 of International Application No. PCT/JP2012/066294, filed on Jun. 26, 2012, which is based upon and claims the benefit of priority from the prior Japanese Patent Application No. 2011-146043, filed on Jun. 30, 2011, the entire contents of which are incorporated herein by reference.

TECHNICAL FIELD

The present invention relates to a compound, a polymer, a liquid crystal alignment layer, a liquid crystal display element, and an optical anisotropic body.

The present application claims priority on Japanese Patent Application No. 2011-146043, filed on Jun. 30, 2011, the contents of which are hereby incorporated herein by reference.

BACKGROUND ART

An alignment layer for aligning a liquid crystal is important for keeping the order of alignment of the liquid crystals and realizing optical characteristics based on refractive index anisotropy of liquid crystal molecules, and is an essential compositional member that constitutes a liquid crystal display element. Alignment of the liquid crystals significantly affects display characteristics of liquid crystal display elements, and thus various methods for aligning the liquid crystal have been investigated. The liquid crystal display elements can be broadly classified into two types, that is, a vertical alignment type and a horizontal alignment type.

A liquid crystal display device (sometimes referred to as a VA mode liquid crystal display device) using a liquid crystal layer of a vertical alignment type has been widely used in displays for its excellent display characteristics such as high contrast. However, since it cannot be said that the liquid crystal display device using a liquid crystal layer of a vertical alignment type necessarily has sufficient viewing angle characteristics, various methods have been investigated to improve the viewing angle characteristics. As a method for improving the viewing angle characteristics, a multi-domain vertical alignment mode (MVA mode) (incorporating an alignment division structure therein) has become prevalent, which forms a plurality of liquid crystal domains having different alignment directions in one pixel. In the MVA mode, it is necessary to control the tilt alignment of the liquid crystal molecules in order to form the alignment division structure, and as such a method, a method in which a slit (opening) or a rib (projection structure) is provided in electrodes, is used. However, with the use of the slit or the rib, the slit or the rib is linear unlike a case where a pretilt direction is defined by inserting liquid crystal molecules into two alignment films used in a TN mode used in the related art, and thus, the ability to control the alignment for the liquid crystal molecules becomes uneven within a pixel, whereby a problem of generation of a distribution in the response speeds arises.

In addition, there is another problem that a region provided with a slit or a rib exhibits decreased optical transmittance, resulting in a decrease in display luminance.

As another method for controlling the tilt alignment, there is disclosed a polymer sustained alignment (PSA) technology in which photo- or thermo-polymerizable monomers are incorporated into a liquid crystal, the monomers being polymerized while tilting the liquid crystal molecules by voltage application so that the tilt direction of the liquid crystal molecules is memorized (see PTL 1). This method can overcome the problem in the distribution of the response speeds or a decrease in the optical transmittance in the slit-and-rib method. However, this method faces problems such as changes in characteristics caused by the addition of monomers in the liquid crystal material, difficulty in controlling the process, and adverse effects of the residual monomers.

In order to avoid these problems, it is preferable even for the VA mode liquid crystal display device to form an alignment division structure by controlling the tilt alignment with an alignment film. As a method of providing an ability to control the tilt alignment on the vertical alignment film, there is a rubbing method, in which an alignment film made of a polyimide or the like is applied onto a substrate, and then the alignment film is rubbed with rubbing cloth to control the alignment direction and the pretilt angle. However, it is difficult to form a precise alignment division structure by the rubbing method, and thus problems of static electricity caused by friction and generation of impurities arise.

Meanwhile, as one of liquid crystal display devices using a liquid crystal layer of the horizontal alignment type, there is an IPS (In Plane Switching) mode liquid crystal display device. The IPS mode liquid crystal display device has little dependency on viewing angles such as in contrast and color tone, and is widely used in displays due to its excellent display characteristics. In the IPS mode, in order to reduce viewing angle dependency in the black display and the color reproducibility, a low pretilt angle of one degree or less on the electrode surface is required. Even when achieving the horizontal alignment, a rubbing method as a general alignment method is used. However, when a horizontal alignment treatment is carried out by a rubbing treatment with a polyimide alignment film, the pretilt angle provided to the liquid crystal molecules exceeds one degree, and thus, a problem that the display characteristics are deteriorated arises.

From these problems, in any alignment mode of the vertical alignment type and the horizontal alignment type, it is important to control the alignment direction and the pretilt angle using the alignment film so as to improve the display characteristics. As a method for controlling the tilt alignment with an alignment film, a photo-alignment method is known, in addition to the methods using rubbing treatment (see PTL 2). In the photo-alignment method, a precise alignment division structure can be formed easily by changing the illumination pattern of light, and static electricity or generation of impurities is difficult to occur, as compared with the rubbing treatment since a non-contact treatment on the alignment film can be carried out, and thus, it is expected to solve the above-described problems and to improve the display characteristics.

As the materials which can be a photo-alignment layer for the liquid crystal display element, a compound having a photochemically isomerizable site, such as an azobenzene derivative (see PTL 3), a compound having a photochemically crosslinkable site, such as a cinnamic acid derivative, a coumarin derivative, and a chalcone derivative (see PTLs 4, 5, and 6), a compound causing an anisotropic photo-degradation, such as a polyimide derivative, and the like are known.

However, the photo-alignment method using these compounds has a problem such as a low voltage holding ratio (VHR), as compared with a case using an ordinary alignment film. Therefore, various characteristics such as reliability, which allows realization of performance for controlling the tilt alignment of the liquid crystals and use in active matrix driving, are required, and photo-alignment layers for liquid crystals, which satisfy the requirements, have been demanded.

CITATION LIST

Patent Literature

[PTL 1] Japanese Unexamined Patent Application, First Publication No. 2003-149647

[PTL 2] Japanese Patent No. 2682771

[PTL 3] Japanese Unexamined Patent Application, First Publication No. H05-232473

[PTL 4] Japanese Unexamined Patent Application, First Publication No. H06-287453

[PTL 5] Japanese Unexamined Patent Application, First Publication No. H09-118717

[PTL 6] Japanese Unexamined Patent Application Publication (Translation of PCT Application) No. 2002-517605

SUMMARY OF INVENTION

Technical Problem

The present invention has an object to provide a liquid crystal alignment layer which is efficiently provided with an alignment property at a low irradiation dose of polarized light during the production, and has a superior ability to control the alignment of liquid crystals and the pretilt angles, and a high voltage holding ratio (VHR); a polymer used for the liquid crystal alignment layer; a compound constituting the polymer; a liquid crystal display element using the liquid crystal alignment layer; and an optical anisotropic body using the polymer.

Solution to Problem

The present inventors have made extensive studies on various materials in order to achieve the above object, and as a result, they have found that a liquid crystal alignment layer which is efficiently provided with an alignment property at a low irradiation dose of polarized light during the production, and has a superior ability to control the alignment of the liquid crystals and the pretilt angles, and a high voltage holding ratio (VHR) is obtained by applying a polymer obtained from a specific cinnamic acid derivative onto a substrate, and curing it, thereby leading to the completion of the present invention.

The compound of the present invention is a compound represented by the general formula (I).

[Chem. 1]

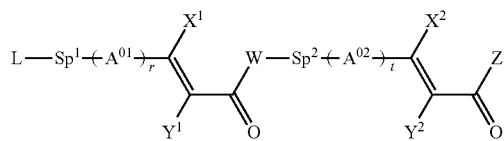

(I)

(in which L represents a polymerizable group and $Sp^1$ and $Sp^2$ each represent a spacer unit, $A^{01}$ and $A^{02}$ each independently represent a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH═'s present in this group may be substituted with —N═), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, $X^1$, $X^2$, $Y^1$ and $Y^2$ each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups may be substituted with —O—, —CO—O—, —O—CO— and/or —CH═CH—, Z is represented by the general formula (IIa) or (IIb):

[Chem. 2]

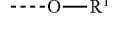

(IIa)

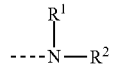

(IIb)

(in which the dashed line represents a bond to a carbon atom, to which Z is bonded, and $R^1$ and $R^2$ each independently represent a hydrogen atom or a linear or branched alkyl group having 1 to 30 carbon atoms, one —$CH_2$— group or two or more non-adjacent —$CH_2$— groups in $R^1$ and $R^2$ may be substituted with —O—, —CO—, —CO—O—, —O—CO—, —CO—NH—, —NH—CO—, —$NCH_3$—, —CH═CH—, —CF═CF—, and/or —C≡C—, one or two or more —$CH_2$— groups in $R^1$ and $R^2$ may be each independently substituted with a cycloalkyl group with a 3- to 8-membered ring, and a hydrogen atom in $R^1$ and $R^2$ may be substituted with an alkyl group having 1 to 20 carbon atoms, a cyano group, or a halogen atom), W represents —O— or —$NR^3$—, in which $R^3$ represents a hydrogen atom, a linear or branched alkyl group having 1 to 20 carbon atoms, or a cycloalkyl group with a 3- to 8-membered ring, which may have the alkyl group interposed therein as a linking group, a hydrogen atom in the alkyl group may be unsubstituted or may be substituted with a fluorine atom or a chlorine atom, a hydrogen atom in the cycloalkyl group may be unsubstituted or may be substituted with an alkyl group having 1 to 10 carbon atoms, an alkoxy group having 1 to 10 carbon atoms, a fluorine atom, or a chlorine atom, and r and t each independently represent 1 or 2).

The polymer of the present invention is a polymer constituted with a cured product of a composition including the compound according to the present invention, in which the cured product has a structural unit represented by the general formula (V).

[Chem. 3]

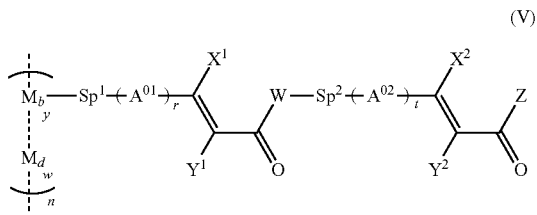

(V)

(in which $Sp^1$, $Sp^2$, $A^{01}$, $A^{02}$, $X^1$, $X^2$, $Y^1$, $Y^2$, W, Z, r, and t have the same definitions as in the general formula (I), $M_b$ and $M_d$ each represent a monomer unit of the polymer, y and w each represent a molar fraction of the copolymer, each satisfying $0<y\leq 1$ and $0\leq w<1$, n represents 4 to 100,000, the order in which $M_b$ and $M_d$ are arranged may be the same as or different from that shown in the formula, and the monomer units of $M_b$ and $M_d$ may be each independently constituted with one or two or more different units).

The liquid crystal alignment layer of the present invention is a liquid crystal alignment layer using the polymer according to the present invention.

The liquid crystal display element of the present invention is a liquid crystal display element using the liquid crystal alignment layer according to the present invention.

The optical anisotropic body of the present invention is an optical anisotropic body using the liquid crystal alignment layer according to the present invention.

Advantageous Effects of Invention

By using the compound (cinnamic acid derivative) of the present invention and a polymer thereof, a liquid crystal alignment layer which has a superior ability to control the alignment of the liquid crystals and the pretilt angles, and a high voltage holding ratio (VHR) can be produced, which is efficiently provided with an alignment property at a low irradiation dose of polarized light. Since the liquid crystal alignment layer of the present invention has a high voltage holding ratio (VHR) with a superior ability to control the alignment of the liquid crystals and the pretilt angles, it can be used to efficiently produce a liquid crystal display element and a liquid crystal display device, each exhibiting excellent display quality and reliability. Further, the optical anisotropic body of the present invention is useful for the production of an optical anisotropy film that can be used in optical compensation or the like.

DESCRIPTION OF EMBODIMENTS (Embodiment of Cinnamic Acid Derivative)
Specifically, the cinnamic acid derivative of the present invention is preferably a structure represented by the general formula (I).

[Chem. 4]

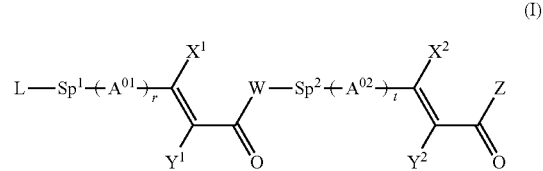

(I)

In the general formula (I), L represents a polymerizable group and $Sp^1$ and $Sp^2$ each represent a spacer unit, $A^{01}$ and $A^{02}$ each independently represent a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH═'s present in this group may be substituted with —N═), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group.

That is, $A^{01}$ and $A^{02}$ may each independently represent a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group, and these may be unsubstituted or one or more hydrogen atoms of these groups may be substituted with a fluorine atom, a chlorine atom, a methyl group, or a methoxy group.

$X^1$, $X^2$, $Y^1$ and $Y^2$ each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups in the alkyl group may be substituted with —O—, —CO—O—, —O—CO— and/or —CH═CH—.

Z is represented by the general formula (IIa) or (IIb), and r and t each independently represent 1 or 2).

[Chem. 5]

(IIa)

(IIb)

In the general formula (IIa) and (IIb), the dashed line represents a bond to a carbon atom, to which Z is bonded.

$R^1$ represents a hydrogen atom or a linear or branched alkyl group having 1 to 30 carbon atoms, preferably having 1 to 20 carbon atoms, or a cycloalkyl group with a 3- to 8-membered ring, which may have the alkyl group interposed therein as a linking group, a hydrogen atom in the alkyl group may be unsubstituted or may be substituted with a fluorine atom or a chlorine atom, a hydrogen atom in the cycloalkyl group may be unsubstituted or may be substituted with an alkyl group having 1 to 10 carbon atoms, an alkoxy group having 1 to 10 carbon atoms, a fluorine atom, or a chlorine atom.

That is, $R^1$ represents a linear or branched alkyl group having 1 to 30 carbon atoms, one —$CH_2$— group or two or more —$CH_2$— groups in $R^1$ may be each independently substituted with a cycloalkyl group with a 3- to 8-membered ring, and a hydrogen atom in $R^1$ may be substituted with an alkyl group having 1 to 20 carbon atoms, a cyano group, or a halogen atom.

$R^2$ represents a linear or branched alkyl group having 1 to 30 carbon atoms, or a cycloalkyl group with a 3- to 8-membered ring, which may have the alkyl group interposed therein as a linking group, a hydrogen atom in the alkyl group may be unsubstituted or may be substituted with a fluorine atom or a chlorine atom, and a hydrogen atom in the cycloalkyl group may be unsubstituted or may be substituted with an alkyl group having 1 to 10 carbon atoms, an alkoxy group having 1 to 10 carbon atoms, a fluorine atom, or a chlorine atom.

That is, $R^2$ represents a linear or branched alkyl group having 1 to 30 carbon atoms, one —$CH_2$— group or two or more —$CH_2$— groups in $R^2$ may be each independently substituted with a cycloalkyl group with a 3- to 8-membered ring, and a hydrogen atom in $R^2$ may be substituted with an alkyl group having 1 to 20 carbon atoms, a cyano group, or a halogen atom.

$R^1$ is preferably a linear or branched alkyl group having 1 to 30 carbon atoms, in which one —$CH_2$— group or two or more —$CH_2$— groups in $R^1$ may be each independently substituted with a cycloalkyl group with a 3- to 8-membered ring.

$R^2$ is preferably a linear or branched alkyl group having 1 to 30 carbon atoms, in which one —$CH_2$— group or two or more —$CH_2$— groups in $R^2$ may be each independently substituted with a cycloalkyl group with a 3- to 8-membered ring.

In the present specification and claims, "two or more non-adjacent $CH_2$ groups" means "two or more $CH_2$ groups that are not adjacent to each other".

In the general formula (I), (IIa), or (IIb), in order to improve the liquid crystal alignment properties of the liquid crystal alignment layer of the present invention, $A^{01}$ and/or $A^{02}$ is/are preferably a pyridine-2,5-diyl group, a pyrimidine-2,5-diyl group, or a 1,4-phenylene group.

Further, in order to improve the solubility of the polymer of the present invention, $A^{01}$ and/or $A^{02}$ is/are preferably a 1,4-naphthylene group, a 2,6-naphthylene group, a 2,5-thiophenylene group, or a 2,5-furanylene group.

Further, in order to reduce the light irradiation dose required for aligning the liquid crystal in the liquid crystal alignment layer of the present invention, $A^{01}$ and/or $A^{02}$ is/are preferably a pyridine-2,5-diyl group, a pyrimidine-2,5-diyl group, a 2,5-thiophenylene group, or a 1,4-phenylene group.

Further, in order to realize photo-alignment at a longer wavelength in the liquid crystal alignment layer of the present invention, $A^{01}$ and/or $A^{02}$ is/are preferably a pyrimidine-2,5-diyl group, a 2,5-thiophenylene group, a 2,6-naphthylene group, or a 2,5-furanylene group, and at least one selected from $X^1$, $X^2$, $Y^1$ and $Y^2$ is preferably a fluorine atom, a chlorine atom, or a cyano group.

Further, in order to improve the voltage holding ratio in the liquid crystal alignment layer of the present invention, $X^1$, $X^2$, $Y^1$ and $Y^2$ are each preferably a hydrogen atom, and $R^2$ are each preferably a linear or cyclic alkyl group having 1 to 12 carbon atoms.

In addition, in order to reduce the residual charges in the liquid crystal alignment layer of the present invention, $R^2$ is preferably a linear or cyclic alkyl group having 1 to 6 carbon atoms.

In the compound represented by the general formula (I) of the present invention, $X^1$, $X^2$, $Y^1$ and $Y^2$ are each preferably a hydrogen atom. Thus, the voltage holding ratio in the liquid crystal alignment layer of the present invention using the polymer obtained by using the compound can be improved.

A preferable compound of the present invention is the compound of the general formula (I), in which $A^{01}$ represents a 1,4-phenylene group having one or more hydrogen atoms which may be substituted with a fluorine atom, a chlorine atom, a methyl group, or a methoxy group.

By using the compound, a liquid crystal alignment layer, and a display element using the composition, each of which is efficiently provided with an alignment property at a low irradiation dose of polarized light during the production of the liquid crystal alignment layer, a superior ability to control the alignment of the liquid crystals and the pretilt angles, and a high voltage holding ratio (VHR), can be obtained.

A preferable compound of the present invention is the compound of the general formula (I), in which $A^{02}$ represents a 1,4-phenylene group having one or more hydrogen atoms which may be substituted with a fluorine atom, a chlorine atom, a methyl group, or a methoxy group.

By using the compound, a liquid crystal alignment layer, and a display element using the composition, each of which is efficiently provided with an alignment property at a low irradiation dose of polarized light during the production of the liquid crystal alignment layer, a superior ability to control the alignment of the liquid crystals and the pretilt angles, and a high voltage holding ratio (VHR), can be obtained.

In the compound represented by the general formula (I) of the present invention, $A^{01}$ and/or $A^{02}$ is/are preferably a 1,4-phenylene group which may have one or more hydrogen atoms substituted with a fluorine atom, a chlorine atom, a methyl group, or a methoxy group, and $A^{01}$ and $A^{02}$ are more preferably a 1,4-phenylene group which has one or more hydrogen atoms substituted with a fluorine atom, a chlorine atom, a methyl group, or a methoxy group.

By using the compound, a liquid crystal alignment layer, and a display element using the composition, each of which has a superior ability to control the alignment of the liquid crystals and the pretilt angles, and a high voltage holding ratio (VHR), can be obtained.

Since the compounds represented by the general formula (I) have a polymerizable substituent in the compound, the compounds can be polymerized with each other. As the polymerizable substituent, specifically, in the general formula (I), L is preferably any substituent selected from the group consisting of the general formulae (III-1) to (III-17), and among these, the general formula (III-1), (III-2), (III-6), (III-7), or (III-13) is preferable, and the general formula (III-1) or (III-2) is more preferable.

[Chem. 6]

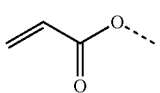 (III-1)

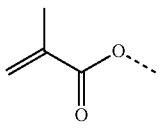 (III-2)

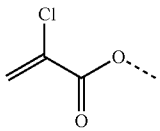 (III-3)

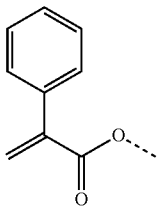 (III-4)

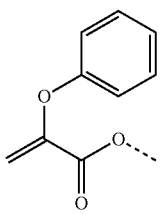 (III-5)

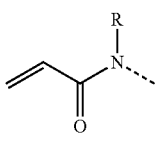 (III-6)

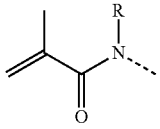 (III-7)

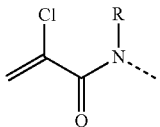 (III-8)

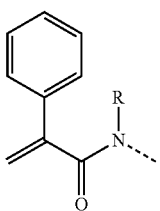 (III-9)

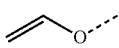 (III-10)

-continued

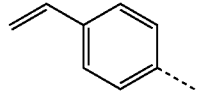 (III-11)

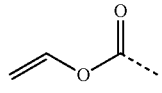 (III-12)

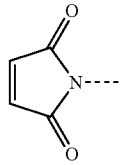 (III-13)

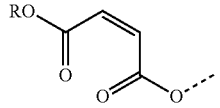 (III-14)

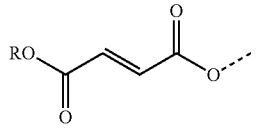 (III-15)

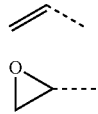 (III-16)

 (III-17)

(in which the dashed line represents a bond to $Sp^1$ and R's independently represent a hydrogen atom or an alkyl group having 1 to 5 carbon atoms).

In order to improve the solubility of the polymer of the present invention, the general formula (III-1), (III-2), (III-3), (III-6), (III-7), (III-8), (III-10), (III-12), (III-14), (III-16), or (III-17) is preferable, and among these, the general formula (III-1), (III-2), (III-10), (III-12), or (III-17) is particularly preferable.

Incidentally, in order to improve the polymerization speed of the compound of the present invention, the general formula (III-3), (III-8), (III-10), (III-12), (III-13), (III-14), (III-15), (III-16), or (III-17) is preferable, and among these, the general formula (III-3), (III-8), (III-10), (III-12), or (III-17) is more preferable.

Furthermore, in order to attain a narrow distribution of molecular weights of the polymer of the present invention, the general formula (III-2), (III-10), (III-11), or (III-12) is preferable.

Moreover, in order to improve the alignment stability in the liquid crystal alignment layer of the present invention, the general formula (III-2), (III-4), (III-5), (III-7), (III-9), (III-13), (III-14), or (III-15) is preferable.

In addition, in order to improve the adhesion of the polymer of the present invention to a substrate, the general formula (III-1), (III-6), (III-7), (III-8), (III-9), (III-10), (III-12), (III-13), or (III-17) is preferable, and among these, the general formula (III-6), (III-7), (III-8), or (III-13) is particularly preferable.

For the molecular weight distribution of the polymer of the present invention, Mw/Mn is preferably from 1.2 to 6.0, and more preferably from 1.4 to 4.0.

The compound represented by the general formula (I) of the present invention is preferably a compound in which L is represented by the general formula (III-1), (III-2), (III-6), (III-7), or (III-13). By using the compound, the above-described effects can be obtained.

The compound represented by the general formula (I) of the present invention is preferably the compound, in which L is represented by the general formula (III-1) or (III-2).

By using the compound, a liquid crystal alignment layer, and a display element using and the composition, each of which has a superior ability to control the alignment of the liquid crystals and the pretilt angles and has effects such as a high voltage holding ratio (VHR), can be obtained.

In the general formula (I), $Sp^1$ and $Sp^2$ are each independently preferably a structure represented by the following general formula (IV):

[Chem. 7]

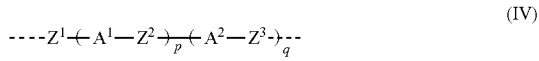

(IV)

(in which in $Sp^1$, the left dashed line represents a bond to L and the right dashed line represents a bond to $A^{01}$, and in $Sp^2$, the left dashed line represents a bond to W and the right dashed line represents a bond to $A^{02}$, in $Sp^1$ and $Sp^2$, $Z^1$, $Z^2$ and $Z^3$ each independently represent a single bond, $-(CH_2)_u-$ (in which u represents 1 to 20), $-OCH_2-$, $-CH_2O-$, $-COO-$, $-OCO-$, $-CH=CH-$, $-CF=CF-$, $-CF_2O-$, $-OCF_2-$, $-CF_2CF_2-$, or $-C\equiv C-$, but one or more of the non-adjacent $CH_2$ groups in these groups may be independently substituted with $-O-$, $-CO-$, $-CO-O-$, $-O-CO-$, $-Si(CH_3)_2-O-Si(CH_3)_2-$, $-NR-$, $-NR-CO-$, $-CO-NR-$, $-NR-CO-O-$, $-O-CO-NR-$, $-NR-CO-NR-$, $-CH=CH-$, $-C\equiv C-$, or $-O-CO-O-$ (in which R's independently represent hydrogen or an alkyl group having 1 to 5 carbon atoms), and $A^1$ and $A^2$ each independently represent a group selected from the group consisting of:

(a) a trans-1,4-cyclohexylene group (one methylene group or two or more non-adjacent methylene groups present in this group may be substituted with $-O-$, $-NH-$, or $-S-$), (b) a 1,4-phenylene group (one or two or more $-CH=$'s present in this group may be substituted with $-N=$), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, and p represents 0 or 1, and q represents 0, 1, or 2).

$A^1$ is preferably any group of a 1,4-naphthylene group, a 2,6-naphthylene group, a 2,5-thiophenylene group, or a 2,5-furanylene group, and one or more hydrogen atoms in such any group may be substituted with a fluorine atom, a chlorine atom, a methyl group, or a methoxy group.

$A^2$ is preferably any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group, and one or more hydrogen atoms in such any group may be substituted with a fluorine atom, a chlorine atom, a methyl group, or a methoxy group.

In the general formula (IV), $Z^1$, $Z^2$ and $Z^3$ are each independently preferably a single bond, $-(CH_2)_u-$ (in which u represents 1 to 20, one or more of the non-adjacent $CH_2$ groups may be independently substituted with $-O-$, $-CO-$, $-CO-O-$, $-O-CO-$, $-NR-$, $-NR-CO-$, $-CO-NR-$, $-NR-CO-NR-$, $-CH=CH-$, $-C\equiv C-$, or $-O-CO-O-$, and R represents hydrogen, a methyl group, or an ethyl group), $-OCH_2-$, $-CH_2O-$, $-COO-$, $-OCO-$, $-CH=CH-$, $-CF_2O-$, $-OCF_2-$, or $-C\equiv C-$.

In the general formula (IV), $Z^1$, $Z^2$ and $Z^3$ are each independently more preferably a single bond, $-(CH_2)_u-$ (in which u represents 1 to 20, and one or more of the non-adjacent $CH_2$ groups may be independently substituted with $-O-$, $-CO-O-$, $-O-CO-$, $-CH=CH-$, or $-C\equiv C-$), $-OCH_2-$, $-CH_2O-$, $-COO-$, $-OCO-$, $-CH=CH-$, or $-C\equiv C-$.

In the general formula (IV), $Z^1$, $Z^2$ and $Z^3$ are each independently particularly preferably a single bond, $-(CH_2)_u-$ (in which u represents 1 to 20, and one or more of the non-adjacent $CH_2$ groups may be independently substituted with $-O-$, $-CO-O-$, $-O-CO-$, $-CH=CH-$, or $-C\equiv C-$), $-OCH_2-$, $-CH_2O-$, $-COO-$, $-OCO-$, $-CH=CH-$, or $-C\equiv C-$.

Here, "one or more of the non-adjacent $CH_2$ groups" mean "one or more $CH_2$ groups that are not adjacent to each other".

In the general formula (IV), q is preferably 0.

In the general formula (IV), p is preferably 0.

In the general formula (IV), $A^1$ and $A^2$ are each independently preferably any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, or a 1,4-phenylene group. A hydrogen atom of these groups may be unsubstituted or one or more hydrogen atoms of these groups may be substituted with a fluorine atom, a chlorine atom, a methyl group, or a methoxy group.

In the general formula (IV), $A^1$ and $A^2$ are each independently more preferably any group of a trans-1,4-cyclohexylene group, a 2,6-naphthylene group, a pyridine-2,5-diyl group, a pyrimidine-2,5-diyl group, or a 1,4-phenylene group. A hydrogen atom of these groups may be unsubstituted or one or more hydrogen atoms of these groups may be substituted with a fluorine atom, a chlorine atom, a methyl group, or a methoxy group.

In the general formula (IV), $A^1$ and $A^2$ are each independently particularly preferably any group of a trans-1,4-cyclohexylene group, a 2,6-naphthylene group, or a 1,4-phenylene group. A hydrogen atom of these groups may be unsubstituted or one or more hydrogen atoms of these groups may be substituted with a fluorine atom, a methyl group, or a methoxy group.

In order to improve the liquid crystal alignment property in the liquid crystal alignment layer of the present invention, in the general formula (IV), $Z^1$, $Z^2$ and $Z^3$ are each independently preferably a single bond, $-(CH_2)_u-$ (in which u represents 1 to 8 and one or two of the non-adjacent $CH_2$ groups may be independently substituted with $-O-$, $-CO-O-$, $-O-CO-$, $-Si(CH_3)_2-O-Si(CH_3)_2-$, $-CH=CH-$, or $-C\equiv C-$), $-COO-$, $-OCO-$, $-CH=CH-$, $-CF=CF-$, or $-C\equiv C-$, and $A^1$ and $A^2$ are each independently preferably a trans-1,4-cyclohexylene group, a trans-1,3-dioxane-2,5-diyl group, a pyridine-2,5-diyl group, a pyrimidine-2,5-diyl group, a 2,5-thiophenylene group, or a 1,4-phenylene group.

Furthermore, in order to improve the thermal stability of the alignment in the liquid crystal alignment layer of the present invention, in the general formula (IV), $Z^1$, $Z^2$ and $Z^3$ are each independently preferably —NR—CO—, —CO—NR—, —NR—CO—O—, —O—CO—NR—, —NR—CO—NR—, or —O—CO—O—, $A^1$ and $A^2$ are each independently preferably a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group.

Moreover, in order to improve the solubility of the polymer of the present invention, $Z^1$, $Z^2$ and $Z^3$ are each independently preferably —OCH$_2$—, —CH$_2$O—, —CF$_2$O—, —OCF$_2$—, —CF$_2$CF$_2$—, —NR—, or —CO—, $A^1$ and $A^2$ are each independently preferably a trans-1,4-cyclohexylene group, a 1,4-naphthylene group, a 2,6-naphthylene group, or a 2,5-furanylene group.

In order to improve the ability to control the alignment of the liquid crystals and the pretilt angles in the liquid crystal alignment layer of the present invention and reduce the irradiation dose of polarized light to provide an alignment property during the production, in the general formula (IV), preferably, p and q are 0, $Z^1$ is —(CH$_2$)$_u$— (in which u represents 1 to 8, and one or two of the non-adjacent CH$_2$ groups may be independently substituted with —O—, —CO—O—, —O—CO—, —Si(CH$_3$)$_2$—O—Si(CH$_3$)$_2$—, —CH=CH—, —C≡C—), —COO—, —OCO—, —CH=CH—, —CF=CF—, or —C≡C—.

Sp$^1$ and Sp$^2$ represented by the general formula (IV) are each independently preferably, for example, those represented by the following chemical formulae (Sp-a-1) to (Sp-ad-9). Among these chemical formulae, the left dashed line represents a bond to L or a bond to W and the right dashed line represents a bond to $A^{o1}$ or a bond to $A^{o2}$.

Among these, those represented by the chemical formulae (Sp-a-6) to (Sp-a-16), the chemical formulae (Sp-b-3) to (Sp-b-10), the chemical formulae (Sp-c-3) to (Sp-c-10), the chemical formulae (Sp-d-3) to (Sp-d-12), the chemical formulae (Sp-k-4) to (Sp-k-7), the chemical formulae (Sp-1-13) to (Sp-1-17), the chemical formulae (Sp-o-3) to (Sp-o-14), the chemical formulae (Sp-p-2) to (Sp-p-13), the chemical formulae (Sp-s-1) to (Sp-s-8), the chemical formulae (Sp-t-1) to (Sp-t-8), the chemical formulae (Sp-y-1) to (Sp-y-9), and the chemical formulae (Sp-aa-1) to (Sp-aa-9) are more preferable.

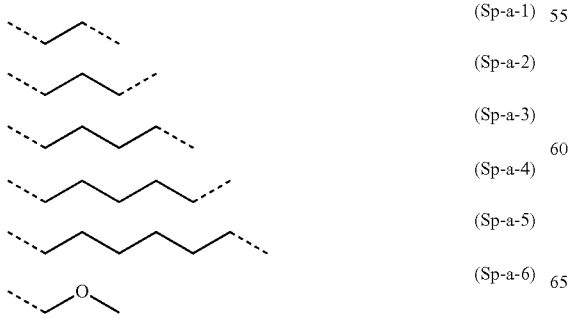

[Chem. 10]
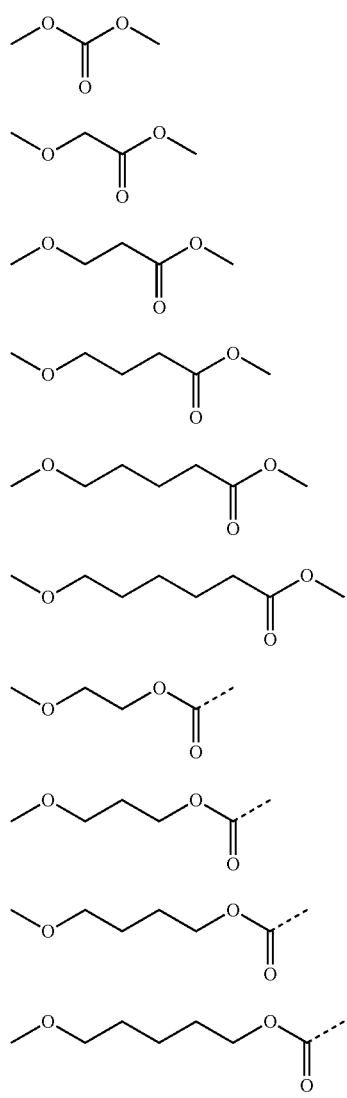
(Sp-c-1)
(Sp-c-2)
(Sp-c-3)
(Sp-c-4)
(Sp-c-5)
(Sp-c-6)
(Sp-c-7)
(Sp-c-8)
(Sp-c-9)
(Sp-c-10)
[Chem. 11]
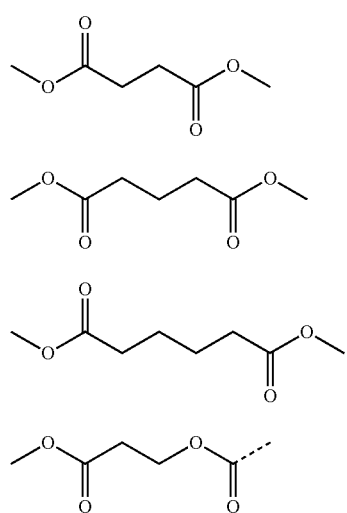
(Sp-d-1)
(Sp-d-2)
(Sp-d-3)
(Sp-d-4)
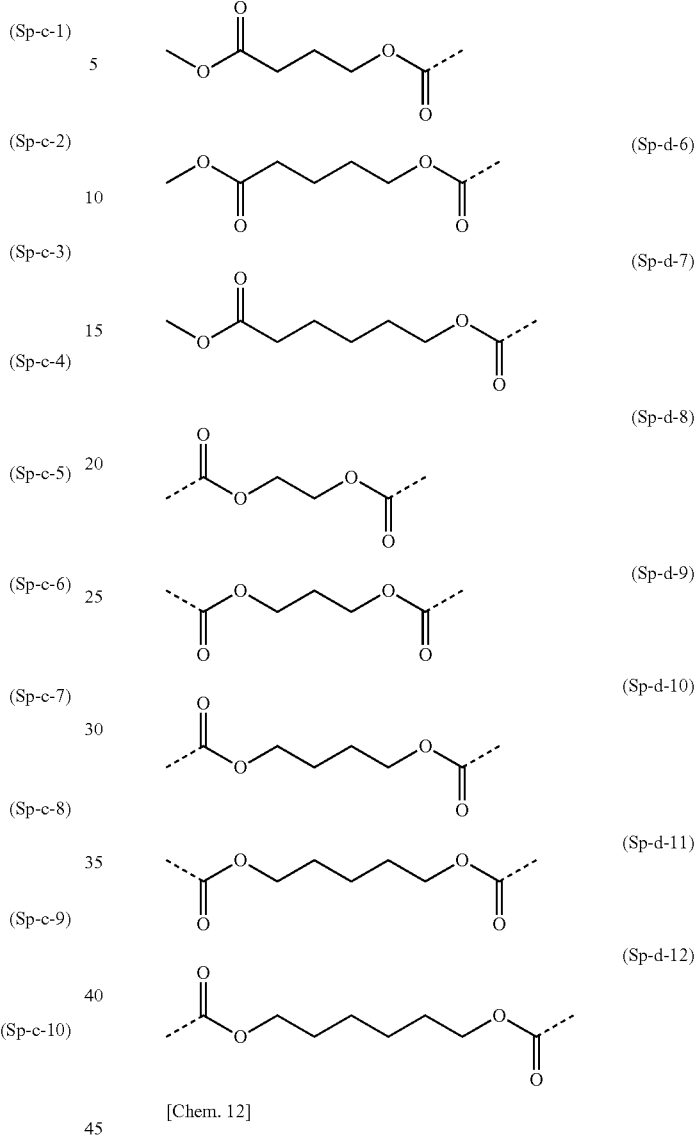
(Sp-d-5)
(Sp-d-6)
(Sp-d-7)
(Sp-d-8)
(Sp-d-9)
(Sp-d-10)
(Sp-d-11)
(Sp-d-12)
[Chem. 12]
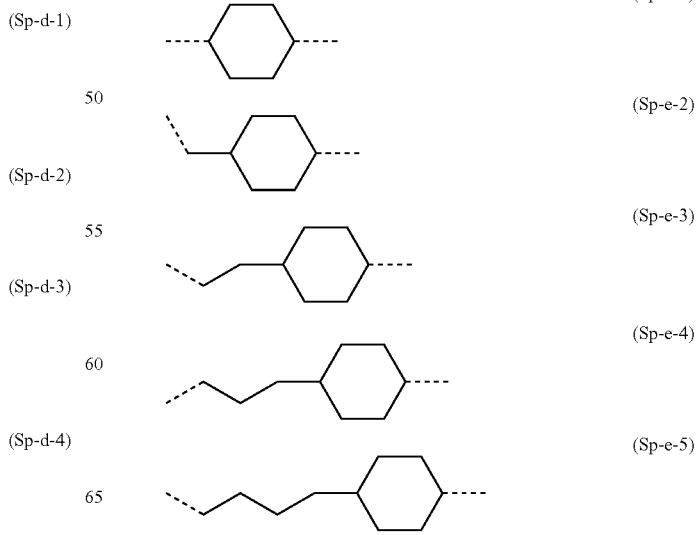
(Sp-e-1)
(Sp-e-2)
(Sp-e-3)
(Sp-e-4)
(Sp-e-5)

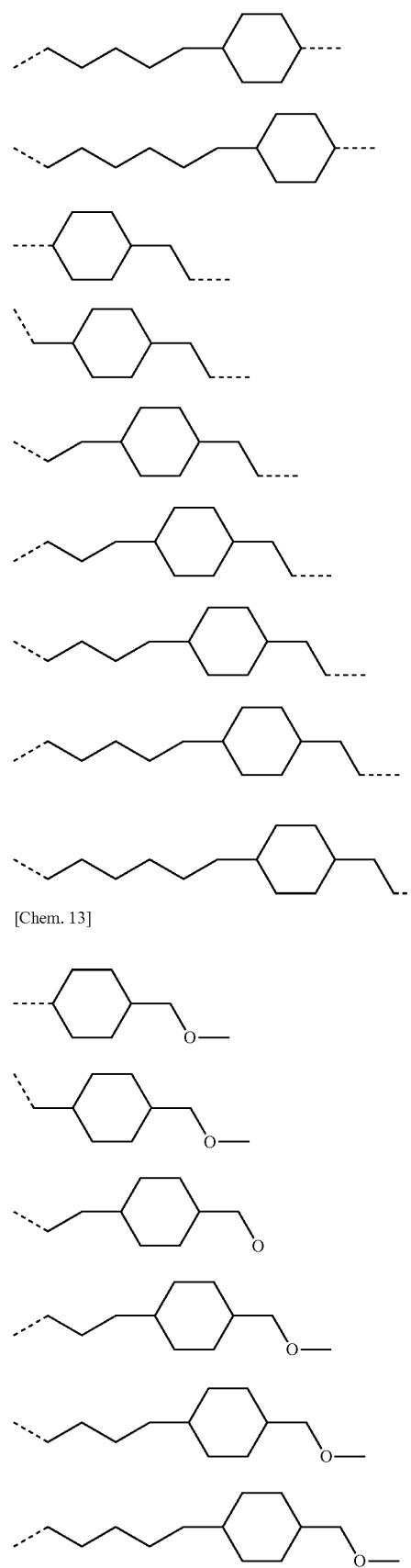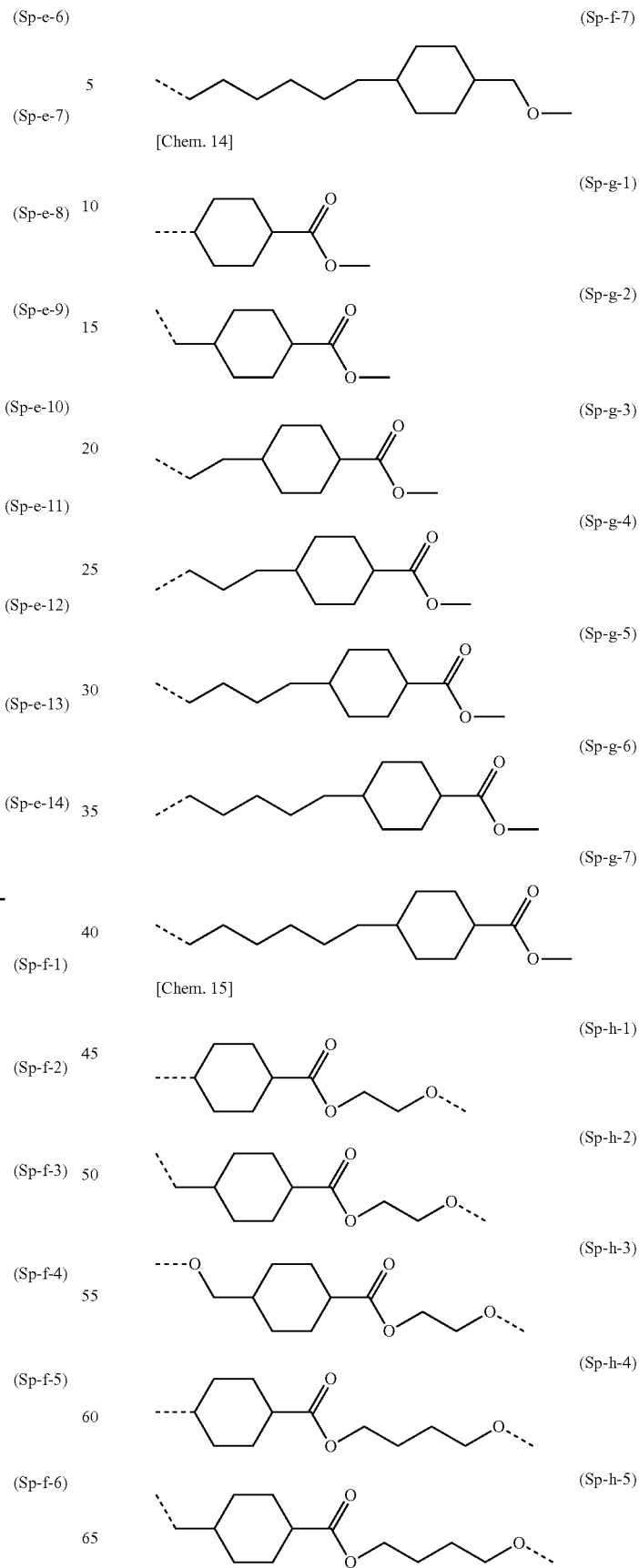

-continued
(Sp-h-6)
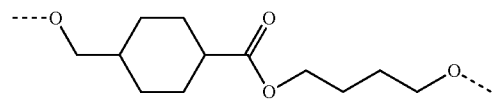
(Sp-h-7)
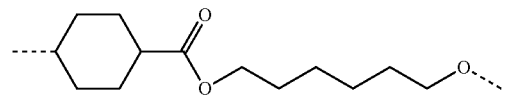
(Sp-h-8)
(Sp-h-9)
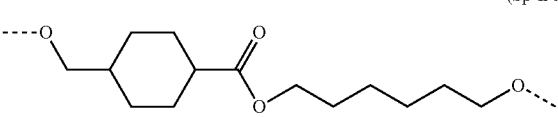
[Chem. 16]
(Sp-i-1)
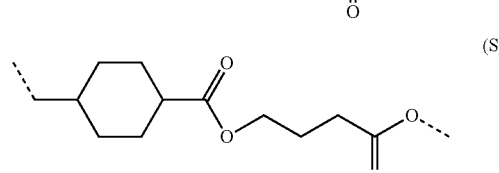
(Sp-i-2)
(Sp-i-3)
(Sp-i-4)
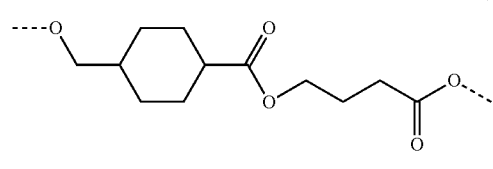
(Sp-i-5)
(Sp-i-6)
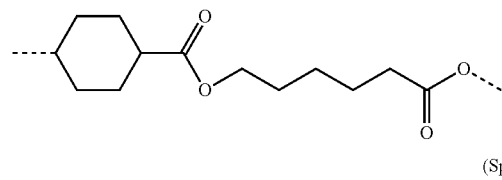
-continued
[Chem. 17]
(Sp-j-1)
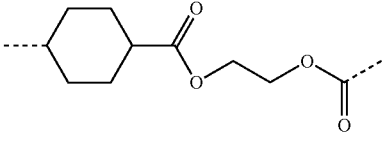
(Sp-j-2)
(Sp-j-3)
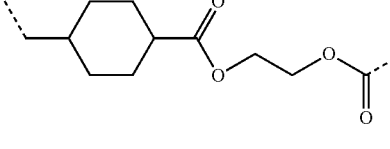
(Sp-j-4)
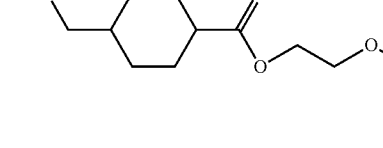
(Sp-j-5)
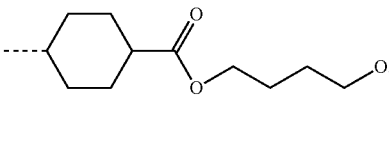
(Sp-j-6)
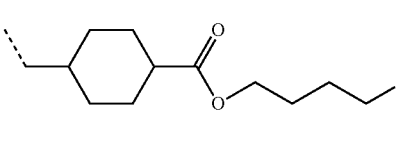
(Sp-j-7)
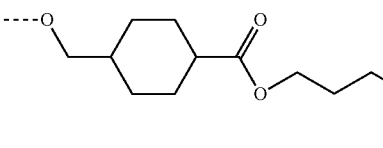
(Sp-j-8)
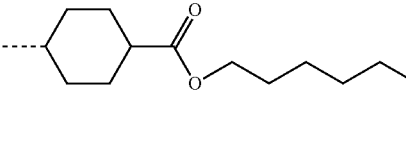
(Sp-j-9)
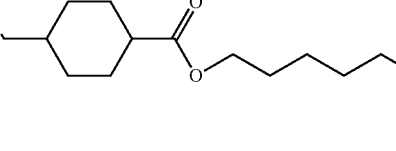

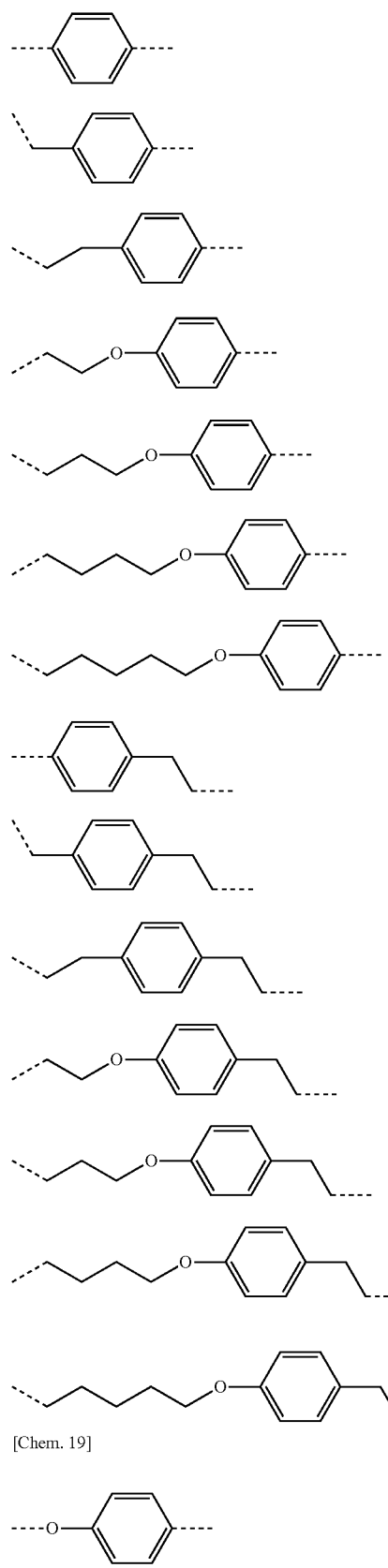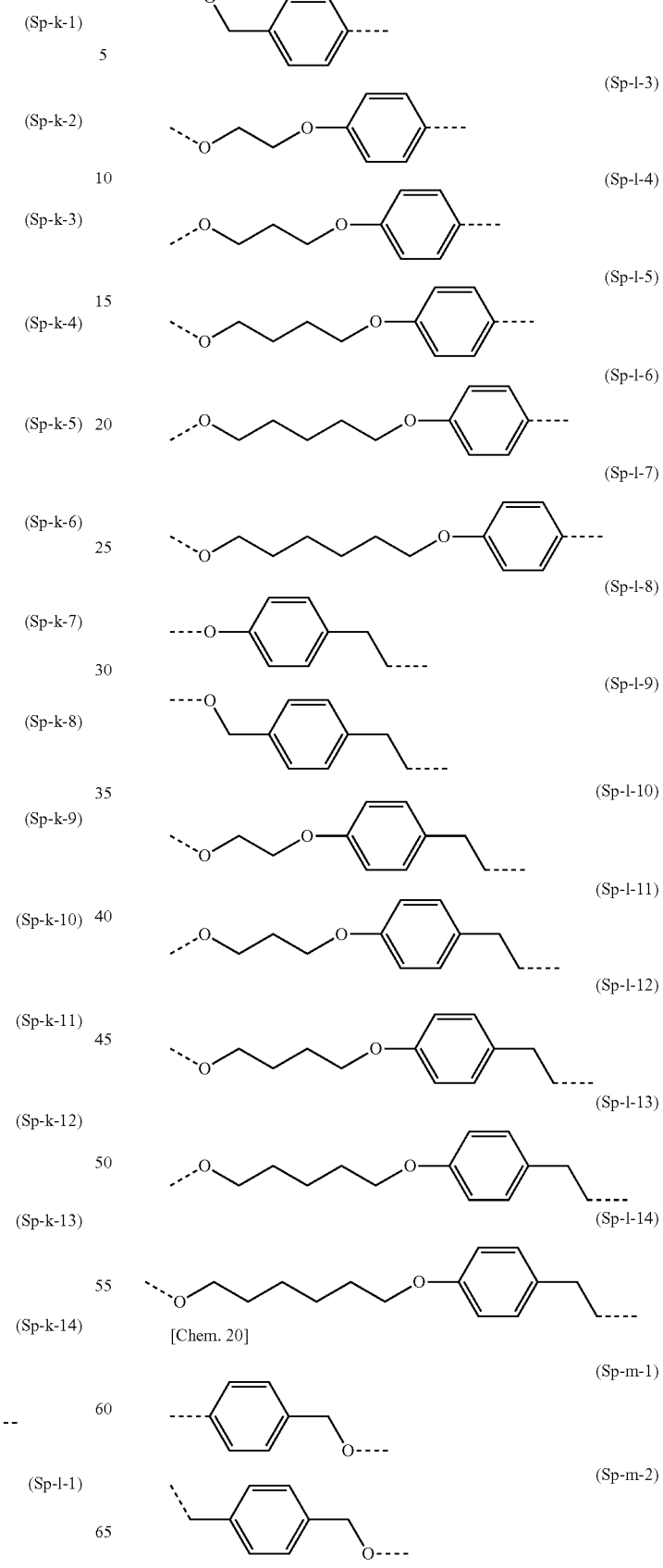

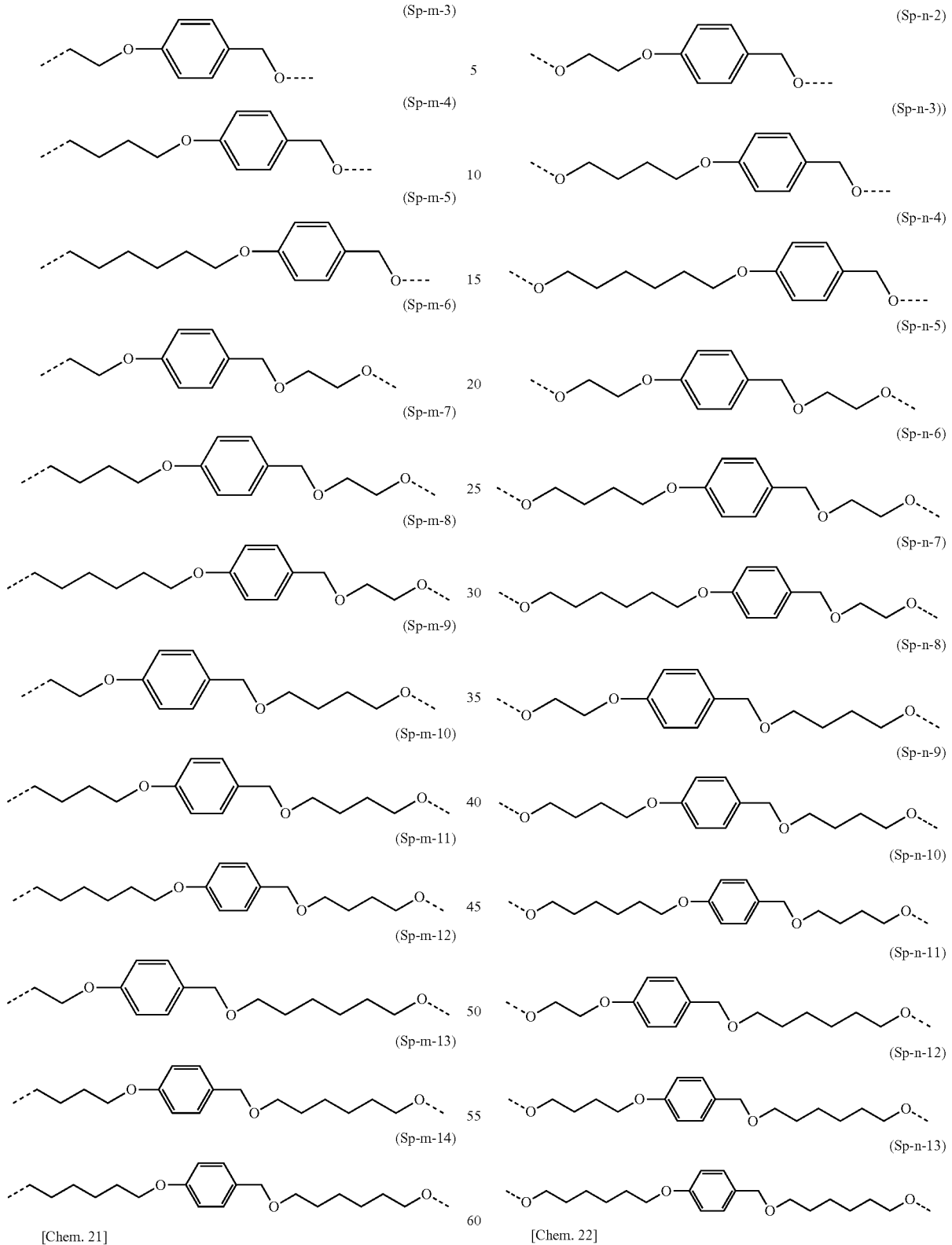
[Chem. 21]
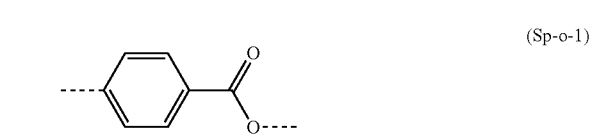

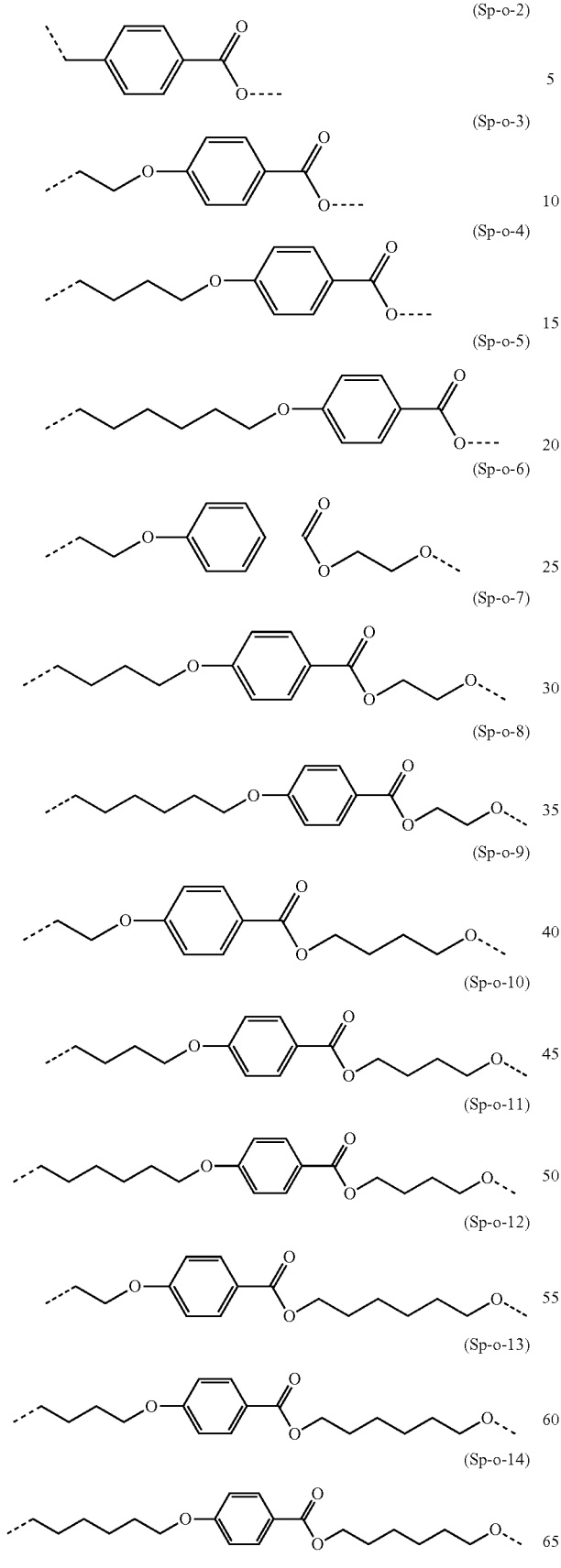
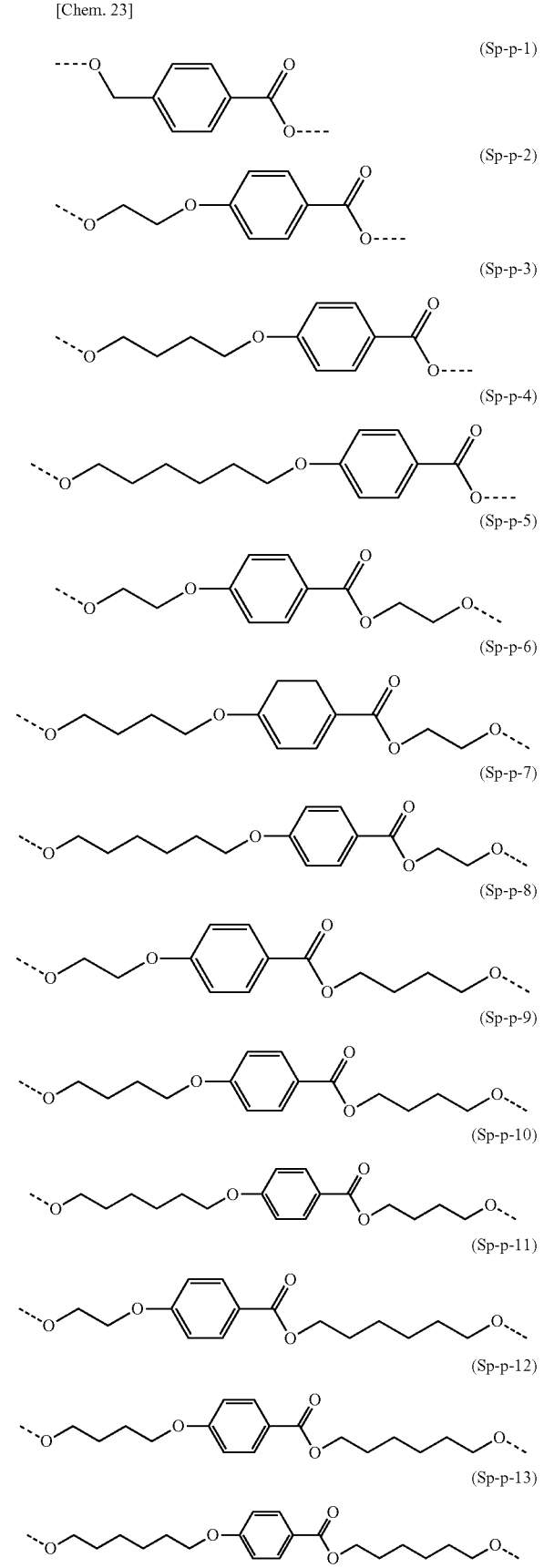

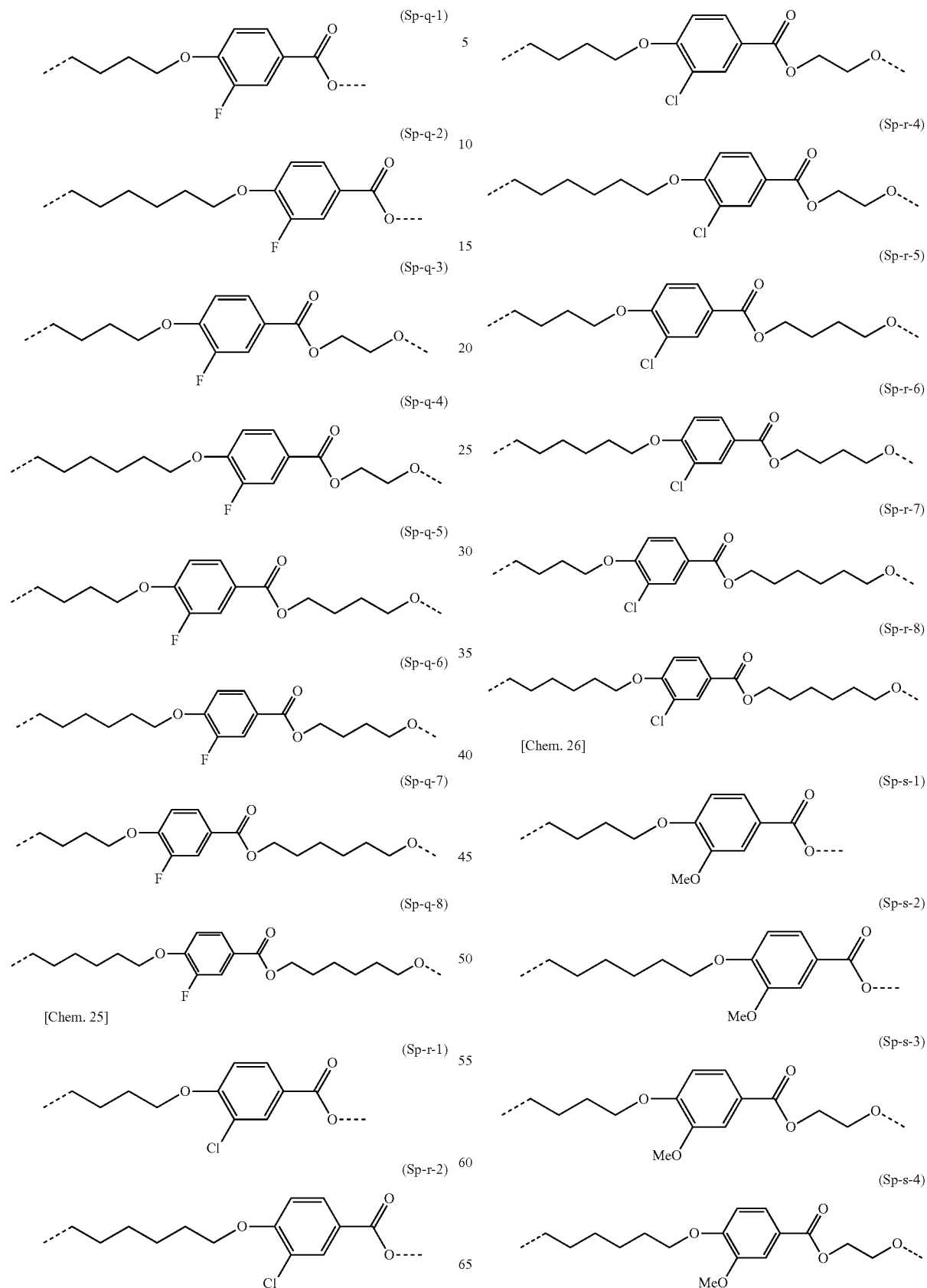

(Sp-s-5)
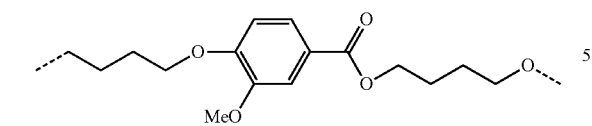
(Sp-s-6)
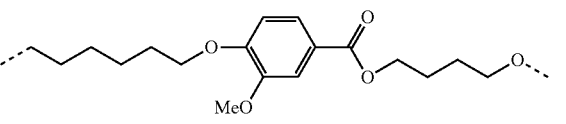
(Sp-s-7)
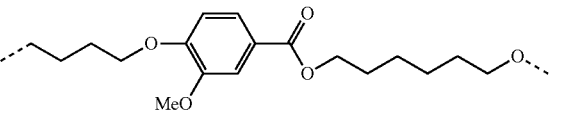
(Sp-s-8)
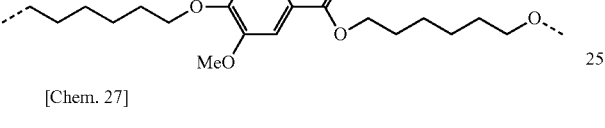
[Chem. 27]
(Sp-t-1)
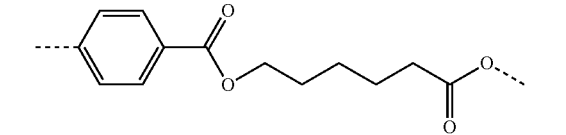
(Sp-t-2)
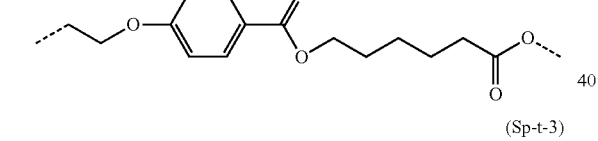
(Sp-t-3)
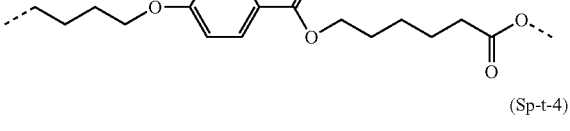
(Sp-t-4)
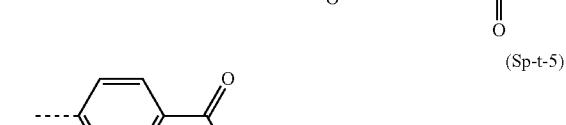
(Sp-t-5)
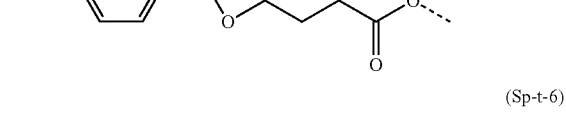
(Sp-t-6)
(Sp-t-7)
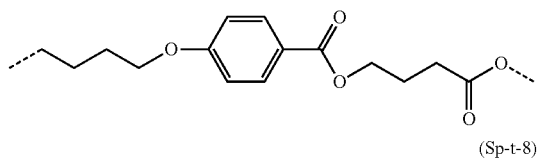
(Sp-t-8)
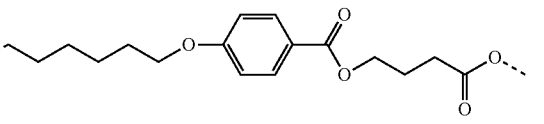
[Chem. 28]
(Sp-u-1)
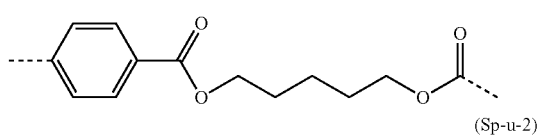
(Sp-u-2)
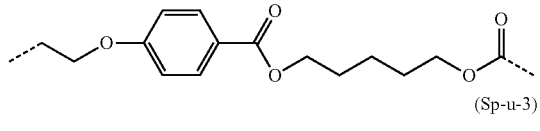
(Sp-u-3)
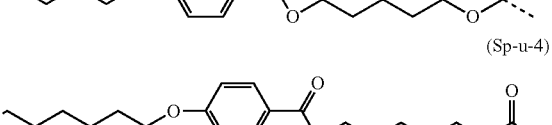
(Sp-u-4)
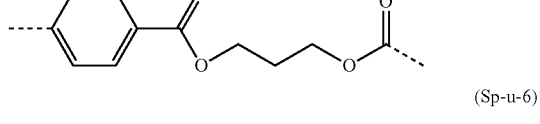
(Sp-u-5)
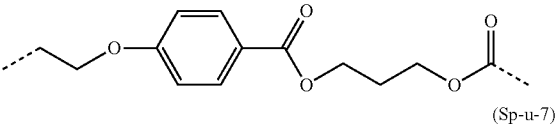
(Sp-u-6)
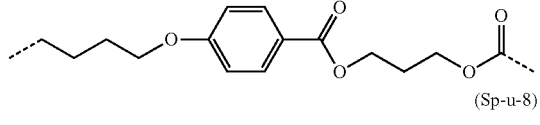
(Sp-u-7)
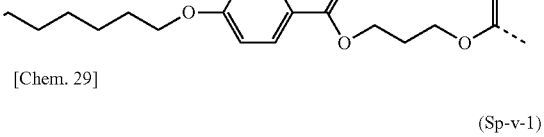
(Sp-u-8)
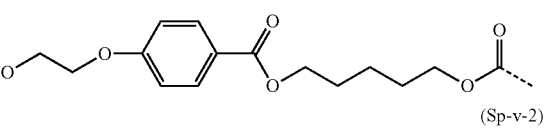
[Chem. 29]
(Sp-v-1)
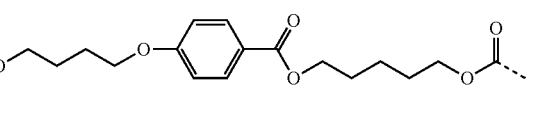
(Sp-v-2)
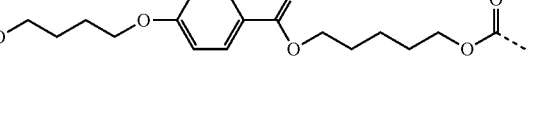

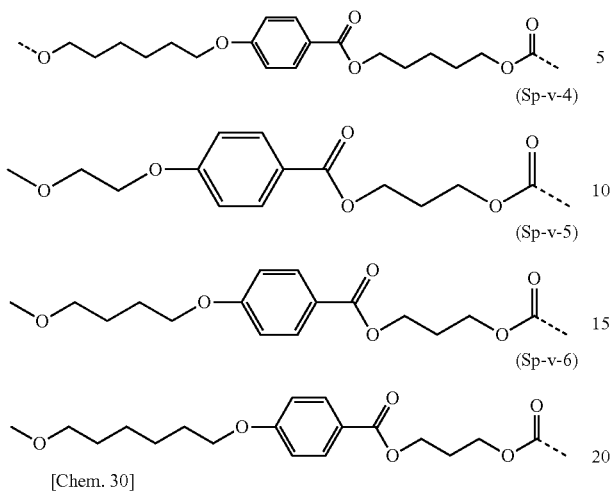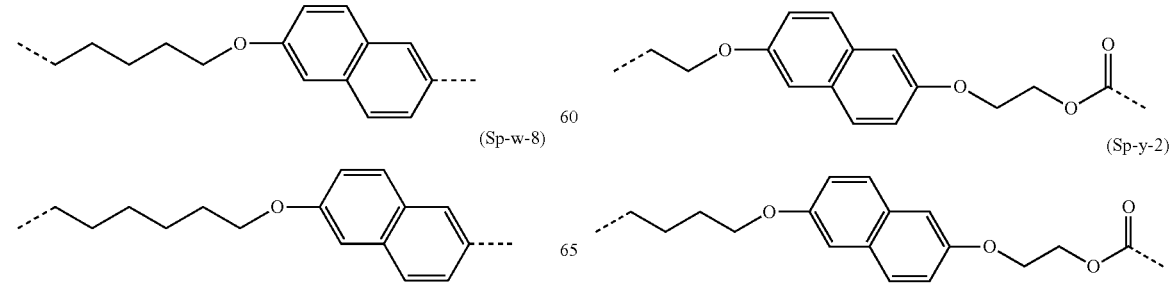

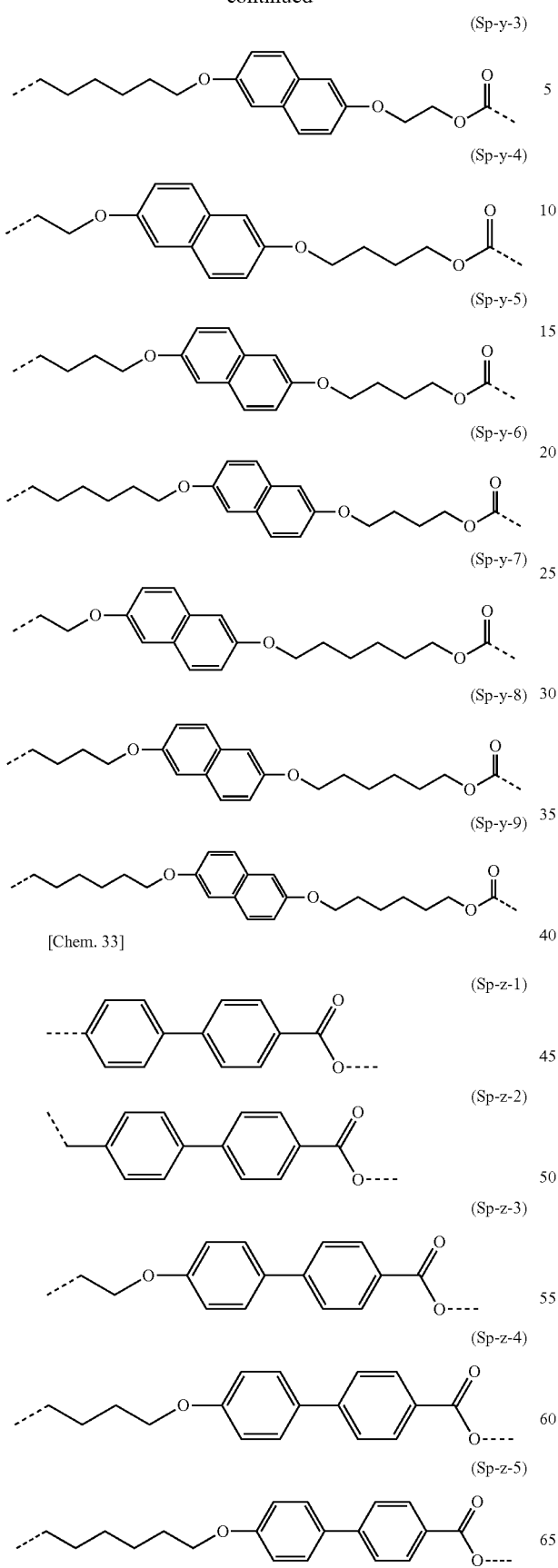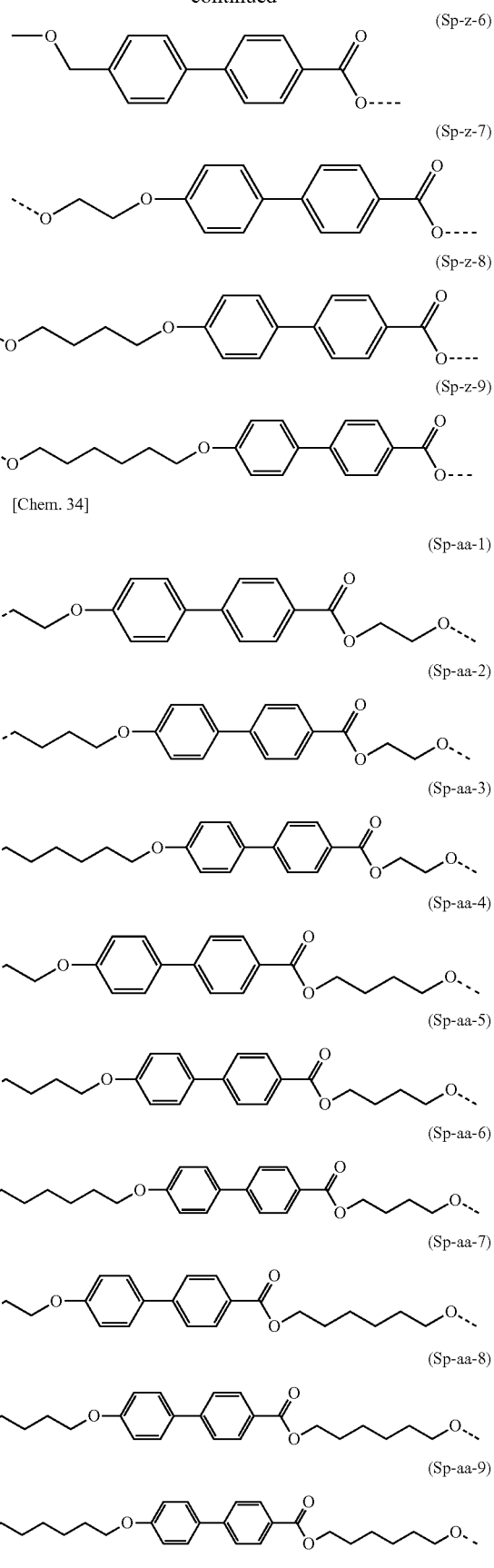

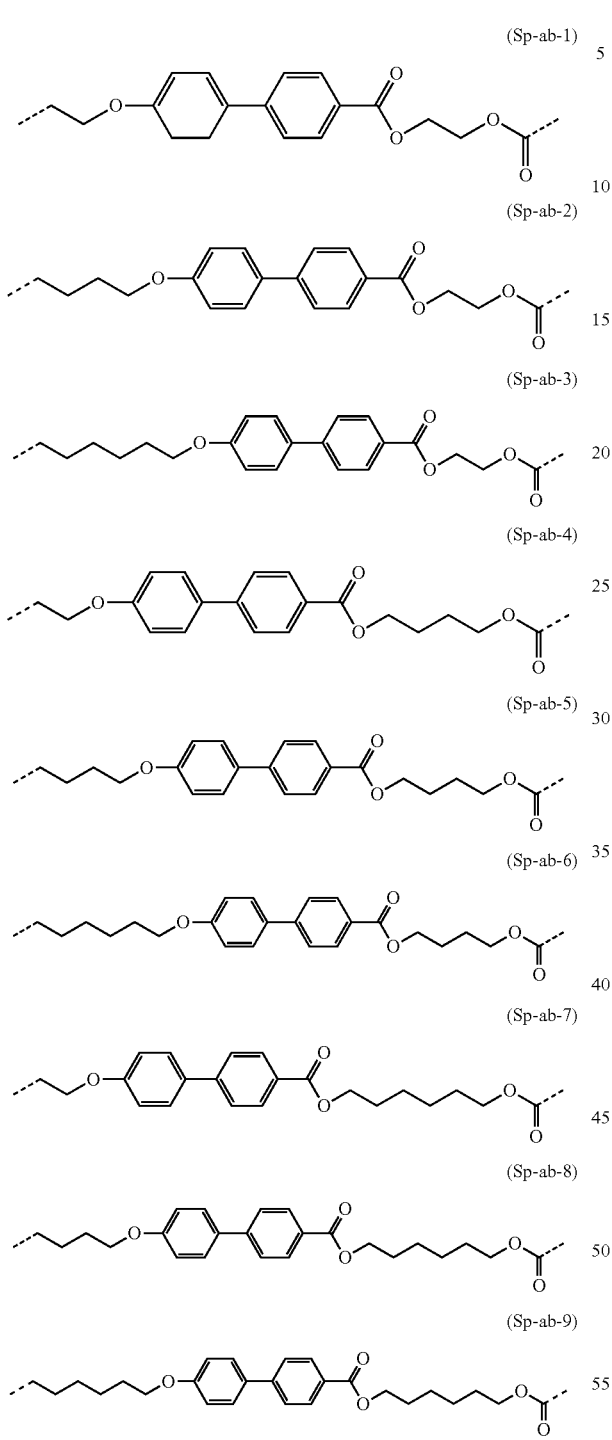
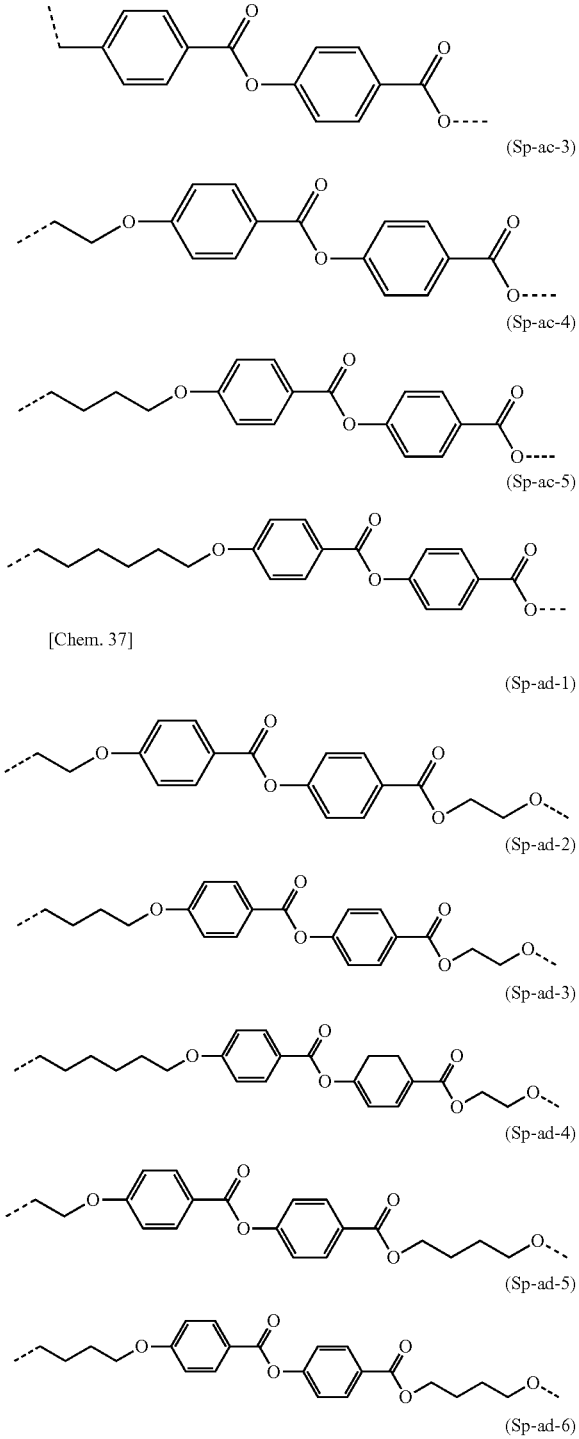

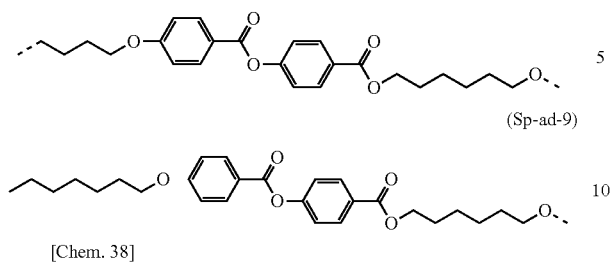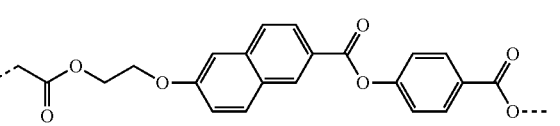

(Sp-ag-3)
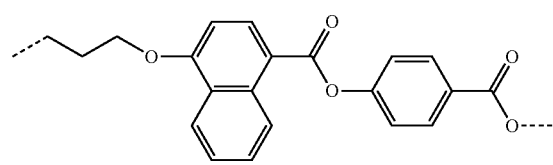

(Sp-ag-4)
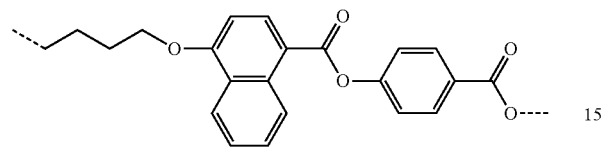

(Sp-ag-5)
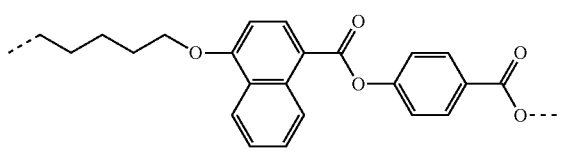

(Sp-ag-6)
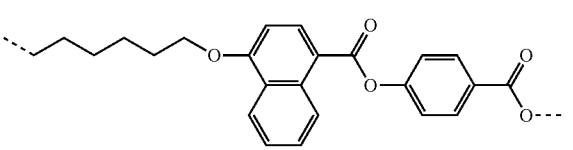

(Sp-ag-7)
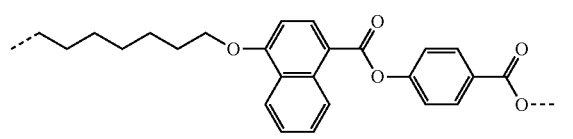

(Sp-ag-8)
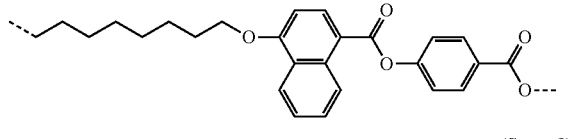

(Sp-ag-9)
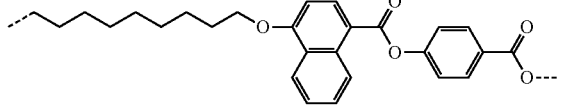

[Chem. 41]

(Sp-ah-1)
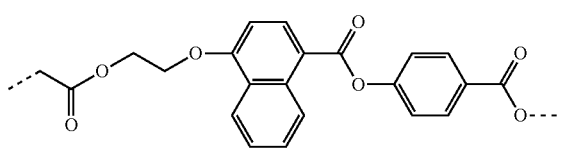

(Sp-ah-2)
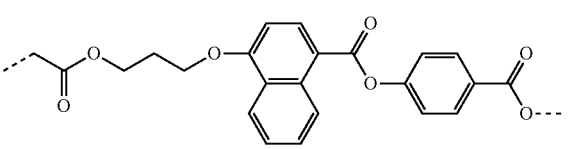

(Sp-ah-3)
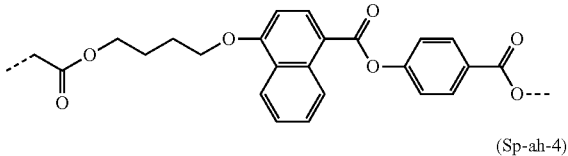

(Sp-ah-4)
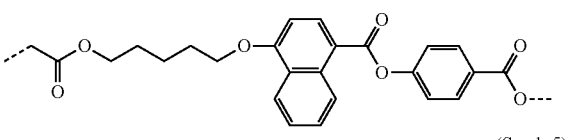

(Sp-ah-5)
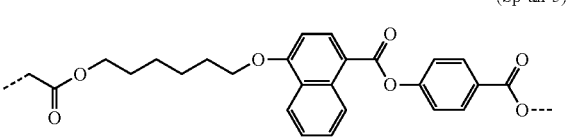

(Sp-ah-6)
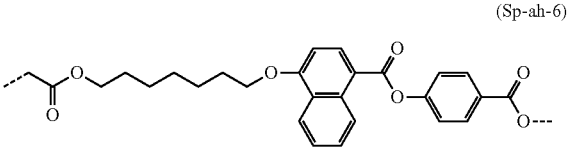

(Sp-ah-7)
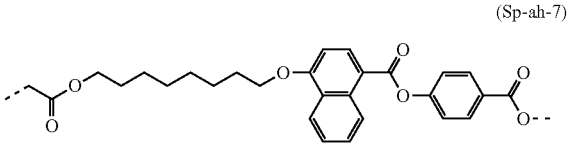

(Sp-ah-8)
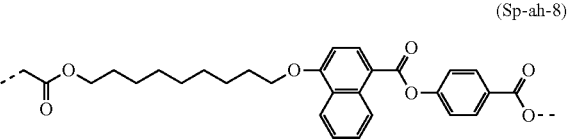

A preferable compound of the present invention is the compound of the general formula (I), in which Sp' represents a linear or branched alkylene group having 1 to 20 carbon atoms, or the alkylene group having one or more $CH_2$ groups which are not adjacent to each other substituted with —O— or —COO—.

By using the compound, a liquid crystal alignment layer, and a display element using the composition, each of which is efficiently provided with an alignment property at a low irradiation dose of polarized light during the production of the liquid crystal alignment layer, and has a superior ability to control the alignment of the liquid crystals and the pretilt angles, and a high voltage holding ratio (VHR), are obtained.

A preferable compound of the present invention is the compound of the general formula (I), in which $Sp^2$ represents a linear or branched alkylene group having 1 to 20 carbon atoms, or the alkylene group having one or more $CH_2$ groups which are not adjacent to each other substituted with —O— or —COO—.

By using the compound, a liquid crystal alignment layer, and a display element using the composition, each of which is efficiently provided with an alignment property at a low irradiation dose of polarized light during the production of the liquid crystal alignment layer, and has a superior ability to control the alignment of the liquid crystals and the pretilt angles, and a high voltage holding ratio (VHR), are obtained.

A preferable compound of the present invention is the compound having Sp¹ and Sp², each represented by the general formula (IV), in which p and q in the general formula (IV) are 0, and in Sp¹ and Sp², $Z^1$ is —$(CH_2)_u$— (in which u represents 1 to 8, and one or two of the non-adjacent $CH_2$ groups may be independently substituted with —O—, —CO—O—, —O—CO—, —Si$(CH_3)_2$—O—Si$(CH_3)_2$—, —CH=CH—, or —C≡C—), —COO—, —OCO—, —CH=CH—, —CF=CF—, or —C≡C—.

By using the compound, a liquid crystal alignment layer, and a display element using the composition, each of which is efficiently provided with an alignment property at a low irradiation dose of polarized light during the production of the liquid crystal alignment layer, and has a superior ability to control the alignment of the liquid crystals and the pretilt angles, and a high voltage holding ratio (VHR), are obtained.

A more preferable compound of the present invention is the compound having Sp¹ and Sp², each represented by the general formula (IV), in which p and q in the general formula (IV) are 0, and in both of Sp¹ and Sp², $Z^1$ is —$(CH_2)_u$— (in which u represents 1 to 8, and one or two of the non-adjacent $CH_2$ groups may be independently substituted with —O—, —CO—O—, —O—CO—, —Si$(CH_3)_2$—O—Si$(CH_3)_2$—, —CH=CH—, or —C≡C—).

By using the compound, a liquid crystal alignment layer, and a display element using the composition, each of which is efficiently provided with an alignment property at a low irradiation dose of polarized light during the production of the liquid crystal alignment layer, and has a superior ability to control the alignment of the liquid crystals and the pretilt angles, and a high voltage holding ratio (VHR), are obtained.

(Embodiments of Polymer)

The liquid crystal alignment layer of the present invention is obtained by forming a layer of a polymer for a liquid crystal alignment layer on the surface of a substrate used for aligning the liquid crystal, and irradiating it with light to conduct crosslinking and/or isomerization. The liquid crystal alignment layer of the present invention is produced using a cured product of the cinnamic acid derivative or a composition containing the cinnamic acid derivative. The cured product is preferably a polymer having a structural unit represented by the following general formula (V). As specific embodiments or examples thereof, those described as follows are preferable.

[Chem. 42]

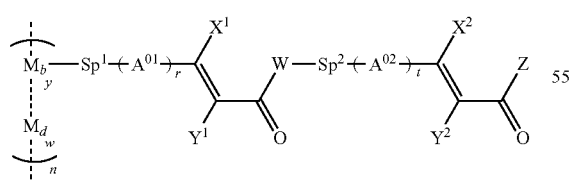

(V)

(in which Sp², Sp², $A^{01}$, $A^{02}$, $X^1$, $X^2$, $Y^1$, $Y^2$, W, Z, r, and t have the same definitions as in the general formula (I), $M_b$ and $M_d$ each represent a monomer unit of the polymer, y and w each represent a molar fraction of the copolymer, each satisfying $0<y\le 1$ and $0\le w<1$, n represents 4 to 100,000, the order in which $M_b$ and $M_d$ are arranged may be the same as or different from that shown in the formula, and the monomer units of $M_b$ and $M_d$ may be each independently constituted with one or two or more different units).

The polymer of the present invention can be preferably used to form a liquid crystal alignment layer for a horizontal alignment mode or vertical alignment mode liquid crystal display element, or to form a liquid crystal alignment layer for an optical anisotropic body. Further, the obtained liquid crystal alignment layer can be preferably used in the horizontal alignment mode or vertical alignment mode liquid crystal display element.

In the present specification and claims, the "monomer unit ($M_b$)" and the "monomer unit ($M_d$)" are sometimes abbreviated as "$M_b$" and "$M_d$", respectively.

In the general formula (V), a hydrogen atom of $M_b$ is substituted with Sp¹ and thus Sp¹ is bonded to $M_b$.

$M_b$ and $M_d$ may be the same as, except that Sp¹ is bonded to $M_b$, or different from each other and a known monomer unit can be used while not being particularly limited. Further, the sequencing order and randomness of the monomer units ($M_b$ and $M_d$) in the polymer are not particularly limited.

In addition, as $M_b$ and $M_d$, each independently, one kind of the monomer unit or combination of two or more kinds of the monomer units can be used. In this case, they are preferably used to a degree which does not interfere with the effects exerted by the polymer as a liquid crystal alignment film.

In the general formula (V), $M_b$ is preferably any one or more selected from the group consisting of the following general formulae (QIII-A-1) to (QIII-A-17).

[Chem. 43]

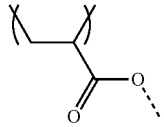

(QIII-A-1)

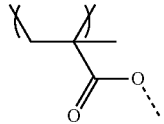

(QIII-A-2)

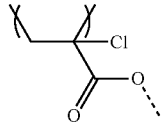

(QIII-A-3)

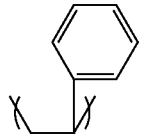

(QIII-A-4)

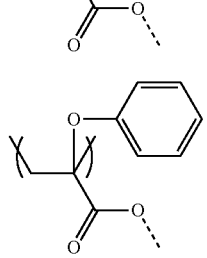

(QIII-A-5)

-continued (QIII-A-6) 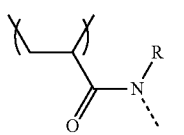

(QIII-A-7) 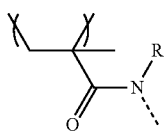

(QIII-A-8) 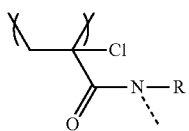

(QIII-A-9) 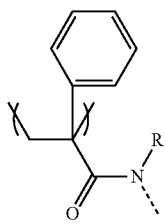

(QIII-A-10) 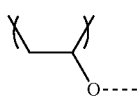

(QIII-A-11) 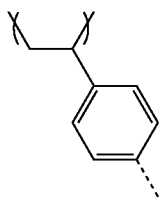

(QIII-A-12) 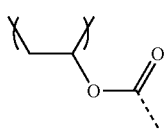

(QIII-A-13) 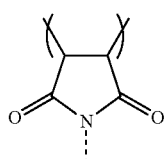

(QIII-A-14) 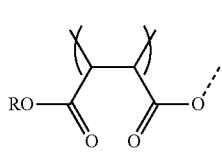

(QIII-A-15) 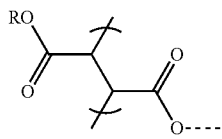

(QIII-A-16) 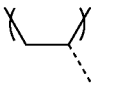

(QIII-A-17) 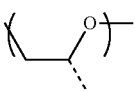

(in which the dashed line represents a bond to $Sp^1$, R's independently represent hydrogen or an alkyl group having 1 to 5 carbon atoms, and any hydrogen atom in each of the structures may be substituted with a fluorine atom, a chlorine atom, a methyl group, or a methoxy group).

In the general formula (V), $M_d$ is preferably any one or more selected from the group consisting of the following general formulae (QIII-1) to (QIII-17).

[Chem. 44]

(QIII-1) 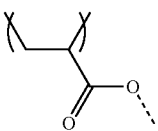

(QIII-2) 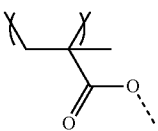

(QIII-3) 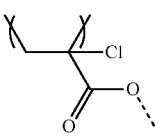

(QIII-4) 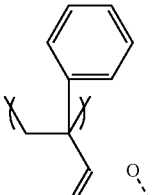

(QIII-5) 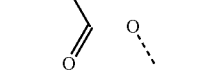

(QIII-6) 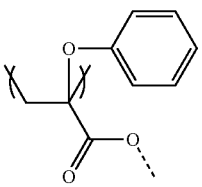

(QIII-7) 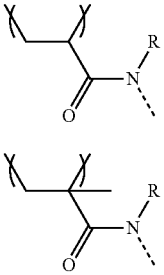

-continued

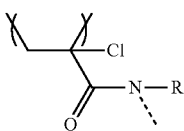
(QIII-8)

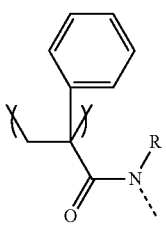
(QIII-9)

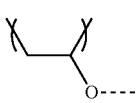
(QIII-10)

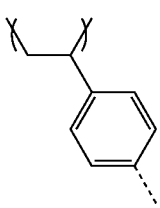
(QIII-11)

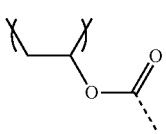
(QIII-12)

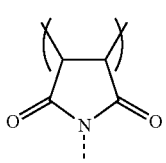
(QIII-13)

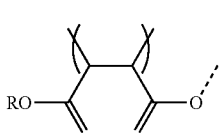
(QIII-14)

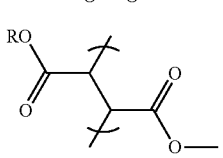
(QIII-15)

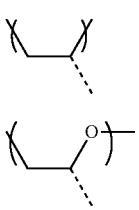
(QIII-16)

(QIII-17)

(in which the dashed line represents a bond to a hydrogen atom or a monovalent organic group, R's independently represent hydrogen or an alkyl group having 1 to 5 carbon atoms, and any hydrogen atom in each of the structures may be substituted with a fluorine atom, a chlorine atom, a methyl group, or a methoxy group).

Examples of the monovalent organic group include hydrogen, an alkyl group having 1 to 20 carbon atoms (any hydrogen atom in the alkyl group may be substituted with a fluorine atom, a chlorine atom, a methyl group, or a methoxy group, and one $CH_2$ group or two or more non-adjacent $CH_2$ groups in the alkyl group may be substituted with —O—, —CO—O—, —O—CO—, and/or —CH=CH—). For example, the number of carbon atoms of the alkyl group may be, for example, 1 to 10, if necessary, or may be, for example, 1 to 6 or 1 to 3.

Incidentally, examples of the monovalent organic group include a trans-1,4-cyclohexylene group, a trans-1,3-dioxan-2,5-yl group, a 1,4-naphthylene group, a 2,6-naphthylene group, a 2,5-pyridyl group, a 2,5-pyrimidyl group, a 2,5-thiophenylene group, a 2,5-furanylene group, or a 1,4-phenylene group (any hydrogen atom in each of the structures may be substituted with a fluorine atom, a chlorine atom, a methyl group, or a methoxy group).

Moreover, particularly, in order to obtain an alignment layer for vertical alignment, examples of the monovalent organic group include those of the general formula (QIV). That is, in the general formulae (QIII-1) to (QIII-17), the monovalent organic group may be represented by the general formula (QIV).

[Chem. 45]

$$-S_a-V_a \qquad (QIV)$$

(in which the dashed line represents a bond to a monomer unit ($M_d$), $S_a$ represents a spacer unit, and $V_a$ represents a moiety that stabilizes the vertical alignment).

As $S_a$, a spacer unit represented by the general formula (IV) as described above may be used.

$V_a$ is preferably a structure represented by the following general formula (VI).

[Chem. 46]

$$--(-A^3-Z^4)_{r1}(-A^4-Z^5)_{s1}(-A^5-Z^6)_{t1}(-A^6-Z^7)_{u1}-R^{12} \qquad (VI)$$

In the general formula (VI), the dashed line represents a bond to $S_a$, $Z^4$, $Z^5$, $Z^6$ and $Z^7$ each independently represent a single bond, —$(CH_2)_u$— (in which u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C— but one or more of the non-adjacent $CH_2$ groups in these substituents may be independently substituted with —O—, —CO—, —CO—O—, —O—CO—, —Si$(CH_3)_2$—O—Si$(CH_3)_2$—, —NR—, —NR—CO—, —CO—NR—, —NR—CO—O—, —O—CO—NR—, —NR—CO—NR—, —CH=CH—, —C≡C—, or —O—CO—O— (in which R's independently represent hydrogen or an alkyl group having 1 to 5 carbon atoms), $A^3$, $A^4$, $A^5$ and $A^6$ each independently represent a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH='s present in this group may be substituted with —N=), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one $CH_2$ group or two or more non-adjacent $CH_2$ groups in the alkyl group may be substituted with —O—, —CO—O—, —O—CO— and/or —CH=CH—)).

$Z^4$, $Z^5$, $Z^6$ and $Z^7$ are each independently preferably a single bond, —$(CH_2)_u$— (in which u represents 1 to 12, one or more of the non-adjacent $CH_2$ groups may be independently substituted with —O—, —CO—, —CO—O—, —O—CO—, —NR—CO—, —CO—NR—, —NR—CO—NR—, —CH=CH—, —C≡C—, or —O—CO—O—, and R's independently represent hydrogen, a methyl group, or an ethyl group), —$OCH_2$—, —$CH_2O$—, —COO—, —OCO—, —CH=CH—, —$CF_2O$—, —$OCF_2$—, or —C≡C—.

$A^3$, $A^4$, $A^5$ and $A^6$ each independently preferably represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group. $A^3$, $A^4$, $A^5$ and $A^6$ each independently preferably represent a trans-1,4-cyclohexylene group, a 2,6-naphthylene group, a pyridine-2,5-diyl group, a pyrimidine-2,5-diyl group, or a 1,4-phenylene group. Preferably, these groups are unsubstituted or have one or more hydrogen atoms substituted with a fluorine atom, a chlorine atom, a methyl group, or a methoxy group.

For r1, s1, t1, and u1, r1+s1+t1+u1 is preferably from 0 to 3.

$R^{12}$ is preferably a structure represented by hydrogen, fluorine, chlorine, a cyano group, or an alkyl group having 1 to 18 carbon atoms (one $CH_2$ group or two or more non-adjacent $CH_2$ groups in the alkyl group may be substituted with —O—, —CO—O—, —O—CO—, and/or —CH=CH—).

In order to improve the liquid crystal alignment property in the liquid crystal alignment layer of the present invention, $Z^4$, $Z^5$, $Z^6$ and $Z^7$ are each independently preferably a single bond, —$(CH_2)_u$— (in which u represents 1 to 8, and one or two of the non-adjacent $CH_2$ groups may be independently substituted with —O—, —CO—O—, —O—CO—, —Si$(CH_3)_2$—O—Si$(CH_3)_2$—, —CH=CH—, or —C≡C—), —COO—, —OCO—, —CH=CH—, —CF=CF—, or —C≡C— and $A^3$, $A^4$, $A^5$ and $A^6$ are each preferably a trans-1,4-cyclohexylene group, a trans-1,3-dioxane-2,5-diyl group, a pyridine-2,5-diyl group, a pyrimidine-2,5-diyl group, a 2,5-thiophenylene group, or a 1,4-phenylene group.

Moreover, in order to improve the thermal stability of alignment in the liquid crystal alignment layer of the present invention, $Z^4$, $Z^5$, $Z^6$ and $Z^7$ are each independently preferably —NR—CO—, —CO—NR—, —NR—CO—O—, —O—CO—NR—, —NR—CO—NR—, or —O—CO—O—, and $A^3$, $A^4$, $A^5$ and $A^6$ are each independently preferably a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group.

Furthermore, in order to improve the solubility of the polymer of the present invention, $Z^4$, $Z^5$, $Z^6$ and $Z^7$ are each independently preferably —$OCH_2$—, —$CH_2O$—, —$CF_2O$—, —$OCF_2$—, —$CF_2CF_2$—, —NR—, or —CO—, and $A^3$, $A^4$, $A^5$ and $A^6$ are each independently preferably a trans-1,4-cyclohexylene group, a 1,4-naphthylene group, a 2,6-naphthylene group, or a 2,5-furanylene group.

Furthermore, in order to provide a pretilt angle of 80 degrees or more to the liquid crystal alignment layer of the present invention, $Z^4$, $Z^5$, $Z^6$ and $Z^7$ are each independently preferably a single bond, —$OCH_2$—, —$CH_2O$—, —COO—, —OCO—, and —C≡C—, $A^3$, $A^4$, $A^5$ and $A^6$ are each independently preferably a trans-1,4-cyclohexylene group, a trans-1,3-dioxane-2,5-diyl group, or a 1,4-phenylene group, and $R^{12}$ is preferably an alkyl group having 1 to 20 carbon atoms, an alkoxy group, fluorine, a trifluoromethyl group, or a trifluoromethoxy group.

In the case of providing a pretilt angle of 80 degrees or more to the liquid crystal alignment layer of the present invention, as $V_a$ represented by the general formula (VI), for example, compounds represented by the following chemical formulae (VI-a-1) to (VI-q-10) are particularly preferable. Among these chemical formulae, the dashed line represents a bond to $S_a$.

Among these, the chemical formulae (VI-a-1) to (VI-a-15), the chemical formulae (VI-b-11) to (VI-b-15), the chemical formulae (VI-c-1) to (VI-c-11), the chemical formulae (VI-d-10) to (VI-d-15), the chemical formulae (VI-f-1) to (VI-f-10), the chemical formulae (VI-g-1) to (VI-g-10), the chemical formulae (VI-h-1) to (VI-h-10), the chemical formulae (VI-j-1) to (VI-j-9), the chemical formulae (VI-1-1) to (VI-1-11), or the chemical formulae (VI-m-1) to (VI-m-11) are more preferable.

[Chem. 47]

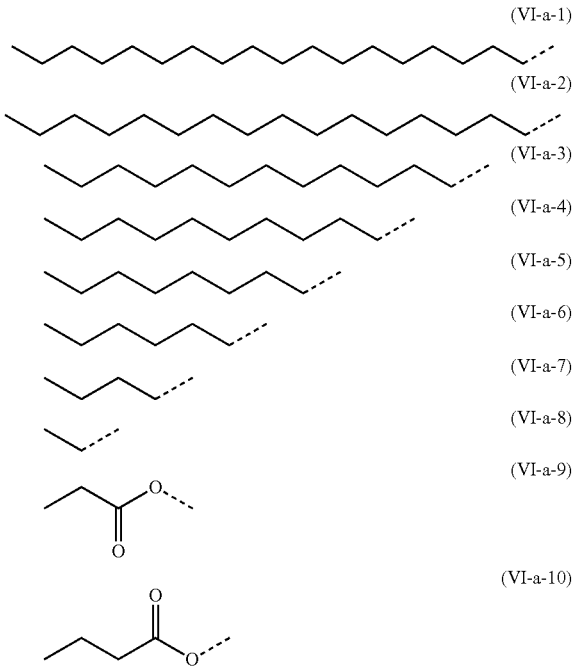

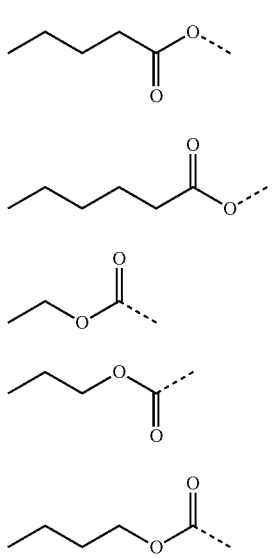
(VI-a-11)
(VI-a-12)
(VI-a-13)
(VI-a-14)
(VI-a-15)
[Chem. 48]
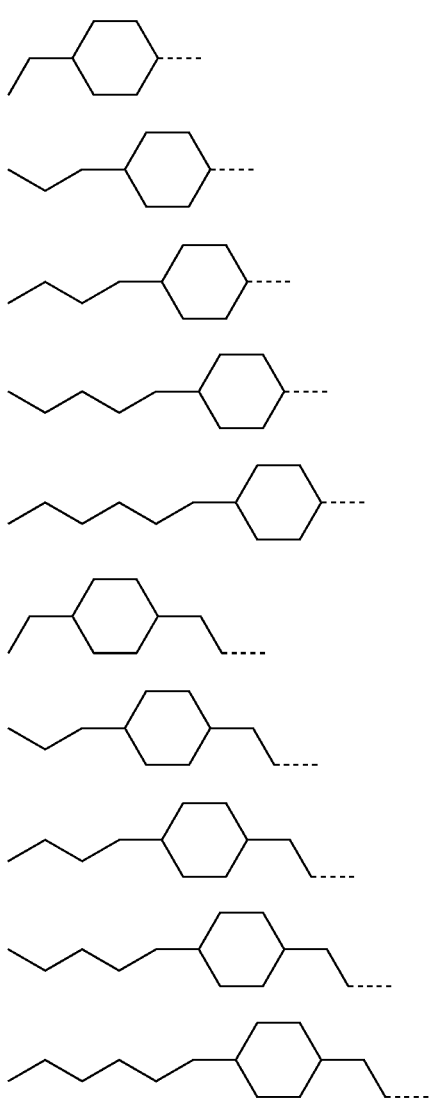
(VI-b-1)
(VI-b-2)
(VI-b-3)
(VI-b-4)
(VI-b-5)
(VI-b-6)
(VI-b-7)
(VI-b-8)
(VI-b-9)
(VI-b-10)
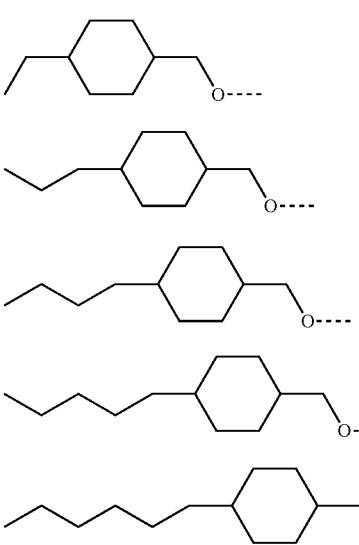
(VI-b-11)
(VI-b-12)
(VI-b-13)
(VI-b-14)
(VI-b-15)
[Chem. 49]
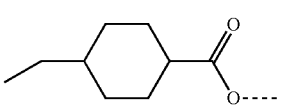 (VI-c-1)
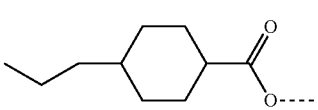 (VI-c-2)
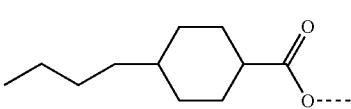 (VI-c-3)
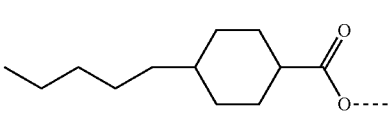 (VI-c-4)
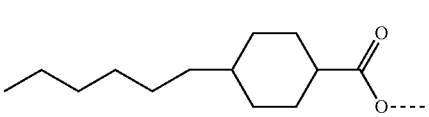 (VI-c-5)
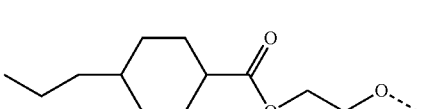 (VI-c-6)
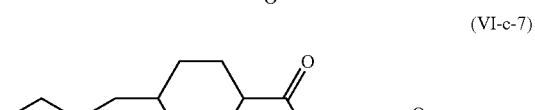 (VI-c-7)
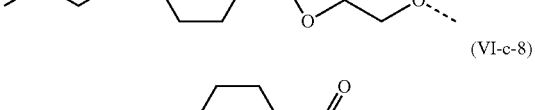 (VI-c-8)
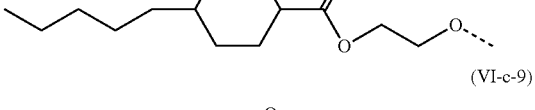 (VI-c-9)
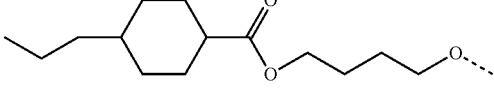

(VI-c-10)
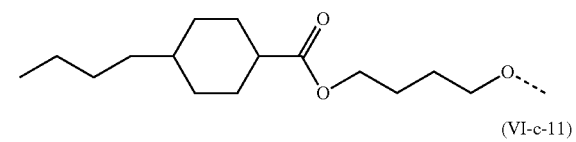
(VI-c-11)
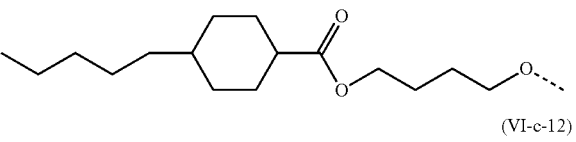
(VI-c-12)
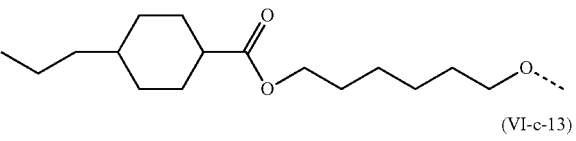
(VI-c-13)
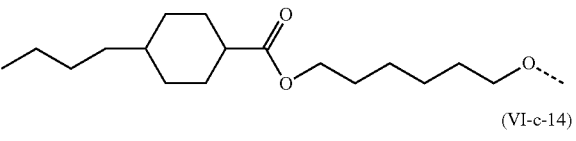
(VI-c-14)
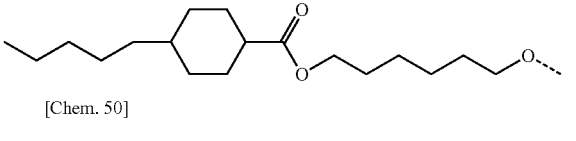
[Chem. 50]
(VI-d-1)
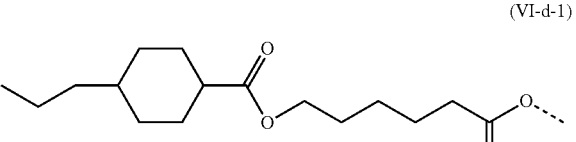
(VI-d-2)
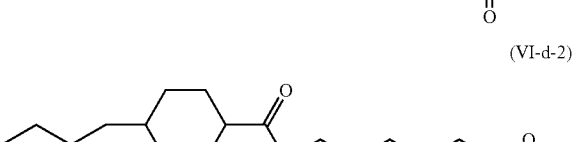
(VI-d-3)
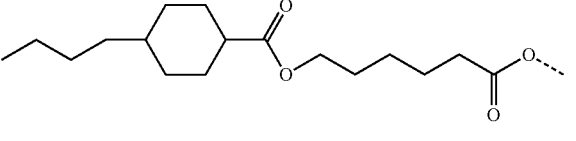
(VI-d-4)
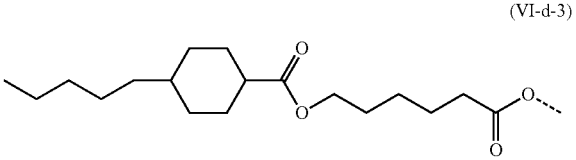
(VI-d-5)
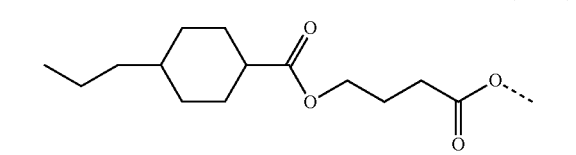
(VI-d-6)
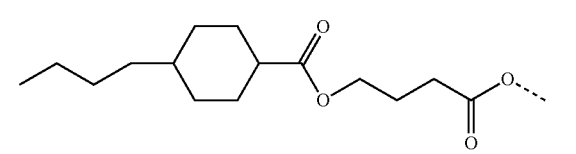
(VI-d-7)
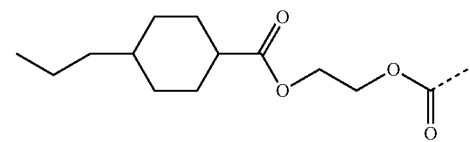
(VI-d-8)
(VI-d-9)
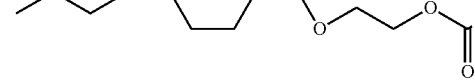
(VI-d-10)
(VI-d-11)
(VI-d-12)
(VI-d-13)
(VI-d-14)

-continued
(VI-d-15)
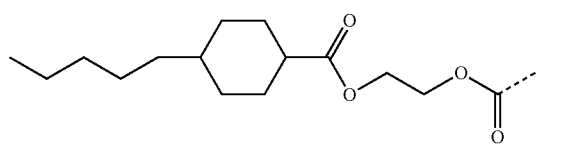
[Chem. 51]
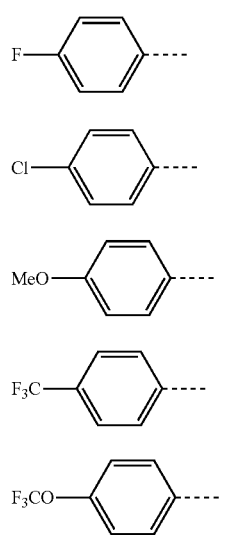
(VI-e-1)
(VI-e-2)
(VI-e-3)
(VI-e-4)
(VI-e-5)
(VI-e-6)
(VI-e-7)
(VI-e-8)
(VI-e-9)
[Chem. 52]
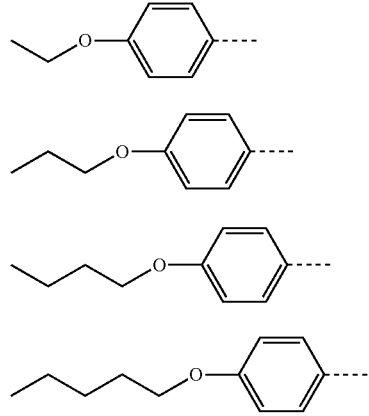
(VI-f-1)
(VI-f-2)
(VI-f-3)
(VI-f-4)
-continued
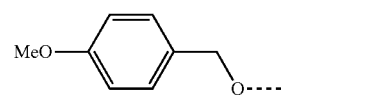 (VI-f-5)
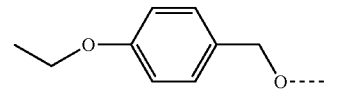 (VI-f-6)
(VI-f-7)
(VI-f-8)
(VI-f-9)
(VI-f-10)
[Chem. 53]
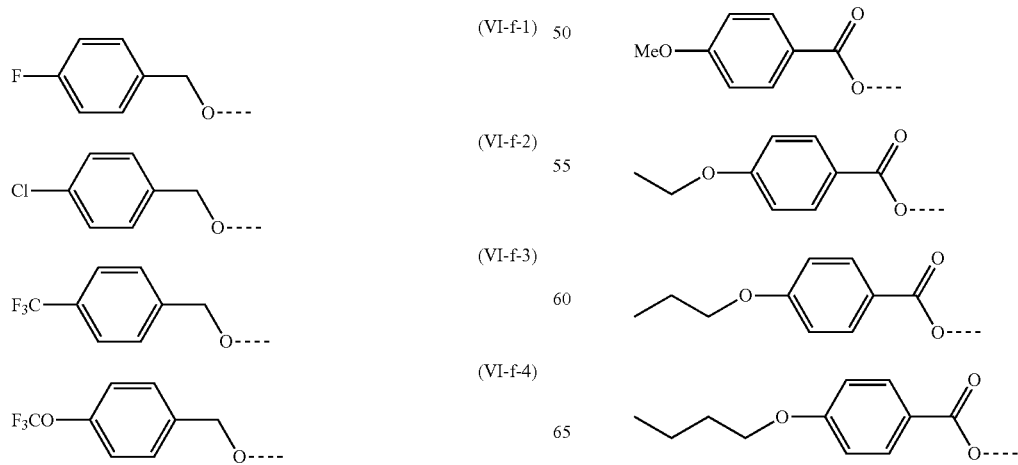
(VI-g-1)
(VI-g-2)
(VI-g-3)
(VI-g-4)
(VI-g-5)
(VI-g-6)
(VI-g-7)
(VI-g-8)

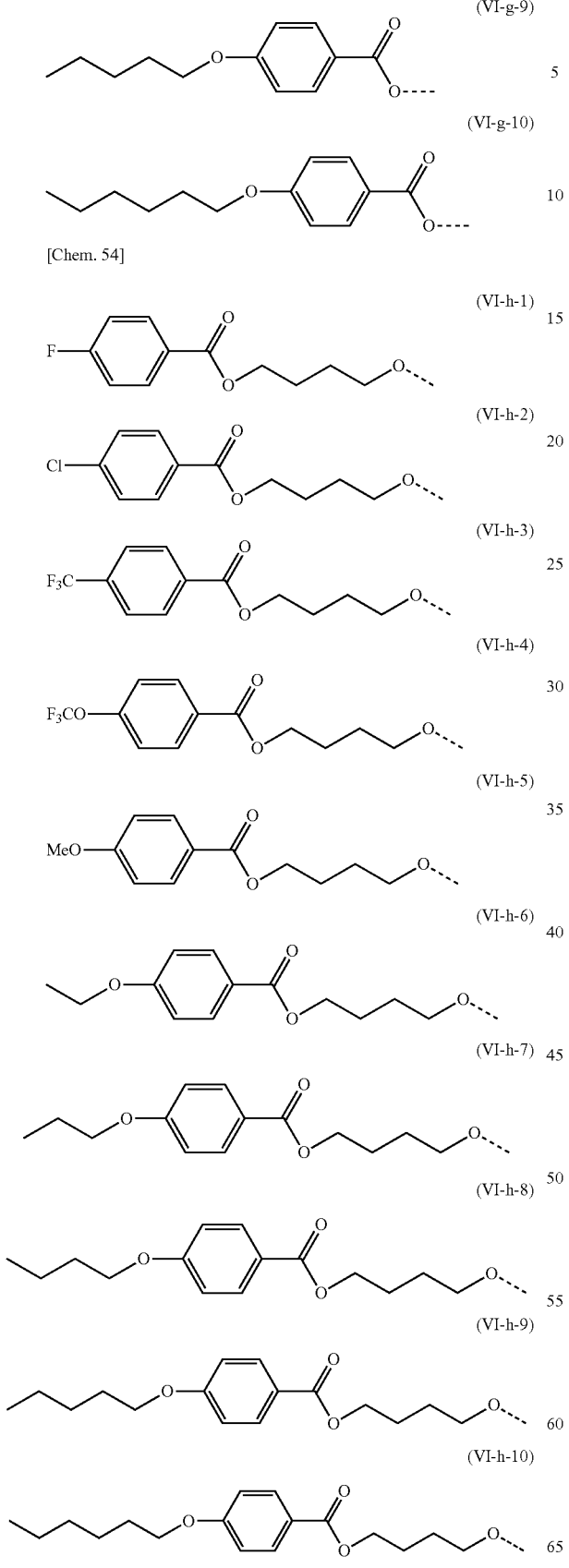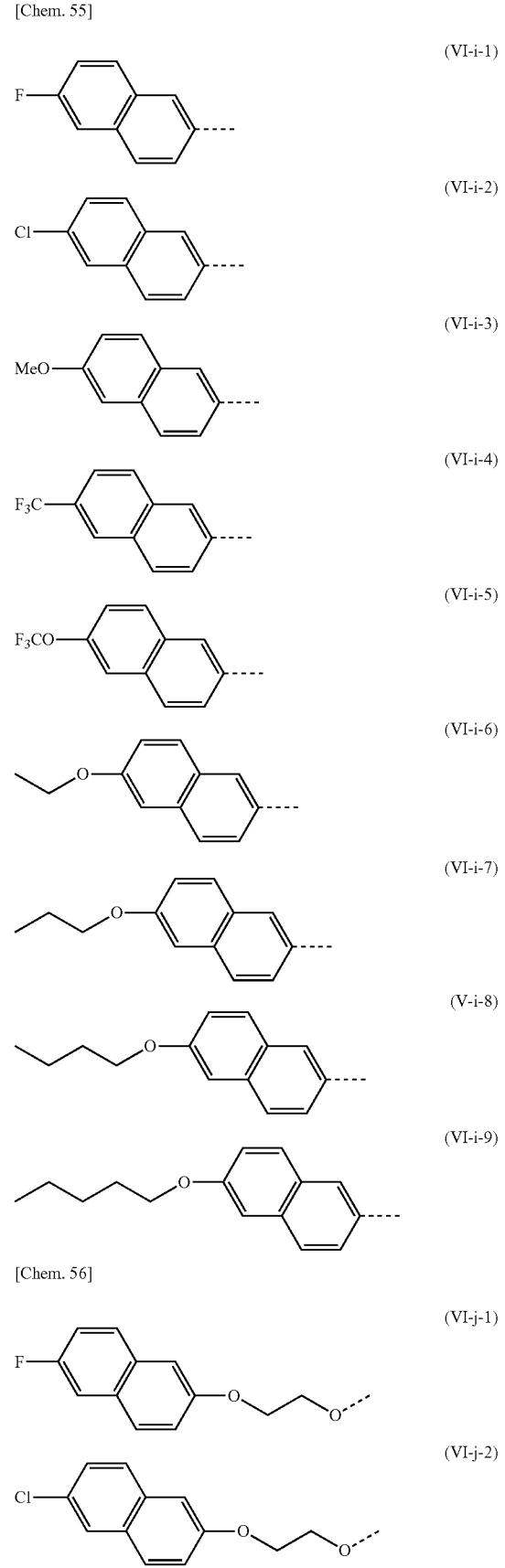

(VI-j-3) 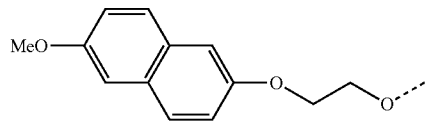
(VI-j-4) 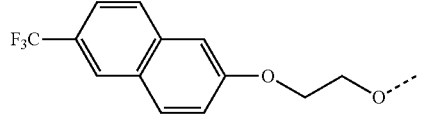
(VI-j-5) 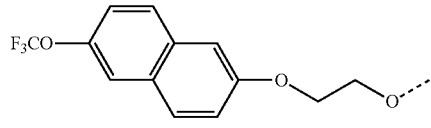
(VI-j-6) 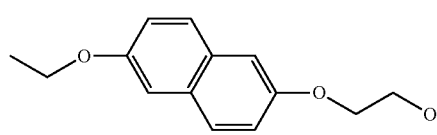
(VI-j-7) 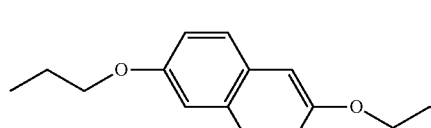
(VI-j-8) 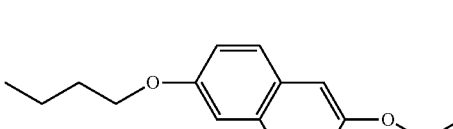
(VI-j-9) 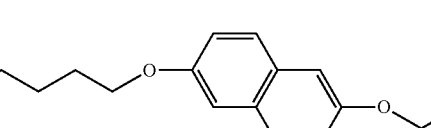
[Chem. 57]
(VI-k-1) 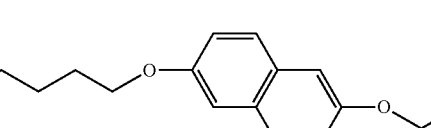
(VI-k-2) 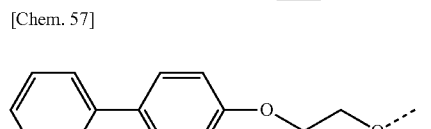
(VI-k-3) 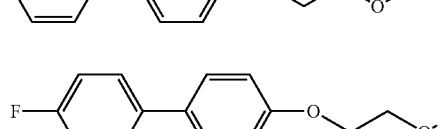
(VI-k-4) 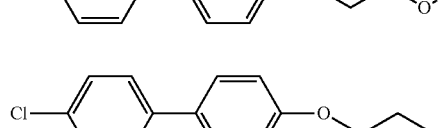
(VI-k-5) 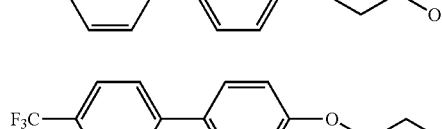
(VI-k-6) 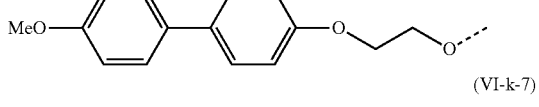
(VI-k-7) 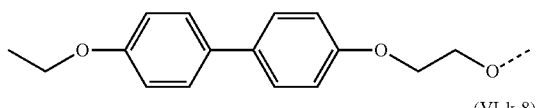
(VI-k-8) 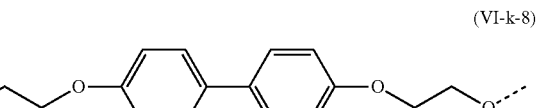
(VI-k-9) 
(VI-k-10) 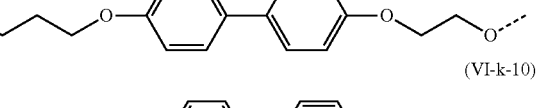
(VI-k-11) 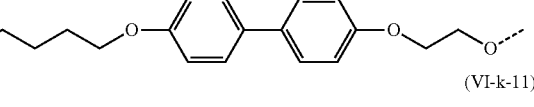
[Chem. 58]
(VI-l-1) 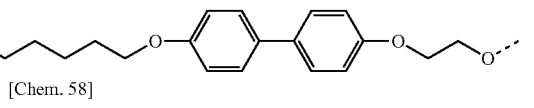
(VI-l-2) 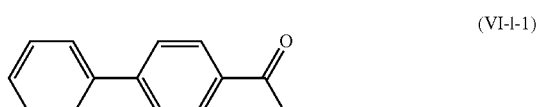
(VI-l-3) 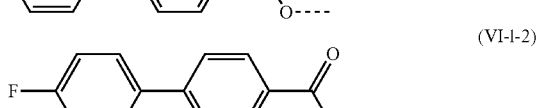
(VI-l-4) 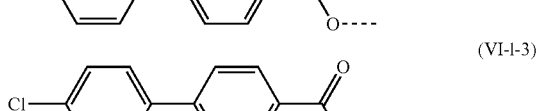
(VI-l-5) 
(VI-l-6) 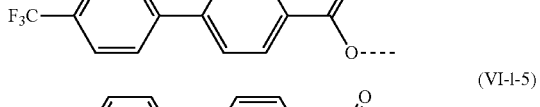
(VI-l-7) 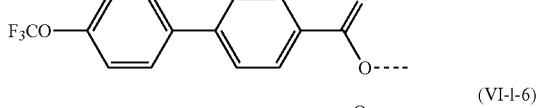
(VI-l-8) 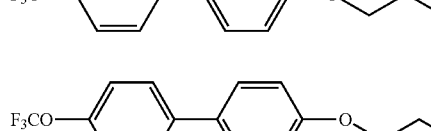

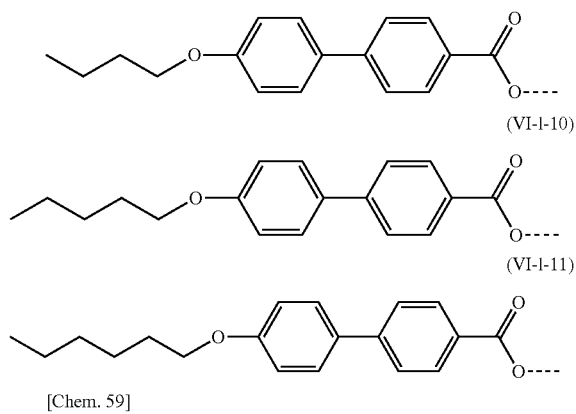
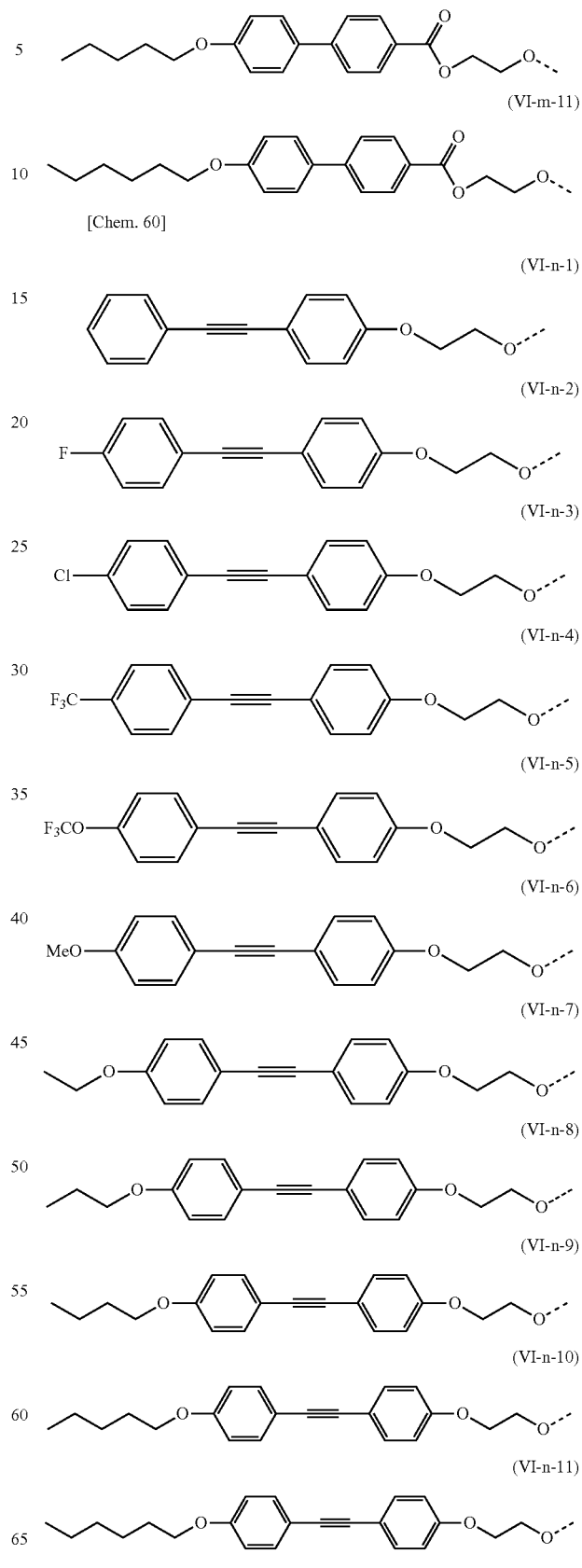

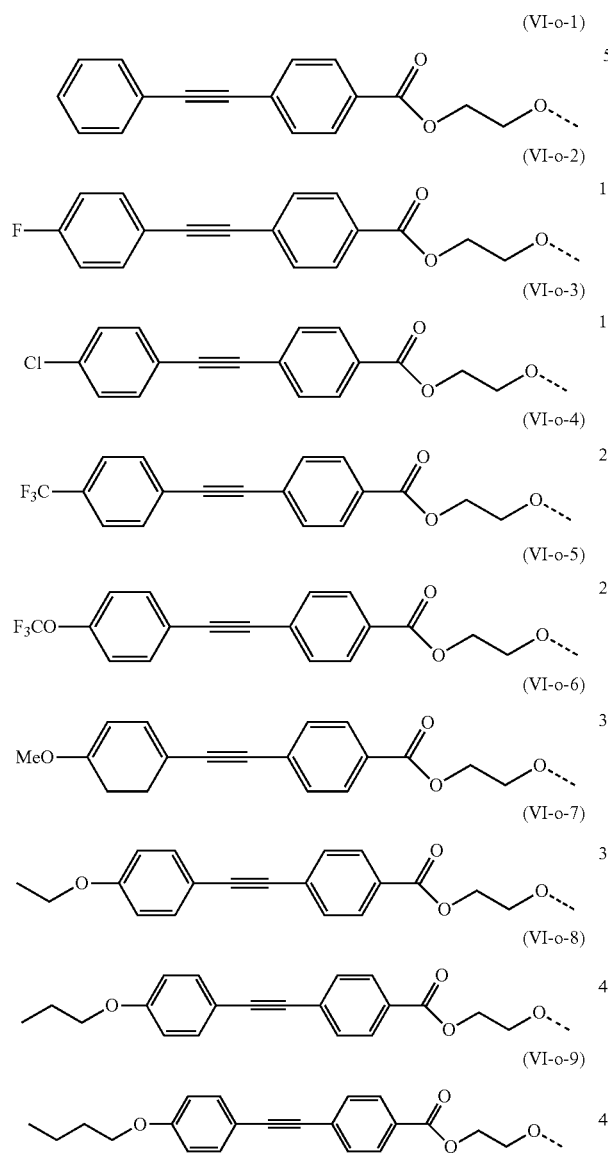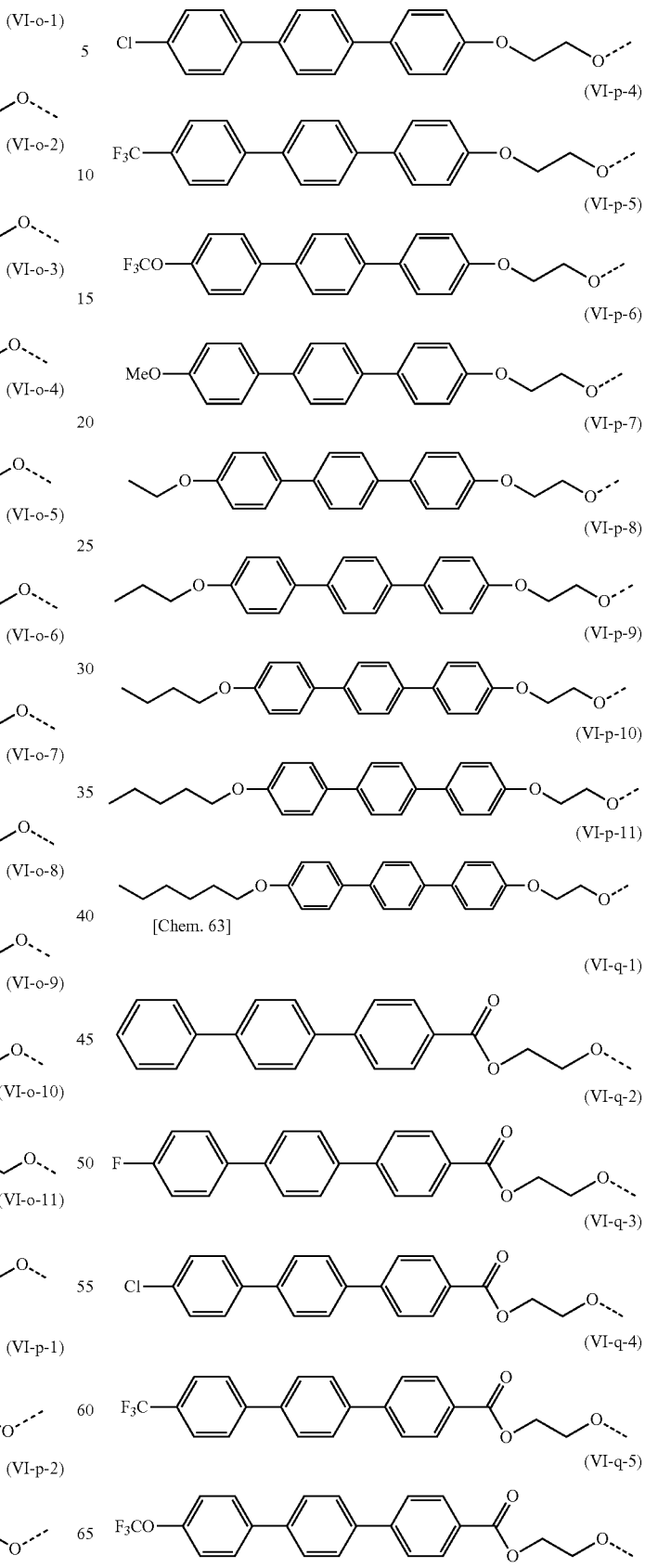

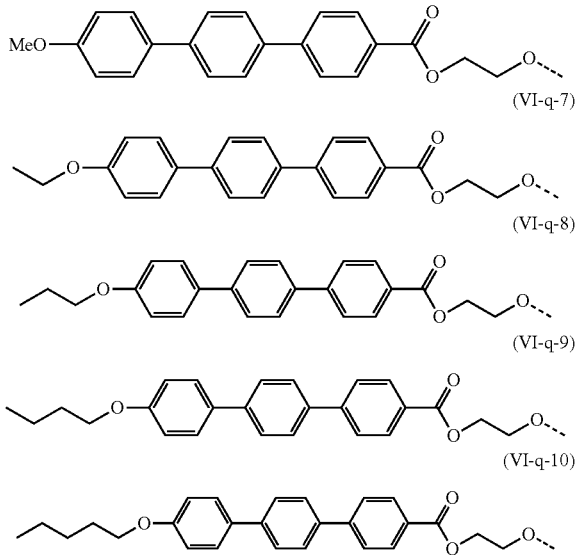

In the polymer represented by the general formula (V) of the present invention, as $M_b$ or $M_d$, for example, acrylate, methacrylate, acrylamide, methacrylamide, maleic acid derivatives, siloxanes, epoxides, an acryloyloxy group, a methacryloyloxy group, a 2-chloroacryloyloxy group, a 2-phenylacryloyloxy group, a 2-phenyloxyacryloyloxy group, an acrylamide group, a methacrylamide group, a 2-chloromethacrylamide group, a 2-phenylacrylamide group, a vinyloxy group, a styryl group, a vinyloxycarbonyl group, a maleimide group, maleic esters, fumaric esters, siloxanes, a vinyl group, or an epoxy group may be used.

[Preparation of Polymer for Alignment Layer]

The cinnamic acid derivative in the present invention may be used alone as a material for the polymer, or the cinnamic acid derivative may be used in a composition formed by mixing other monomers with the cinnamic acid derivative. In the composition, it is possible to prepare the polymer at an arbitrary mixing ratio of the cinnamic acid derivative and the other monomers. For example, the ratio of the other monomers relative to 100-fold moles of the cinnamic acid derivative is preferably from 0.1-fold mole to 30-fold moles. Further, the other monomers are preferably liquid crystalline compounds.

It is preferable that the material and the composition include a solvent and/or a polymerization initiator.

The polymer of the present invention can be prepared by polymerizing the cinnamic acid derivative or the composition in the present invention.

During the polymerization, a polymerization initiator may be optionally used, depending on the polymerization mode of the polymerizable functional group. Examples of the polymerization initiator include those as described in known publications such as "Synthesis and Reaction of Polymers, edited by The Society of Polymer Science, Japan and published by Kyoritsu Shuppan Co., Ltd.".

Examples of the thermal polymerization initiator in the radical polymerization include azo compounds such as azobisisobutyronitrile and peroxides such as benzoyl peroxide.

Examples of a photopolymerization initiator include aromatic ketone compounds such as benzophenone, Michler's ketone, xanthone, and thioxanthone, quinones such as 2-ethylanthraquinone, acetophenone compounds such as acetophenone, trichloroacetophenone, 2-hydroxy-2-methylpropiophenone, 1-hydroxycyclohexyl phenyl ketone, benzoin ether, 2,2-diethoxyacetophenone, and 2,2-dimethoxy-2-phenylacetophenone, diketone compounds such as benzyl and methylbenzoyl formate, acyloxime ester compounds such as 1-phenyl-1,2-propanedione-2-(o-benzoyl)oxime, acylphosphine oxide compounds such as 2,4,6-trimethylbenzoyldiphenylphosphine oxide, sulfur compounds such as tetramethylthiuram and dithiocarbamate, organic peroxides such as benzoyl peroxide, and azo compounds such as azobisisobutyronitrile.

Further, examples of the thermal polymerization initiator used in cationic polymerization include aromatic sulfonium salt compounds.

In addition, examples of the photopolymerization initiator include organic sulfonium salt compounds, iodonium salt compounds, and phosphonium compounds.

The amount of the polymerization initiator added is preferably from 0.1% by mass to 10% by mass, more preferably from 0.1% by mass to 6% by mass, and still more preferably from 0.1% by mass to 3% by mass in the composition. Further, a desired polymer can be synthesized by an addition reaction to a polymer main chain, such as with a polysiloxane compound.

The polymer in the present invention is obtained by first subjecting the materials or the composition to a polymerization reaction in a reactor made of glass, stainless steel, or the like, and then purifying the resulting polymer. Preferable examples of the solvent which may be included in the materials or the composition include benzene, toluene, xylene, ethylbenzene, pentane, hexane, heptane, octane, cyclohexane, cycloheptane, methanol, ethanol, 1-propanol, 2-propanol, ethylene glycol, ethylene glycol monomethyl ether, ethylene glycol dimethyl ether, 2-butanone, acetone, tetrahydrofuran, γ-butyrolactone, N-methyl-pyrrolidone, dimethyl sulfoxide, and dimethylformamide. The organic solvents may be used alone or in combination of two or more kinds thereof.

The polymer according to the present invention can also be obtained by dissolving the cinnamic acid derivative or the composition in a solvent, applying the solution onto a substrate to remove the solvent by drying, and conducting a polymerization reaction by heating or light irradiation.

[Method for Forming Liquid Crystal Alignment Layer]

The ability to control the alignment of liquid crystal molecules and the stability of the alignment of the liquid crystal molecules against heat and light can be developed by irradiating the polymer in the present invention with light. The liquid crystal alignment layer obtained from the polymer of the present invention, which is obtained by conducting light irradiation, may be referred to as a photo-alignment film.

An example of a method for producing the liquid crystal alignment layer (photo-alignment film) of the present invention is a method of dissolving the polymer in a solvent, applying the solution onto a substrate, and then irradiating the coating film with light to exhibit the ability to control the alignment to afford a photo-alignment film.

The solvent used in dissolving the polymer is preferably a solvent that dissolves but does not react with the polymer of the present invention and other components optionally used. Examples of the solvent include 1,1,2-trichloroethane, N-methylpyrrolidone, butoxyethanol, γ-butyrolactone, ethylene glycol, polyethylene glycol monomethyl ether, propylene glycol, 2-pyrrolidone, N,N-dimethylformamide, phenoxyethanol, tetrahydrofuran, dimethylsulfoxide, methyl isobutyl ketone, and cyclohexanone. The organic solvents may be used alone or in combination of two or more kinds thereof.

Another method for producing the liquid crystal alignment layer (photo-alignment film) of the present invention is a method of dissolving the cinnamic acid derivative or the composition of the present invention in a solvent, applying the solution onto a substrate, heating the coating film or irradiating the coating film with light to prepare a polymer, and further irradiating the polymer with light to exhibit the ability to control the alignment, thereby affording a photo-alignment film.

As a solvent used for dissolving the cinnamic acid derivative or the composition, the same solvent as the solvent used for dissolving the polymer may be used.

In the method for producing the liquid crystal alignment layer (photo-alignment film) of the present invention, preparation of the polymer and exhibition of an ability to control the alignment may be simultaneously conducted by light irradiation. Further, preparation of the polymer and exhibition of an ability to control the alignment may be separately conducted by a method of combining heating and light irradiation or by a method of combining two or more light beams having different wavelengths.

In any of the methods of producing the liquid crystal alignment layer (photo-alignment film) of the present invention, an alignment film may be preliminarily formed on a substrate and then a photo-alignment film using the cinnamic acid derivative, the composition, or the polymer of the present invention may be produced on the substrate so that the substrate may be provided with an ability to control the alignment direction and the alignment angle.

Examples of the material for the substrate include glass, silicon, polyethylene terephthalate, polybutylene terephthalate, polyether sulfone, polycarbonate, and triacetyl cellulose. An electrode layer (conductive layer) such as Cr, Al, an ITO film composed of $In_2O_3$—$SnO_2$, and a NESA film composed of $SnO_2$ may be provided to this substrate. For the patterning of these electrode layers, a photoetching method may be applied. Further, the electrode layers may also be patterned by, for example, a method using a mask, in forming the electrode layers. In addition, a color filter layer or the like may also be formed on the substrate.

Examples of the method of applying a solution of the cinnamic acid derivative, the composition, or the polymer of the present invention onto a substrate include spin coating, die coating, gravure coating, flexographic printing, and ink jet printing.

The concentration of the solid content in the solution used in the application is preferably 0.5% by weight to 10% by weight, and is more preferably selected from this range by considering a method of applying the solution on the substrate, viscosity, volatility, or the like.

Further, the applied surface is preferably heated after the application so as to remove the solvent. The drying conditions are preferably 50° C. to 300° C., and more preferably 80° C. to 200° C. for preferably 2 minutes to 200 minutes, and more preferably 2 minutes to 100 minutes.

In the case where the cinnamic acid derivative or the composition of the present invention is used, a polymer may be prepared on the substrate by conducting thermal polymerization by the heating treatment, and in this case, a polymerization initiator is preferably added to the material and the composition. Alternatively, a polymer may be prepared by photopolymerization through irradiating the composition with unpolarized light after removal of the solvent in the heating treatment, or alternatively, thermal polymerization and photopolymerization may be combined.

In the case of preparing the polymer by thermal polymerization on the substrate, the heating temperature may be any temperature sufficient for allowing the polymerization to proceed. Typically, the heating temperature is about 50° C. to 250° C., and more preferably about 70° C. to 200° C. Further, the polymerization initiator may or may not be added to the composition.

In preparing the polymer by photopolymerization on the substrate, unpolarized ultraviolet light is preferably used for light irradiation. Moreover, a polymerization initiator is preferably incorporated into the composition. The irradiation energy is preferably 10 mJ/cm$^2$ to 8000 mJ/cm$^2$, and more preferably 40 mJ/cm$^2$ to 5000 mJ/cm$^2$. The luminous intensity is preferably 2 mW/cm$^2$ to 1000 mW/cm$^2$, and more preferably 4 mW/cm$^2$ to 500 mW/cm$^2$. The radiation wavelength preferably has a peak in a range of 250 nm to 450 nm.

Next, a photocrosslinking reaction is conducted on a coating film composed of the polymer formed by the method, by applying linear polarized light in the coated surface normal direction and applying unpolarized or linear polarized light in an oblique direction and curing is conducted to exhibit an ability to control the alignment. Further, these irradiation methods may be combined. In order to form a desired pretilt angle, irradiation with linear polarized light in an oblique direction is preferable. Further, the oblique direction refers to inclination with respect to a direction parallel to the substrate surface and this angle of inclination is referred to as a pretilt angle. In the case where the film is used as the alignment film for vertical alignment, the pretilt angle is typically preferably 70° to 89.8°. Further, in the case where the film is used as an alignment film for horizontal alignment, typically, the pretilt angle is preferably 1° to 7°, and in an IPS mode, the pretilt angle is preferably 0° to 1°.

As the light used for irradiation when subjecting a coating film composed of the polymer to curing (photocrosslinking reaction), thereby forming the film into a liquid crystal alignment layer (photo-alignment film), for example, ultraviolet rays or visible rays containing light having a wavelength of 150 nm to 800 nm may be used, and among these, ultraviolet rays having a wavelength of 270 nm to 450 nm are particularly preferable.

Examples of the light source include a xenon lamp, a high-pressure mercury lamp, an ultrahigh-pressure mercury lamp, and a metal halide lamp. Linear polarized light is obtained by using a polarizing filter and a polarizing prism for light from these light sources. Further, the ultraviolet light and visible light obtained from such light sources may have a wavelength range for irradiation restricted by using an interference filter or a color filter.

In addition, the irradiation energy is preferably 15 mJ/cm$^2$ to 500 mJ/cm$^2$, and more preferably 20 mJ/cm$^2$ to 300 mJ/cm$^2$. The luminous intensity is more preferably 2 mW/cm$^2$ to 500 mW/cm$^2$, and still more preferably 5 mW/cm$^2$ to 300 mW/cm$^2$.

The thickness of the liquid crystal alignment layer (photo-alignment film) to be formed is preferably about 10 nm to 250 nm, and more preferably about 10 nm to 100 nm.

[Method for Producing Liquid Crystal Display Element]

A liquid crystal cell including a pair of substrates and a liquid crystal composition sandwiched between the substrates, and a liquid crystal display element using the same can be produced by using the liquid crystal alignment layer (photo-alignment film) formed by the method as described above, for example, by the following manner.

By preparing two substrates on which the liquid crystal alignment layer in the present invention is formed and arranging liquid crystal between the two substrates, a liquid crystal cell can be produced. Further, the liquid crystal alignment layer may be formed on only one of the two substrates.

Examples of a method for producing the liquid crystal cell include the following methods.

First, two substrates are arranged so that the respective liquid crystal alignment layers face each other, and the peripheral portions of the two substrates are bonded with a sealing agent while maintaining a particular space (cell gap) between the two substrates. Liquid crystal is poured into a cell gap defined by the substrate surfaces and the sealing agent to fill the cell gap, and the inlet hole is sealed to produce a liquid crystal cell.

The liquid crystal cell may also be produced by a technique called a One Drop Fill (ODF) process. The process can be conducted, for example, by the following procedure. For example, an ultraviolet light-curable sealing agent is applied to a predetermined position on a substrate on which the liquid crystal alignment layer is formed, a liquid crystal is dropped onto the liquid crystal alignment layer, and another substrate is then bonded so that the liquid crystal alignment layers face each other. Then, the entire surfaces of the substrates are irradiated with UV light to cure the sealing agent, thereby producing a liquid crystal cell.

Regardless of the method with which the liquid crystal cell is produced, the liquid crystal used is preferably heated to a temperature at which the liquid crystal transitions to an isotropic phase and then slowly cooled to room temperature so as to eliminate the alignment induced by the flow during pouring.

For example, an epoxy resin may be used as the sealing agent.

In order to keep the cell gap constant, beads of silica gel, alumina, acrylic resin, or the like may be used as a spacer prior to bonding the two substrates. These spacers may be spread over the coating film of the liquid crystal alignment layer, or added to a sealing agent and then two substrates may be bonded.

For example, nematic-type liquid crystals may be used as the liquid crystal.

For a vertical alignment-type liquid crystal cell, a liquid crystal having a negative dielectric anisotropy is preferable, and for example, dicyanobenzene-based liquid crystals, pyridazine-based liquid crystals, Schiff-base-based liquid crystals, azoxy-based liquid crystals, naphthalene-based liquid crystals, biphenyl-based liquid crystals, and phenylcyclohexane-based liquid crystals are used.

In the case of the horizontal alignment type liquid crystal cell, a liquid crystal having a positive dielectric anisotropy is preferable. For example, cyanobenzene-based liquid crystals, difluorobenzene-based liquid crystals, trifluorobenzene-based liquid crystals, trifluoromethylbenzene-based liquid crystals, trifluoromethoxybenzene-based liquid crystals, pyrimidine-based liquid crystals, naphthalene-based liquid crystals, biphenyl-based liquid crystals, phenylcyclohexane-based liquid crystals, or the like are used.

A liquid crystal display element can be obtained by bonding a polarizing plate to an outer surface of the liquid crystal cell thus produced. Examples of the polarizing plate include a polarizing plate formed of an "H film" in which iodine has been absorbed while stretching and aligning a polyvinyl alcohol, and a polarizing plate having an H film sandwiched between cellulose acetate protective films.

The liquid crystal display element of the present invention thus produced is excellent in various kinds of performance such as display characteristics and reliability. Further, as the alignment mode of the liquid crystal display element, both a horizontal alignment mode and a vertical alignment mode can be produced.

[Method for Producing Optical Anisotropic Body]

An optical anisotropic body may also be produced by applying a polymerizable liquid crystal composition onto the photo-alignment film and polymerizing it while aligning the polymerizable liquid crystal molecules in the polymerizable liquid crystal composition.

The polymerizable liquid crystal composition is a liquid crystal composition containing a polymerizable liquid crystal which exhibits liquid crystal properties either alone or in a composition with another liquid crystal compound. Examples of such compounds include rod-shaped polymerizable liquid crystal compounds having a rigid site, referred to as a mesogen in which a plurality of structures such as a 1,4-phenylyene group and a 1,4-cyclohexylene group are connected, and a polymerizable functional group such as a (meth)acryloyloxy group, a vinyloxy group, and an epoxy group, as described in the Handbook of Liquid Crystals (edited by D. Demus, J. W. Goodby, G W. Gray, H. W. Spiess, V. Vill, published by Wiley-VCH publishers, 1998), Kikan Kagaku Sosetsu No. 22, Liquid Crystal Chemistry (edited by Chemical Society of Japan, 1994), or Japanese Unexamined Patent Application, First Publication Nos. H07-294735, H08-3111, H08-29618, H11-80090, H11-148079, 2000-178233, 2002-308831, and 2002-145830; rod-shaped polymerizable liquid crystal compounds having a maleimide group as described in Japanese Unexamined Patent Application, First Publication Nos. 2004-2373 and 2004-99446; rod-shaped polymerizable liquid crystal compounds having an allyl ether group as described in Japanese Unexamined Patent Application, First Publication No. 2004-149522; and for example, discotic polymerizable compounds as described in the Handbook of Liquid Crystals, (edited by D. Demus, J. W. Goodby, G W. Gray, H. W. Spiess, V. Vill, published by Wiley-VCH, 1998), Kikan Kagaku Sosetsu No. 22, Liquid Crystal Chemistry (edited by Chemical Society of Japan, 1994) or Japanese Unexamined Patent Application, First Publication No. H07-146409. Among these, the rod-shaped liquid crystal compounds having a polymerizable group are preferable since a film having a low liquid crystal temperature range which is in the vicinity of room temperature is easily fabricated.

EXAMPLES

The present invention will be described in further detail with reference to Examples below, but the present invention is not limited to Examples. The structure of a compound was identified with a nuclear magnetic resonance (NMR) spectrum, a mass spectrum (MS), or the like. Unless otherwise noted, "parts" and "%" are on a mass basis.

Synthesis of Cinnamic Acid Derivative DiCin-1

Example 1

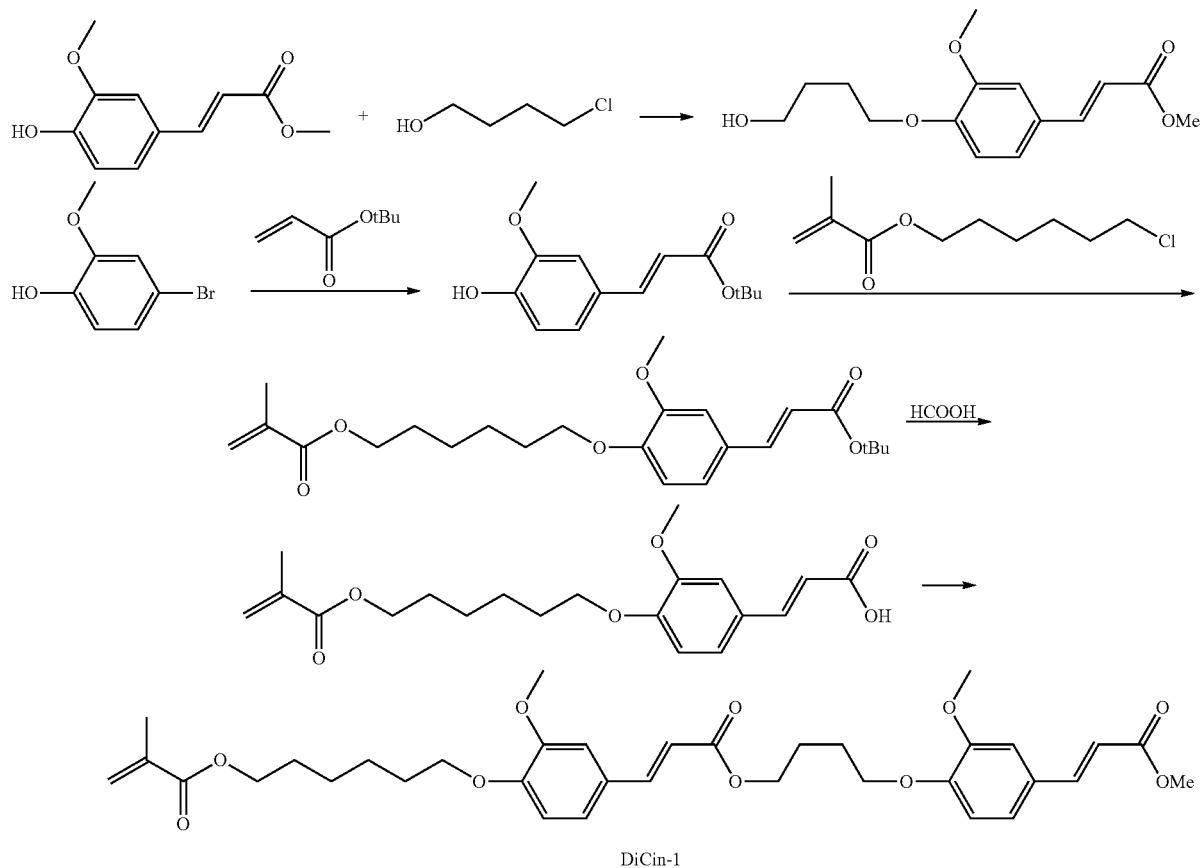

DiCin-1

Methyl 4-hydroxy-3-methoxycinnamate (20.8 g) and potassium carbonate (30 g) were suspended in dimethyl formamide (150 ml), and the suspension was heated to 90° C. Next, 4-chloro-1-butanol (21.6 g) was added dropwise thereto over 2 hours, and the mixture was stirred at 90° C. for 3 hours. Further, potassium carbonate (60 g) and 4-chloro-1-butanol (44 g) were added thereto. After confirming the completion of the reaction, dimethylformamide was evaporated under reduced pressure. The remaining solid was dissolved in dichloromethane, and the solution was washed with 5% hydrochloric acid and water. The solvent was evaporated under reduced pressure, and the obtained solid was purified by column chromatography to obtain methyl 4-hydroxy-3-methoxycinnamate (24 g) as a yellow liquid.

$^1$H NMR (400 MHz, CDCl$_3$) δ: 1.75-1.79 (p, 2H), 1.95-1.99 (p, 2H), 3.71-3.74 (t, 2H), 3.80 (m, 3H), 3.89 (t, 3H), 4.07-4.10 (t, 2H), 6.29-6.33 (d, 1H), 6.85-6.87 (d, 2H), 7.04 (m, 1H), 7.07-7.09 (d, 2H), 7.61-7.65 (d, 2H).

The reaction vessel was purged with nitrogen, and 4-bromo-2-methoxyphenol (91 g), tert-butyl acrylate (69.0 g), and potassium carbonate (92.9 g) were added thereto, and the mixture was suspended in N-methylpyrrolidone (500 ml) at 25° C. Palladium acetate (101 mg) was added thereto at 25° C., and the mixture was stirred at 100° C. for 1 hour, and subsequently at 110° C. for 1 hour and at 120° C. for 1 hour. After confirming the completion of the reaction, the mixture was stirred, and water and 10% hydrochloric acid were added dropwise thereto to neutralize the mixture to pH=6 to 7 while maintaining the inner temperature to lower than 25° C. The insoluble solid was separated by filtration and washed with toluene. The obtained solution was extracted twice with toluene, and the combined organic phase was washed with water and 10% saline. Toluene was evaporated under reduced pressure to obtain a crude product of tert-butyl 4-hydroxy-3-methoxy cinnamate (142 g) as a brown viscous liquid.

Next, the obtained tert-butyl 4-hydroxy-3-methoxycinnamate (23 g), 6-chlorohexyl methacrylate (20.0 g), and cesium carbonate (62 g) were dissolved in dimethyl sulfoxide (150 ml), and the solution was stirred at 60° C. for 3 hours. The reaction solution was cooled to room temperature, and 600 ml of water and 300 ml of dichloromethane were added thereto. The organic phase was separated and the aqueous layer was extracted twice with 150 ml of dichloromethane. The organic phase was combined, and washed with 10% hydrochloric acid, saturated aqueous sodium bicarbonate, and saturated saline, and then dried by the addition of sodium sulfate. Sodium sulfate was removed and the mixture was purified by column chromatography (alumina/silica gel, dichloromethane), and the solvent was evaporated under a reduced pressure to obtain tert-butyl 4-(6-methacryloyloxy)-3-methoxycinnamate (34 g) as a white solid.

Next, the obtained tert-butyl 4-(6-methacryloyloxy)-3-methoxycinnamate (30 g) was dissolved in dichloromethane (300 ml) at 25° C., and 98% formic acid (60 ml) was added thereto at 25° C. The mixture was stirred at 40° C. for 2 hours, and after confirming the completion of the reaction, the inner temperature was cooled to 25° C. Dichloromethane was evaporated under reduced pressure and then the solid was recrystallized from methanol to obtain 4-(6-methacryloyloxy)-3-methoxycinnamic acid (25 g) as a white solid.

Next, the obtained 4-(6-methacryloyloxy)-3-methoxycinnamic acid (18.6 g), methyl 4-hydroxy-3-methoxycinnamate (15.2 g), and N,N-dimethylaminopyridine (0.7 g) were dissolved in ice-cooled dichloromethane (300 ml) under a nitrogen atmosphere. Diisopropylcarbodiimide (7.21 g) diluted in 20 ml of dichloromethane was added dropwise thereto, and the reaction solution was stirred at room temperature for 12 hours. The reaction solution was filtered, washed with 10% hydrochloric acid and saturated saline, and then dried over sodium sulfate.

Sodium sulfate was removed, and the residue was purified by column chromatography (alumina/silica gel, dichloromethane/ethyl acetate) and then recrystallized from methanol to obtain DiCin-1 (28 g) as a white solid.

$^1$H NMR (400 MHz, CDCl$_3$) δ: 1.46-1.53 (p, 4H), 1.70-1.73 (p, 2H), 1.85-1.91 (p, 4H), 1.94 (m, 3H), 1.99-2.02 (p, 2H), 3.80 (m, 3H), 3.89 (m, 6H), 4.03-4.06 (t, 2H), 4.10-4.11 (t, 2H), 4.13-4.17 (t, 2H), 4.27-4.30 (t, 2H), 5.55 (m, 1H), 6.09 (m, 1H), 6.27-6.32 (dd, 2H), 6.84-6.88 (t, 2H), 7.05-7.09 (p, 4H), 7.59-7.65 (dd, 2H).

EI-MS: 624[M$^+$]

In the same manner, the following compounds DiCin-2 to DiCin-12 were synthesized.

[Chem. 65]

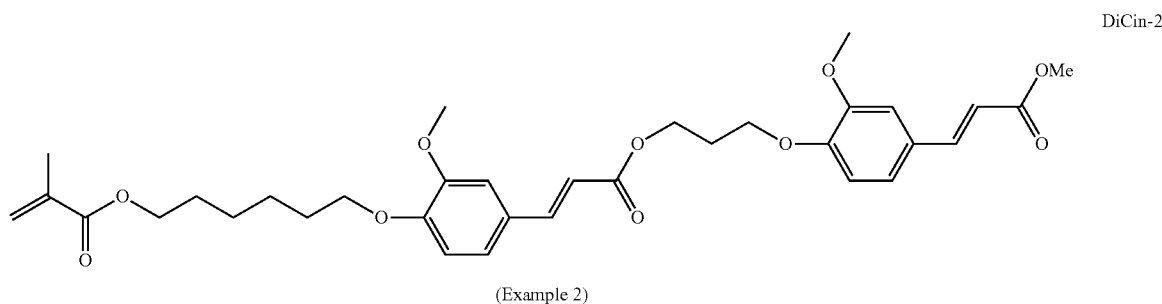

(Example 2)

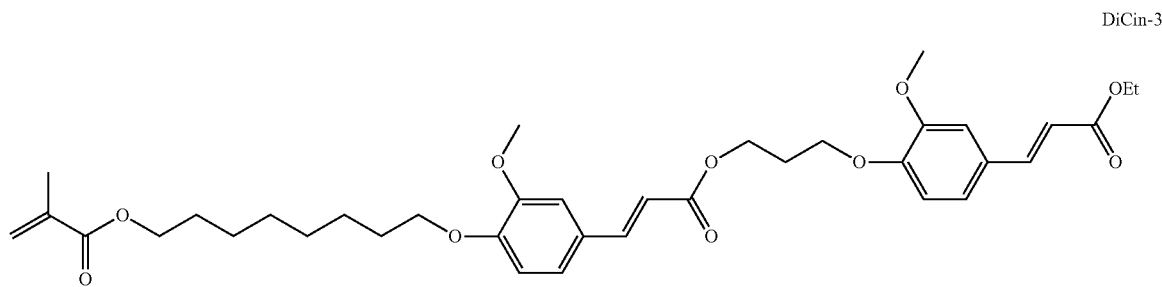

(Example 3)

[Chem. 66]

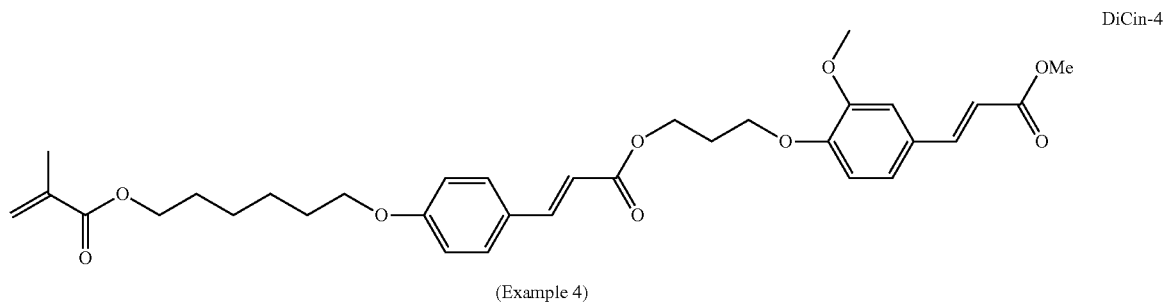

(Example 4)

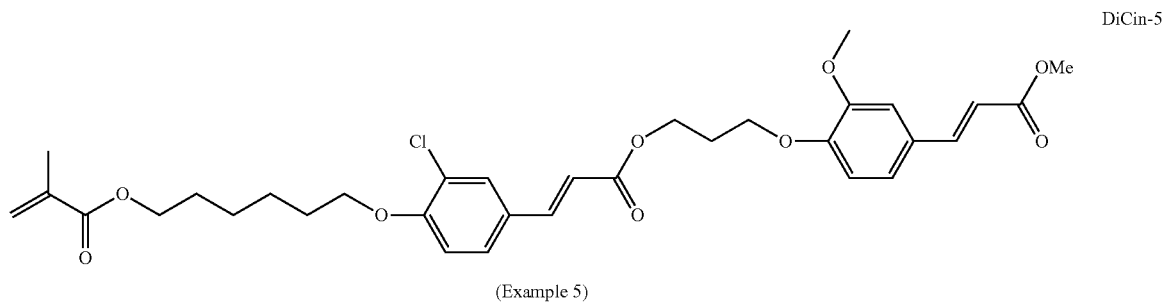
(Example 5) DiCin-5
[Chem. 67]
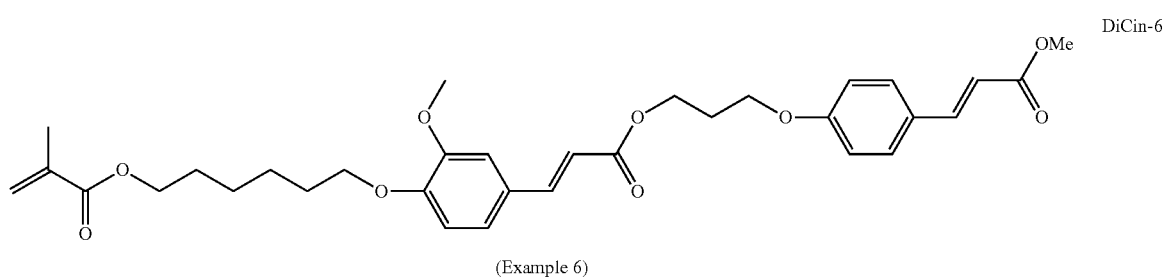
(Example 6) DiCin-6
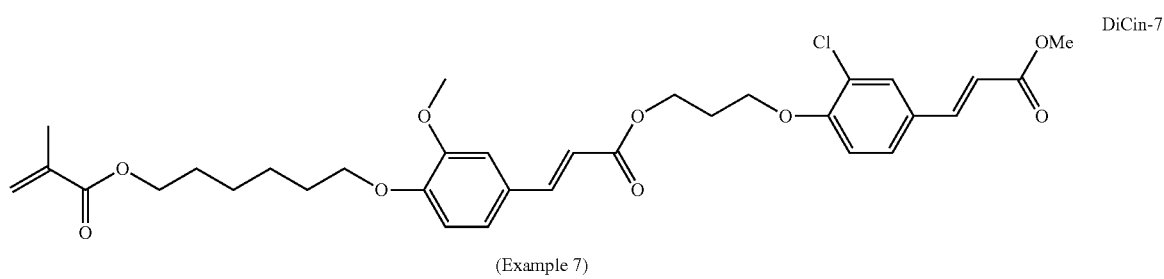
(Example 7) DiCin-7
[Chem. 68]
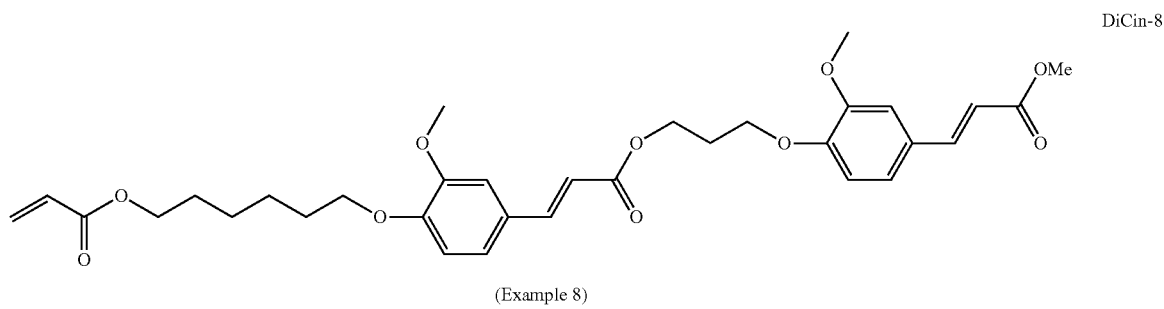
(Example 8) DiCin-8
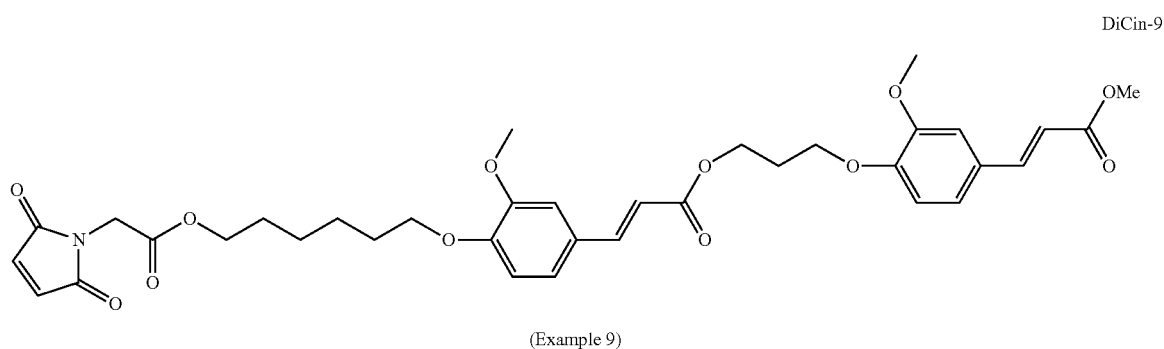
(Example 9) DiCin-9

[Chem. 69]

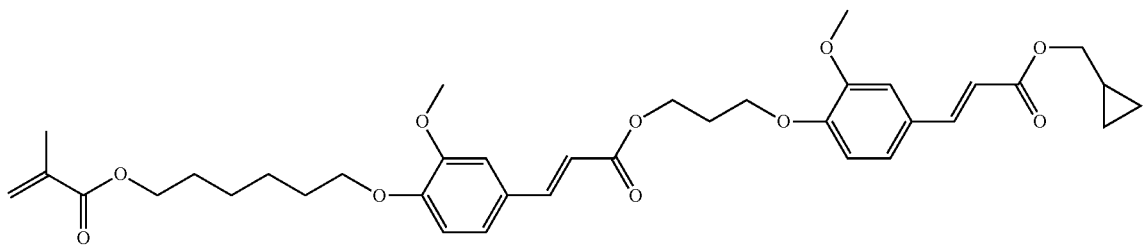

(Example 10)

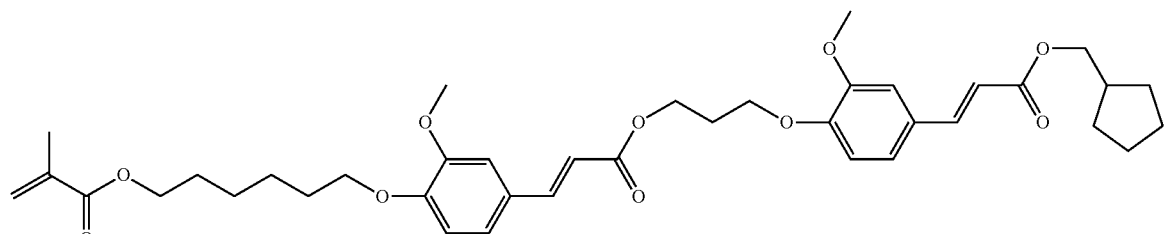

(Example 11)

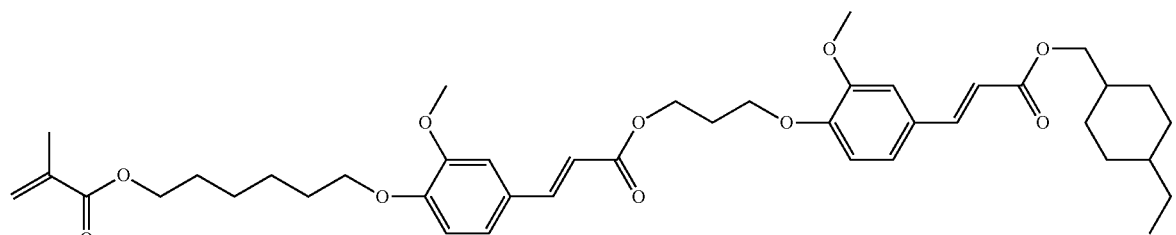

(Example 12)

Synthesis of Monomers for Copolymerization

[Chem. 70]

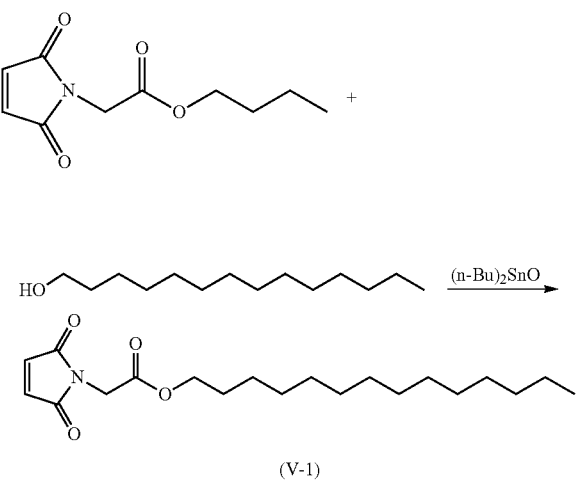

9.01 g of butyl maleimidoacetate, 0.33 g of dibutyltin (IV) oxide, and 9.14 g of tetradecanol were dissolved in 40 mL of toluene, followed by stirring for 15 hours while heating to reflux. The reaction solution was cooled to room temperature and 100 ml of toluene was added thereto. The mixture was subjected to liquid separation and washed with saturated aqueous sodium bicarbonate and then with saturated saline. To this solution was added sodium sulfate, and the mixture was dried. Sodium sulfate was removed and the solvent was evaporated under reduced pressure to reduce the volume to about 50 ml, and 40 ml of hexane and 20 ml of dichloromethane were added thereto. The mixture was purified by column chromatography (alumina/silica gel, hexane/dichloromethane=2:1), the solvent was evaporated under reduced pressure, and the residue was reprecipitated with methanol to obtain (V-1) (7.95 g) as a white crystal.

$^1$H-NMR (400 MHz, CDCl$_3$) δ: 0.88 (t, J=6.8 Hz, 3H), 1.15-1.40 (m, 22H), 1.61-1.66 (tt, 2H), 4.14 (t, J=6.6 Hz, 2H), 4.15 (s, 2H), 6.79 (s, 2H) EI-MS: 351[M$^+$]

[Chem. 71]

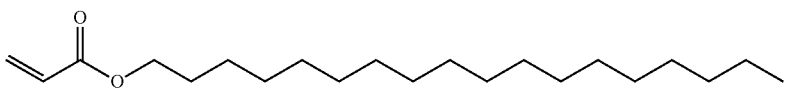
(V-2)

Stearyl acrylate (V-2) (manufactured by Tokyo Chemical Industry Co., Ltd.) was purchased and used.

[Chem. 72]

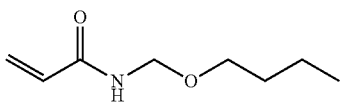
(V-3)

N-(Butoxymethyl)acrylamide (V-3) (manufactured by Tokyo Chemical Industry Co., Ltd.) was purchased and used.

[Chem. 73]

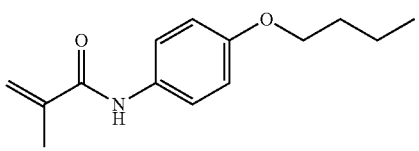
(V-4)

A compound (V-4) was synthesized according to the procedure described in a known document (Farmaco. Edizione Scientifica Vol. 22 (1967) 190, 590-598).

Preparation of Cinnamic Acid Polymer (DCE-1)

Example 13

1 part (10.0 mmol) of a compound represented by the formula (DiCin-1) was dissolved in 10 parts of ethyl methyl ketone to obtain a solution 1. To this solution 1 was added 0.01 parts of azobisisobutyronitrile (AIBN). The mixture was heated to reflux for 2 days under a nitrogen atmosphere to obtain a solution 2. Then, the solution 2 was added dropwise to 60 parts of methanol under stirring, and the precipitated solid was filtered. The obtained solid was dissolved in 5 parts of tetrahydrofuran (THF), the solution was added dropwise to 120 parts of ice-cooled hexane under stirring, and the precipitated solid was filtered. The obtained solid was dissolved in 5 parts of THF, the solution was added dropwise to 120 parts of ice-cooled methanol under stirring, and the precipitated solid was filtered. The obtained solid was dissolved in THF and then dried in vacuo to obtain a polymer (DCE-1).

Preparation of Cinnamic Acid Polymers (DCE-2) to (DCE-12)

In the same manner as for the cinnamic acid polymer (DCE-1), polymers (DCE-2) to (DCE-12) were obtained. The compositions of the respective polymers are as shown in Tables 1 and 2.

TABLE 1

| Sample name | Blending amount (% by mole) | | | | | |
| --- | --- | --- | --- | --- | --- | --- |
| | DiCin-1 | DiCin-2 | DiCin-3 | DiCin-4 | DiCin-5 | DiCin-6 |
| Example 14 DCE-1 | 100 | | | | | |
| Example 15 DCE-2 | | 100 | | | | |
| Example 16 DCE-3 | | | 100 | | | |
| Example 17 DCE-4 | | | | 100 | | |
| Example 18 DCE-5 | | | | | 100 | |
| Example 19 DCE-6 | | | | | | 100 |

TABLE 2

| Sample name | Blending amount (% by mole) | | | | | |
| --- | --- | --- | --- | --- | --- | --- |
| | DiCin-7 | DiCin-8 | DiCin-9 | DiCin-10 | DiCin-11 | DiCin-12 |
| Example 20 DCE-7 | 100 | | | | | |
| Example 21 DCE-8 | | 100 | | | | |
| Example 22 DCE-9 | | | 100 | | | |
| Example 23 DCE-10 | | | | 100 | | |
| Example 24 DCE-11 | | | | | 100 | |
| Example 25 DCE-12 | | | | | | 100 |

Preparation of Cinnamic Acid Polymer (DCEV-1)

Example 26

0.9 parts (9.0 mmol) of the compound represented by the formula (DiCin-1) and 0.1 parts (1.0 mmol) of a compound represented by the formula (V-1) were dissolved in 10 parts of ethyl methyl ketone to obtain a solution 3. To this solution 3 was added 0.01 parts of azobisisobutyronitrile (AIBN). The mixture was heated to reflux for 2 days under a nitrogen atmosphere to obtain a solution 4. Then, the solution 4 was added dropwise to 60 parts of methanol under stirring, and the precipitated solid was filtered. The obtained solid was dissolved in 5 parts of tetrahydrofuran (THF), the solution was added dropwise to 120 parts of ice-cooled hexane under stirring, and the precipitated solid was filtered. The obtained solid was dissolved in 5 parts of THF, the solution was added dropwise to 120 parts of ice-cooled methanol under stirring, and the precipitated solid was filtered. The obtained solid was dissolved in THF and then dried in vacuo to obtain a polymer (DCEV-1).

Preparation of Cinnamic Acid Polymers (DCEV-2) to (DCEV-50)

In the same manner as for the cinnamic acid polymer (DCEV-1), polymers (DCEV-2) to (DCEV-50) were obtained. The compositions of the respective polymers are as shown in Tables 3 and 4.

TABLE 3

| Example | Sample name | Blending amount (% by mole) | | | | | | | | | |
|---|---|---|---|---|---|---|---|---|---|---|---|
| | | DiCin-1 | DiCin-2 | DiCin-3 | DiCin-4 | DiCin-5 | DiCin-6 | V-1 | V-2 | V-3 | V-4 |
| 27 | DCEV-1 | 90 | | | | | | 10 | | | |
| 28 | DCEV-2 | 85 | | | | | | 15 | | | |
| 29 | DCEV-3 | 80 | | | | | | 20 | | | |
| 30 | DCEV-4 | 80 | | | | | | | 20 | | |
| 31 | DCEV-5 | 80 | | | | | | | | 20 | |
| 32 | DCEV-6 | 80 | | | | | | | | | 20 |
| 33 | DCEV-7 | | 80 | | | | | 20 | | | |
| 34 | DCEV-8 | | 80 | | | | | | 20 | | |
| 35 | DCEV-9 | | 80 | | | | | | | 20 | |
| 36 | DCEV-10 | | 80 | | | | | | | | 20 |
| 37 | DCEV-11 | | | 80 | | | | 20 | | | |
| 38 | DCEV-12 | | | 80 | | | | | 20 | | |
| 39 | DCEV-13 | | | 80 | | | | | | 20 | |
| 40 | DCEV-14 | | | 80 | | | | | | | 20 |
| 41 | DCEV-15 | | | | 80 | | | 20 | | | |
| 42 | DCEV-16 | | | | 80 | | | | 20 | | |
| 43 | DCEV-17 | | | | 80 | | | | | 20 | |
| 44 | DCEV-18 | | | | 80 | | | | | | 20 |
| 45 | DCEV-19 | | | | | 80 | | 20 | | | |
| 46 | DCEV-20 | | | | | 80 | | | 20 | | |
| 47 | DCEV-21 | | | | | 80 | | | | 20 | |
| 48 | DCEV-22 | | | | | 80 | | | | | 20 |
| 49 | DCEV-23 | | | | | | 80 | 20 | | | |
| 50 | DCEV-24 | | | | | | 80 | | 20 | | |
| 51 | DCEV-25 | | | | | | 80 | | | 20 | |
| 52 | DCEV-26 | | | | | | 80 | | | | 20 |

TABLE 4

| Example | Sample name | Blending amount (% by mole) | | | | | | | | | |
|---|---|---|---|---|---|---|---|---|---|---|---|
| | | DiCin-7 | DiCin-8 | DiCin-9 | DiCin-10 | DiCin-11 | DiCin-12 | V-1 | V-2 | V-3 | V-4 |
| 53 | DCEV-27 | 80 | | | | | | 20 | | | |
| 54 | DCEV-28 | 80 | | | | | | | 20 | | |
| 55 | DCEV-29 | 80 | | | | | | | | 20 | |
| 56 | DCEV-30 | 80 | | | | | | | | | 20 |
| 57 | DCEV-31 | | 80 | | | | | 20 | | | |
| 58 | DCEV-32 | | 80 | | | | | | 20 | | |
| 59 | DCEV-33 | | 80 | | | | | | | 20 | |
| 60 | DCEV-34 | | 80 | | | | | | | | 20 |
| 61 | DCEV-35 | | | 80 | | | | 20 | | | |
| 62 | DCEV-36 | | | 80 | | | | | 20 | | |
| 63 | DCEV-37 | | | 80 | | | | | | 20 | |
| 64 | DCEV-38 | | | 80 | | | | | | | 20 |
| 65 | DCEV-39 | | | | 80 | | | 20 | | | |
| 66 | DCEV-40 | | | | 80 | | | | 20 | | |
| 67 | DCEV-41 | | | | 80 | | | | | 20 | |
| 68 | DCEV-42 | | | | 80 | | | | | | 20 |
| 69 | DCEV-43 | | | | | 80 | | 20 | | | |
| 70 | DCEV-44 | | | | | 80 | | | 20 | | |
| 71 | DCEV-45 | | | | | 80 | | | | 20 | |
| 72 | DCEV-46 | | | | | 80 | | | | | 20 |

TABLE 4-continued

| Example | Sample name | Blending amount (% by mole) | | | | | | | | |
|---|---|---|---|---|---|---|---|---|---|---|
| | | DiCin-7 | DiCin-8 | DiCin-9 | DiCin-10 | DiCin-11 | DiCin-12 | V-1 | V-2 | V-3 | V-4 |
| 73 | DCEV-47 | | | | | | 80 | 20 | | | |
| 74 | DCEV-48 | | | | | | 80 | | 20 | | |
| 75 | DCEV-49 | | | | | | 80 | | | 20 | |
| 76 | DCEV-50 | | | | | | 80 | | | | 20 |

Preparation of Alignment Layer and Liquid Crystal Display Element

Example 77

The cinnamic acid polymer (DCE-1) was dissolved in cyclopentanone to be 1.0% and the solution was stirred at room temperature for 10 minutes. Then, the solution was applied onto a glass plate as a substrate, using a spin coater, and dried at 100° C. for 3 minutes. Then, the surface was visually observed and as a result, it was found that a polymer was uniformly applied on the glass plate to form a smooth film.

Next, irradiation of linear polarized and parallel light of visible ultraviolet light (wavelength: 313 nm, irradiation intensity: 8 mW/cm$^2$) was performed onto the coated glass plate using an ultrahigh-pressure mercury lamp via a wavelength cut filter, a band-pass filter, and a polarizing filter in a direction of 45 degrees with respect to the substrate. The irradiation dose was 100 mJ/cm$^2$. The thickness of the film was measured and found to be about 50 nm.

A liquid crystal cell was fabricated by using the coated glass plate prepared by the method above. The gap between the plates was set to 10 μm and the two glass plates were bonded in the anti-parallel direction. Next, a nematic liquid crystal mixture having a negative dielectric anisotropy with a composition described below was charged into the cell at a temperature just exceeding a transparent point (Tc=84.4° C.), and then cooled to room temperature. A polarizing plate was placed on the top and the bottom of the liquid crystal cell, and a back light was placed therebelow. The light transmittance was changed by rotating the liquid crystal cell by 90 degrees and dark-light contrast was clearly observed and there was no abnormal domain and alignment non-uniformity, from which it was confirmed that the liquid crystals were normally aligned. The tilt angle of the liquid crystal in the cell was optically measured by a crystal rotation method, and the pretilt angle was found to be 1 degree. A voltage of 5 V was applied to this liquid crystal cell for an application time of 60 microseconds at a span of 167 milliseconds, and the voltage holding ratio after 167 milliseconds from the release of the voltage was measured by means of "VHR-AMP01" manufactured by TOYO Corporation at 23° C., and as a result, the voltage holding ratio (VHR) was found to be 99.4%.

[Chem. 74]

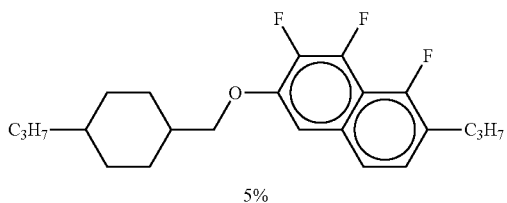

5%

-continued

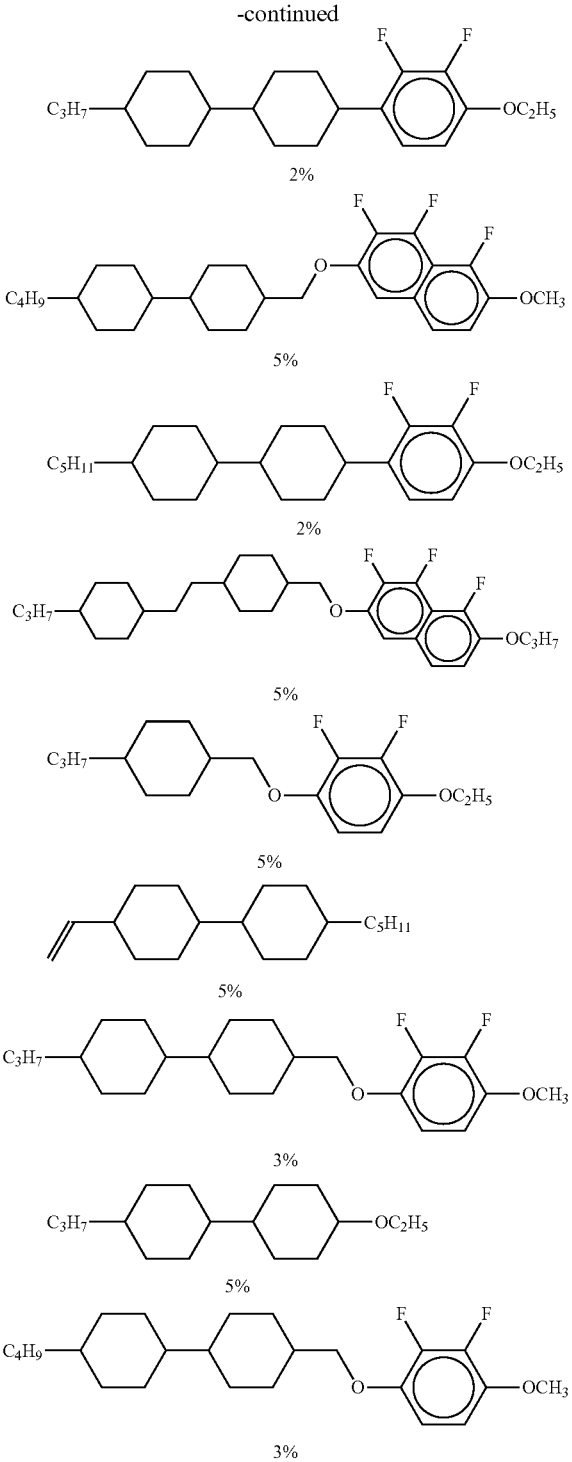

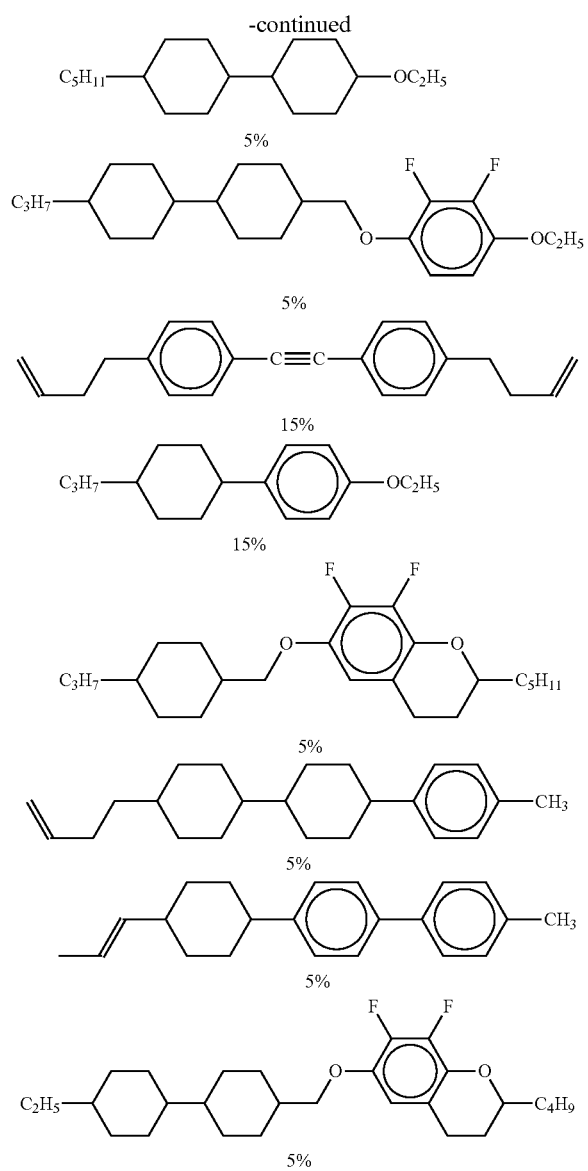

Hereinafter, in the same manner as the cinnamic acid polymer (DCE-1), with respect to (DCE-2) to (DCE-12), and (DCEV-1) to (DCEV-50), alignment layers were fabricated and liquid crystal cells were fabricated. The measurement results of the irradiation doses of linear polarized light, liquid crystal alignment property, pretilt angle, and VHR are shown in conjunction in Table 5. For the irradiation dose of linear polarized light, an irradiation dose of less than 120 mJ/cm² was assumed to be O (good), an irradiation dose of 120 mJ/cm² or more and less than 300 mJ/cm² was assumed to be (acceptable), and an irradiation dose of 300 mJ/cm² or more was assumed to be x (poor). For the liquid crystal alignment property, when the presence or absence of the abnormal domain and alignment non-uniformity of the liquid crystal cell was observed, a case where there was no place where the abnormal domain and alignment non-uniformity are present was assumed to be O (good), a case where there was the abnormal domain and alignment non-uniformity in two or less places was assumed to be Δ (acceptable), and a case where there was the abnormal domain and alignment non-uniformity in three or more places was assumed to be x (poor). For the pretilt angles, the pretilt angles were optically measured by a crystal rotation method, and thus, a case where the pretilt angle was 80 degrees or more and less than 90 degrees was denoted as V, and a case where the pretilt angle was 0 degree or more and less than 15 degrees was denoted as P. For VHR, a case where the VHR was 98% or more was denoted as O (good), a case where the VHR was 95% or more and less than 98% was denoted as (acceptable), and a case where the VHR was 95% or less was denoted as x (poor).

TABLE 5

| | Sample name | Irradiation dose of linear polarized light | Liquid crystal alignment property | Pretilt angle | VHR |
|---|---|---|---|---|---|
| Example 77 | DCE-1 | ○ | ○ | P | ○ |
| Example 78 | DCE-2 | ○ | ○ | P | ○ |
| Example 79 | DCE-3 | ○ | ○ | P | ○ |
| Example 80 | DCE-4 | ○ | ○ | P | ○ |
| Example 81 | DCE-5 | ○ | ○ | P | ○ |
| Example 82 | DCE-6 | ○ | ○ | P | ○ |
| Example 83 | DCE-7 | ○ | ○ | P | ○ |
| Example 84 | DCE-8 | ○ | ○ | P | ○ |
| Example 85 | DCE-9 | ○ | ○ | P | ○ |
| Example 86 | DCE-10 | ○ | ○ | P | ○ |
| Example 87 | DCE-11 | ○ | ○ | P | ○ |
| Example 88 | DCE-12 | ○ | ○ | P | ○ |

TABLE 6

| | Sample name | Irradiation dose of linear polarized light | Liquid crystal alignment property | Pretilt angle | VHR |
|---|---|---|---|---|---|
| Example 89 | DCEV-1 | ○ | ○ | V | ○ |
| Example 90 | DCEV-2 | ○ | ○ | V | ○ |
| Example 91 | DCEV-3 | ○ | ○ | V | ○ |
| Example 92 | DCEV-4 | ○ | ○ | V | ○ |
| Example 93 | DCEV-5 | ○ | ○ | P | ○ |
| Example 94 | DCEV-6 | ○ | ○ | P | ○ |
| Example 95 | DCEV-7 | ○ | ○ | V | ○ |
| Example 96 | DCEV-8 | ○ | ○ | V | ○ |
| Example 97 | DCEV-9 | ○ | ○ | P | ○ |
| Example 98 | DCEV-10 | ○ | ○ | P | ○ |
| Example 99 | DCEV-11 | ○ | ○ | V | ○ |
| Example 100 | DCEV-12 | ○ | ○ | V | ○ |
| Example 101 | DCEV-13 | ○ | ○ | P | ○ |
| Example 102 | DCEV-14 | ○ | ○ | P | ○ |
| Example 103 | DCEV-15 | ○ | ○ | V | ○ |
| Example 104 | DCEV-16 | ○ | ○ | V | ○ |
| Example 105 | DCEV-17 | ○ | ○ | P | ○ |
| Example 106 | DCEV-18 | ○ | ○ | P | ○ |
| Example 107 | DCEV-19 | ○ | ○ | V | ○ |
| Example 108 | DCEV-20 | ○ | ○ | V | ○ |
| Example 109 | DCEV-21 | ○ | ○ | P | ○ |
| Example 110 | DCEV-22 | ○ | ○ | P | ○ |
| Example 111 | DCEV-23 | ○ | ○ | V | ○ |
| Example 112 | DCEV-24 | ○ | ○ | V | ○ |
| Example 113 | DCEV-25 | ○ | ○ | P | ○ |
| Example 114 | DCEV-26 | ○ | ○ | P | ○ |

TABLE 7

| Sample name | Irradiation dose of linear polarized light | Liquid crystal alignment property | Pretilt angle | VHR |
|---|---|---|---|---|
| Example 115 DCEV-27 | ○ | ○ | V | ○ |
| Example 116 DCEV-28 | ○ | ○ | V | ○ |
| Example 117 DCEV-29 | ○ | ○ | P | ○ |
| Example 118 DCEV-30 | ○ | ○ | P | ○ |
| Example 119 DCEV-31 | ○ | ○ | V | ○ |
| Example 120 DCEV-32 | ○ | ○ | V | ○ |
| Example 121 DCEV-33 | ○ | ○ | P | ○ |
| Example 123 DCEV-34 | ○ | ○ | P | ○ |
| Example 124 DCEV-35 | ○ | ○ | V | ○ |
| Example 125 DCEV-36 | ○ | ○ | V | ○ |
| Example 126 DCEV-37 | ○ | ○ | P | ○ |
| Example 127 DCEV-38 | ○ | ○ | P | ○ |
| Example 128 DCEV-39 | ○ | ○ | V | ○ |
| Example 129 DCEV-40 | ○ | ○ | V | ○ |
| Example 130 DCEV-41 | ○ | ○ | P | ○ |
| Example 131 DCEV-42 | ○ | ○ | P | ○ |
| Example 132 DCEV-43 | ○ | ○ | V | ○ |
| Example 133 DCEV-44 | ○ | ○ | V | ○ |
| Example 134 DCEV-45 | ○ | ○ | P | ○ |
| Example 135 DCEV-46 | ○ | ○ | P | ○ |
| Example 136 DCEV-47 | ○ | ○ | V | ○ |
| Example 137 DCEV-48 | ○ | ○ | V | ○ |
| Example 138 DCEV-49 | ○ | ○ | P | ○ |
| Example 139 DCEV-50 | ○ | ○ | P | ○ |

From the above results, it can be seen that an alignment layer, which allows a small irradiation dose of linear polarized light, and has a superior liquid crystal alignment property and a superior ability to control the pretilt, and exhibits a high voltage holding ratio, can be obtained by the cinnamic acid polymerized product obtained by polymerizing the cinnamic acid derivatives of the present invention.

Comparative Example 1

For comparison, cinnamic acid derivatives (D-1) and (D-3) were synthesized, and thus, by the same method as in Example 13, cinnamic acid polymers (CE-1) to (CE-2) and (CEV-1) to (CEV-8) were prepared.

TABLE 8

| Sample name | | Blending amount (% by mole) | | | | | |
|---|---|---|---|---|---|---|---|
| | name | D-1 | D-3 | V-1 | V-2 | V-3 | V-4 |
| Comparative Example 1 | CE-1 | 100 | | | | | |
| Comparative Example 2 | CE-2 | | 100 | | | | |
| Comparative Example 3 | CEV-1 | 80 | | 20 | | | |
| Comparative Example 4 | CEV-2 | 80 | | | 20 | | |
| Comparative Example 5 | CEV-3 | 80 | | | | 20 | |
| Comparative Example 6 | CEV-4 | 80 | | | | | 20 |
| Comparative Example 7 | CEV-5 | | 80 | 20 | | | |
| Comparative Example 8 | CEV-6 | | 80 | | 20 | | |
| Comparative Example 9 | CEV-7 | | 80 | | | 20 | |
| Comparative Example 10 | CEV-8 | | 80 | | | | 20 |

Furthermore, by the same method as in Example 77, an alignment layer was fabricated, and various measurements were conducted and the results therefrom are shown in Table 9.

TABLE 9

| Sample name | Irradiation dose of linear polarized light | Liquid crystal alignment property | Pretilt angle | VHR |
|---|---|---|---|---|
| Comparative Example 11 | CE-1 | Δ | ○ | P | Δ |
| Comparative Example 12 | CE-2 | Δ | ○ | P | Δ |
| Comparative Example 13 | CEV-1 | Δ | Δ | V | ○ |

[Chem. 75]

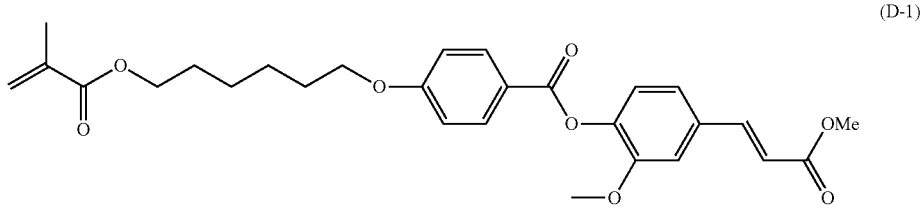

(D-1)

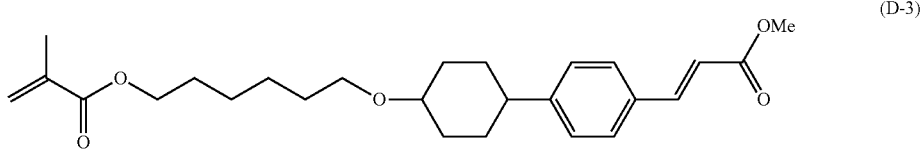

(D-3)

TABLE 9-continued

| Sample name | Irradiation dose of linear polarized light | Liquid crystal alignment property | Pretilt angle | VHR |
|---|---|---|---|---|
| Comparative Example 14 CEV-2 | Δ | Δ | V | ○ |
| Comparative Example 15 CEV-3 | Δ | ○ | P | Δ |
| Comparative Example 16 CEV-4 | Δ | ○ | P | Δ |
| Comparative Example 17 CEV-5 | Δ | Δ | V | ○ |
| Comparative Example 18 CEV-6 | Δ | Δ | V | ○ |
| Comparative Example 19 CEV-7 | Δ | ○ | P | Δ |
| Comparative Example 20 CEV-8 | Δ | ○ | P | Δ |

Therefore, it can be seen that a liquid crystal alignment layer, and a display element using the liquid crystal alignment layer, each of which allows a small irradiation dose of linear polarized light during the production, and has the effects, such as having a superior ability to control the alignment of the liquid crystals and the pretilt angles, and exhibits a high voltage holding ratio (VHR), can be obtained by using the compound (cinnamic acid derivative) of the present invention and a polymer thereof.

INDUSTRIAL APPLICABILITY

The present invention provides a liquid crystal alignment layer which is efficiently provided with an alignment property at a low dose of irradiation of polarized light during the production, and has a superior ability to control the alignment of the liquid crystals and the pretilt angles, and a high voltage holding ratio (VHR); a polymer used for the liquid crystal alignment layer; a compound constituting the polymer; a liquid crystal display element using the liquid crystal alignment layer; and an optical anisotropic body using the polymer.

The invention claimed is:

1. A polymer constituted with a cured product, wherein the cured product has a structural unit represented by the general formula (V):

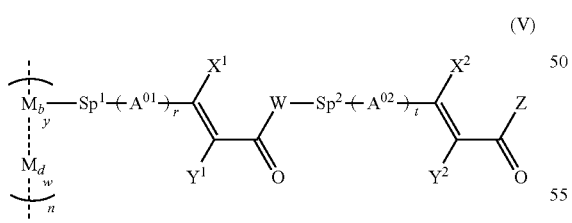

(V)

wherein $Sp^1$ and $Sp^2$ each represent a spacer unit, $A^{01}$ and $A^{02}$ each independently represent a group selected from the group consisting of:
(a) a trans-1,4-cyclohexylene group wherein one methylene group or two or more non-adjacent methylene groups present in this group may be substituted with —O—, —NH—, or —S—,
(b) a 1,4-phenylene group wherein one or two or more —CH='s present in this group may be substituted with —N=, and
(c) a 1,4-cyclohexenylene group, a 2,5-thiophenylene group, a 2,5-furanylene group, a 1,4-bicyclo(2.2.2) octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group,
$X^1$, $X^2$, $Y^1$ and $Y^2$ each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups may be substituted with —O—, —CO—O—, —O—CO—, —CH=CH— or a combination thereof,
Z is represented by the general formula (IIa) or (IIb):

(IIa)

(IIb)

in which the dashed line represents a bond to a carbon atom, to which Z is bonded, and
$R^1$ $R^2$ each independently represent a hydrogen atom or a linear or branched alkyl group having 1 to 30 carbon atoms, wherein one —$CH_2$—group or two or more non-adjacent —$CH_2$— groups in $R^1$ and $R^2$ may be substituted with —O—, —CO—, —CO—O—, —O—CO—, —CO—NH—, —NH—CO—, —$NCH_3$—, —CH=CH—, —CF=CF—, —C≡C—, or a combination thereof, wherein one or two or more —$CH_2$— groups in $R^1$ and $R^2$ may be each independently substituted with a cycloalkyl group with a 3- to 8-membered ring, and a hydrogen atom in $R^1$ and $R^2$ may be substituted with an alkyl group having 1 to 20 carbon atoms, a cyano group, or a halogen atom,
W represents —O— or —$NR^3$—, in which $R^3$ represents a hydrogen atom, a linear or branched alkyl group having 1 to 20 carbon atoms, or a cycloalkyl group with a 3- to 8-membered ring, which may have the alkyl group interposed therein as a linking group, a hydrogen atom in the alkyl group may be unsubstituted or may be substituted with a fluorine atom or a chlorine atom, a hydrogen atom in the cycloalkyl group may be unsubstituted or may be substituted with an alkyl group having 1 to 10 carbon atoms, an alkoxy group having 1 to 10 carbon atoms, a fluorine atom, or a chlorine atom, and r and t each independently represent 1 or 2, $M_b$ and $M_d$ each represent a monomer unit of the polymer, y and w each represent a molar fraction of the copolymer, each satisfying $0<y\leq1$ and $0\leq w<1$, n represents 4 to 100,000, the order in which $M_b$ and $M_d$ are arranged may be the same as or different from that shown in the formula, and the monomer units of $M_b$ and $M_d$ may be each independently constituted with one or two or more different units.

2. The polymer according to claim 1, wherein $M_b$ in the general formula (V) represents any one or more selected from the group consisting of the general formulae (QIII-A-1) to (QIII-A-17):

(QIII-A-1) 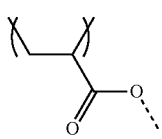

(QIII-A-2) 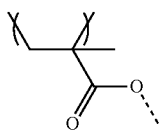

(QIII-A-3) 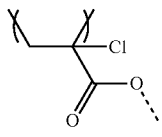

(QIII-A-4) 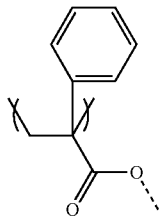

(QIII-A-5) 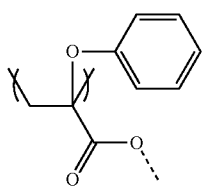

(QIII-A-6) 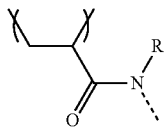

(QIII-A-7) 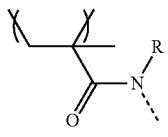

(QIII-A-8) 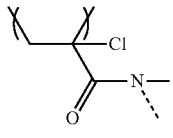

(QIII-A-9) 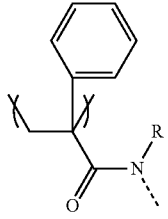

(QIII-A-10) 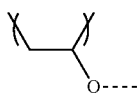

-continued (QIII-A-11) 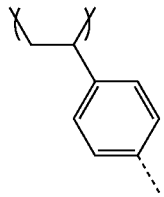

(QIII-A-12) 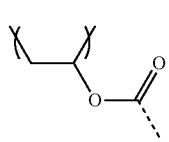

(QIII-A-13) 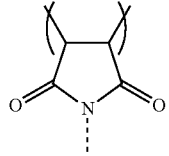

(QIII-A-14) 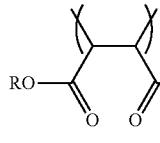

(QIII-A-15) 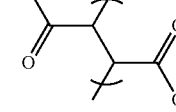

(QIII-A-16)

(QIII-A-17) 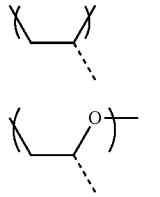

wherein the dashed line represents a bond to Sp$^1$, R's independently represent a hydrogen atom or an alkyl group having 1 to 5 carbon atoms, and any hydrogen atom in each of the structures may be substituted with a fluorine atom, a chlorine atom, a methyl group, or a methoxy group.

3. The polymer according to claim 1, wherein $M_d$ in the general formula (V) represents any one or more selected from the group consisting of the general formulae (QIII-1) to (QIII-17):

(QIII-1)

(QIII-2)

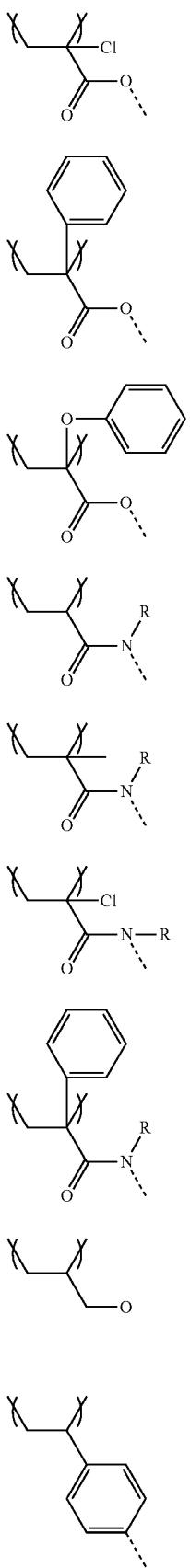

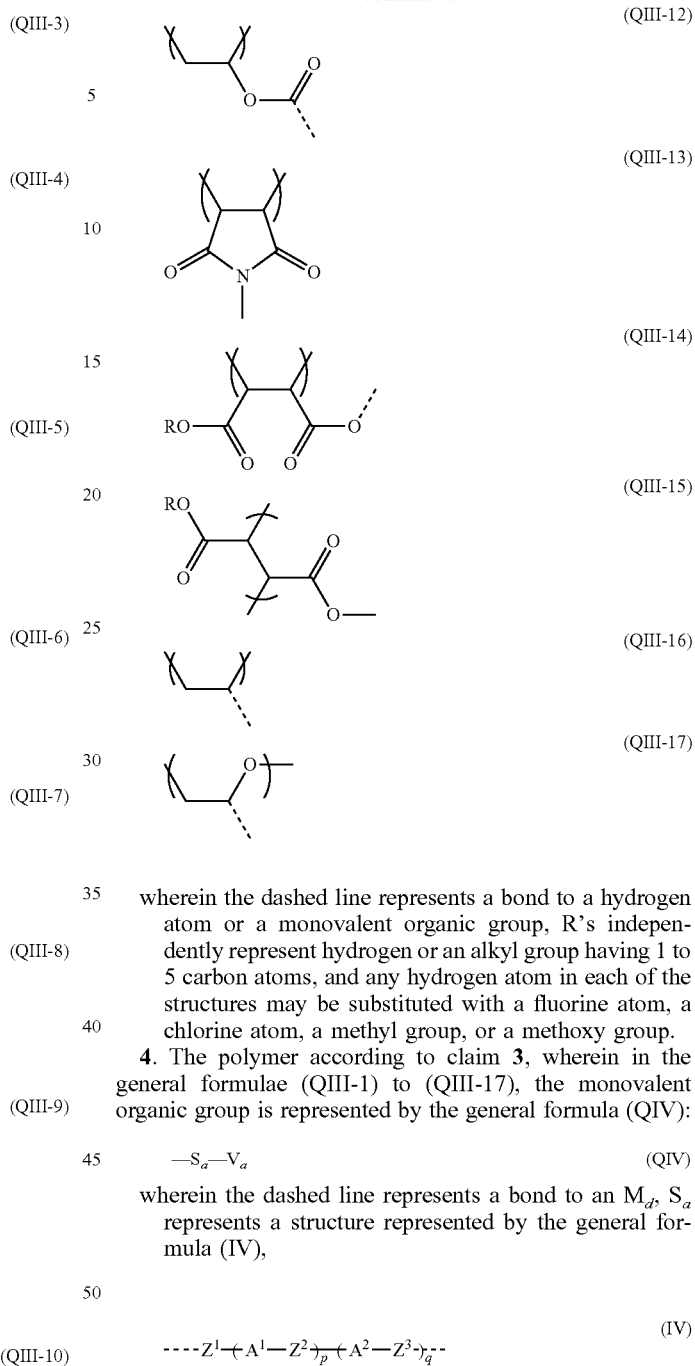

wherein the dashed line represents a bond to a hydrogen atom or a monovalent organic group, R's independently represent hydrogen or an alkyl group having 1 to 5 carbon atoms, and any hydrogen atom in each of the structures may be substituted with a fluorine atom, a chlorine atom, a methyl group, or a methoxy group.

4. The polymer according to claim 3, wherein in the general formulae (QIII-1) to (QIII-17), the monovalent organic group is represented by the general formula (QIV):

$$-S_a-V_a \qquad (QIV)$$

wherein the dashed line represents a bond to an $M_d$, $S_a$ represents a structure represented by the general formula (IV), $$----Z^1-(A^1-Z^2)_p-(A^2-Z^3)_q--- \qquad (IV)$$

wherein in $Sp^1$, the left dashed line represents a bond to L and the right dashed line represents a bond to $A^{o1}$, and in $Sp^2$, the left dashed line represents a bond to W and the right dashed line represents a bond to $A^{o2}$, in $Sp^1$ and $Sp^2$, independently, $Z^1$, $Z^2$ and $Z^3$ each independently represent a single bond, $-(CH_2)_u-$ in which u represents 1 to 20, $-OCH_2-$, $-CH_2O-$, $-COO-$, $-OCO-$, $-CH=CH-$, $-CF=CF-$, $-CF_2O-$, $-OCF_2-$, $-CF_2CF_2-$, or $-C\equiv C-$, and one or more of the non-adjacent $CH_2$ groups in these groups may be independently substituted with $-O-$, $-CO-$, $-CO-O-$, $-O-CO-$, $-Si(CH_3)_2-O-Si(CH_3)_2-$, $-NR-$, —NR—CO—, —CO—NR—, —NR—CO—O—, —O—CO—NR—, —NR—CO—NR—, —CH═CH—, —C≡C—, or —O—CO—O—, in which R's independently represent hydrogen or an alkyl group having 1 to 5 carbon atoms, and $A^1$ and $A^2$ each independently represent a group selected from the group consisting of:
(a) a trans-1,4-cyclohexylene group, in which one methylene group or two or more non-adjacent methylene groups present in this group may be substituted with —O—, —NH—, or —S—,
(b) a 1,4-phenylene group in which one or two or more —CH═'s present in this group may be substituted with —N═, and
(c) a 1,4-cyclohexenylene group, a 2,5-thiophenylene group, a 2,5-furanylene group, a 1,4-bicyclo(2.2.2) octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, and p represents 0 or 1, and q represents 0, 1, or 2, and
$V_a$ represents a structure represented by the following general formula (VI):

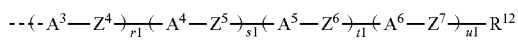

(VI)

wherein the dashed line represents a bond to $S_a$,
$Z^4$, $Z^5$, $Z^6$ and $Z^7$ each independently represent a single bond, —$(CH_2)_u$— in which u represents 1 to 20, —$OCH_2$—, —$CH_2O$—, —COO—, —OCO—, —CH═CH—, —CF═CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —Si$(CH_3)_2$—O—Si$(CH_3)_2$—, —NR—, —NR—CO—, —CO—NR—, —NR—CO—O—, —O—CO—NR—, —NR—CO—NR—, —CH═CH—, —C≡C—, or —O—CO—O— in which R's independently represent hydrogen or an alkyl group having 1 to 5 carbon atoms, $A^3$, $A^4$, $A^5$ and $A^6$ each independently represent a group selected from the group consisting of:
(a) a trans-1,4-cyclohexylene group wherein one methylene group or two or more non-adjacent methylene groups present in this group may be substituted with —O—, —NH—, or —S—,
(b) a 1,4-phenylene group wherein one or two or more —CH═'s present in this group may be substituted with —N═, and
(c) a 1,4-cyclohexenylene group, a 2,5-thiophenylene group, a 2,5-furanylene group, a 1,4-bicyclo(2.2.2) octylene group, a naphthalene-1,4-diyl group, a naphthalene-2,6-diyl group, a decahydronaphthalene-2,6-diyl group, or a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one $CH_2$ group or two or more non-adjacent $CH_2$ groups may be substituted with —O—, —CO—O—, —O—CO—, —CH═C—, or a combination thereof.

5. A liquid crystal alignment layer for a vertical alignment mode liquid crystal display element, using the polymer according to claim 1.

6. A vertical alignment mode liquid crystal display element using the liquid crystal alignment layer according to claim 5.

7. A liquid crystal alignment layer for a horizontal alignment mode liquid crystal display element, using the polymer according to claim 1.

8. A horizontal alignment mode liquid crystal display element using the liquid crystal alignment layer according to claim 7.

9. A liquid crystal alignment layer for an optical anisotropic body, using the polymer according to claim 1.

10. An optical anisotropic body constituted with a polymer of a polymerizable liquid crystal composition, wherein polymerizable liquid crystal molecules in the polymerizable liquid crystal composition are aligned using the liquid crystal alignment layer according to claim 9.

* * * * *